(12) United States Patent
Combrink et al.

(10) Patent No.: US 8,252,793 B2
(45) Date of Patent: Aug. 28, 2012

(54) BRADYKININ RECEPTOR AGONISTS AND USES THEREOF TO TREAT OCULAR HYPERTENSION AND GLAUCOMA

(75) Inventors: Keith D. Combrink, Arlington, TX (US); Suchismita Mohapatra, Arlington, TX (US); Mark R. Hellberg, Arlington, TX (US); Najam A. Sharif, Arlington, TX (US); Ganesh Prasanna, Fort Worth, TX (US); Iok-Hou Pang, Grand Prairie, TX (US); Bryon Severns, Arlington, TX (US); Hwang-Hsing Chen, Fort Worth, TX (US); Abdelmoula Namil, Arlington, TX (US)

(73) Assignees: Alcon Research, Ltd., Fort Worth, TX (US); Astellas Pharma Inc., Tokyo (JP)

(*) Notice: Subject to any disclaimer, the term of this patent is extended or adjusted under 35 U.S.C. 154(b) by 0 days.

(21) Appl. No.: 13/211,827

(22) Filed: Aug. 17, 2011

(65) Prior Publication Data

US 2012/0046285 A1 Feb. 23, 2012

Related U.S. Application Data

(60) Provisional application No. 61/374,740, filed on Aug. 18, 2010.

(51) Int. Cl.
*A61K 31/5377* (2006.01)
*A61K 31/444* (2006.01)
*A61K 31/496* (2006.01)
*A61K 31/4545* (2006.01)
*A61K 31/506* (2006.01)
*A61K 31/4439* (2006.01)
*C07D 401/14* (2006.01)
*C07D 498/04* (2006.01)
*C07D 413/14* (2006.01)
*C07D 401/06* (2006.01)
*A61P 9/12* (2006.01)
*A61P 27/06* (2006.01)

(52) U.S. Cl. ............ 514/234.5; 514/338; 514/333; 514/302; 514/253.09; 514/318; 514/275; 546/116; 546/194; 546/273.7; 546/256; 544/364; 544/331; 544/131

(58) Field of Classification Search .......... 546/153, 546/194, 116, 273.7, 256; 514/338, 314, 514/234.5, 333, 302, 253.09, 318, 275; 544/360, 544/124, 364, 331, 131
See application file for complete search history.

(56) References Cited

U.S. PATENT DOCUMENTS

| | | | |
|---|---|---|---|
| 4,883,814 A | 11/1989 | Baldwin et al. | |
| 5,153,192 A | 10/1992 | Dean et al. | |
| 5,212,196 A | 5/1993 | House et al. | |
| 5,240,923 A | 8/1993 | Dean et al. | |
| 5,464,831 A | 11/1995 | Dean et al. | |
| 5,500,230 A | 3/1996 | Nathanson | |
| 5,538,966 A | 7/1996 | May et al. | |
| 5,612,364 A | 3/1997 | York et al. | |
| 6,015,818 A | 1/2000 | Oku et al. | |
| 6,156,753 A | 12/2000 | Doherty et al. | |
| 6,242,441 B1 | 6/2001 | Kothe et al. | |
| 6,242,442 B1 | 6/2001 | Dean et al. | |
| 6,316,441 B1 | 11/2001 | Dean et al. | |
| 6,399,605 B1 | 6/2002 | Maurin et al. | |
| 6,500,831 B1 | 12/2002 | Sharif | |
| 6,520,970 B1 | 2/2003 | Sanchez-Martinez | |
| 7,005,446 B1 | 2/2006 | Shade et al. | |
| 2002/0151550 A1 | 10/2002 | DeSimone et al. | |
| 2005/0244461 A1 | 11/2005 | Nivaggioli et al. | |

FOREIGN PATENT DOCUMENTS

| | | |
|---|---|---|
| EP | 1772514 A2 | 4/2007 |
| WO | 9428902 | 12/1994 |
| WO | 9616644 | 6/1996 |
| WO | 0119802 A1 | 3/2001 |
| WO | 03092584 A2 | 11/2003 |
| WO | 2006041875 A1 | 4/2006 |
| WO | 2006119258 A2 | 11/2006 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Sawada, et al.; "Discovery of the first non-peptide full agonists for the human bradykinin B2 receptor incorporating 4-(2-Picolyloxy)quinoline and 1-(2-Picolyl)benzimidazole frameworks"; Journal of Medicinal Chemistry; vol. 47; No. 11; pp. 2853-2863 (May 1, 2004).
Search Report and Written Opinion dated Feb. 22, 2012, corresponding to PCT Application Serial No. PCT/US2011/048110.
Sharif and Xu; "Pharmacological characterization of bradykinin receptors coupled to phosphoinositide turnover in SV/40-immortalized human trabecular meshwork cells"; Exp. Eye Res.; vol. 63; pp. 631-637 (1996).
Sharif et al.; "Human trabecular meshwork cells express functional serotonin-2A (5HT2A) receptors: role in IOP reduction"; Investigative Ophthalmology & Visual Science; vol. 47; No. 9; pp. 4001-4010 (2006).
Sharif et al; "Levobetaxolol (Betaxon) and other B-adrenergic antagonists: preclinical pharmacology, IOP-lowering activity and sites of action in human eyes"; Journal of Ocular Pharmacology and Therapeutics; vol. 17; No. 4; pp. 305-317 (2001).
Sharif et al; "Pharmacology of [3H]Prostaglandin E1/[3H]Prostaglandin E2 and [3H]Prostaglandin F2a binding to EP3 and FP prostaglandin receptor binding sites in bovine corpus luteum: characterization and correlation with functional data"; vol. 286; No. 2; pp. 10941102 (1998).

(Continued)

*Primary Examiner* — Niloofar Rahmani
(74) *Attorney, Agent, or Firm* — Jason J. Derry

(57) ABSTRACT

The invention provides compositions and methods for treating and/or preventing ocular disorders associated with increased intraocular pressure. In particular, the compounds are bradykinin agonists.

7 Claims, No Drawings

OTHER PUBLICATIONS

Sharif et al; "Human corneal epithelial cell functional responses to inflammatory agents and their antagonists"; Investigative Ophthalmology and Visual Science; vol. 39; No. 13; pp. 2562-2571 (1998).

Sharif et al.; "Molecular pharmacology of the DP/EP2 class prostaglandin AL-6598 and quantitative autoradiographic visualization of DP and EP2 receptor sites in human eyes"; Journal of Ocular Pharmacology and Therapeutics; vol. 20; No. 6; pp. 489-509 (2004).

Sharif et al.; "Human ciliary muscle cell responses to FP-class prostaglandin analogs: phosphoinositide hydrolysis, intracellular Ca2+ mobilization and MAP kinase activation"; Journal of Ocular Pharmacology and Therapeutics; vol. 19; No. 5; pp. 437-455 (2003).

Sharif et al.; "prelinical pharmacology of AL-12182, a new ocular hypotensive 11-Oxa prostaglandin analog"; Journal of Ocular Pharmacology and Therapeutics; vol. 22; No. 5; pp. 291-309 (2006).

Sharif et al.; "Pharmacological and molecular biological (RT-PCR) characterization of functional TP prostanoid receptors in immortalized human non-pigmented ciliary epithelial cells"; vol. 18; No. 2; pp. 141-162 (2002).

Sharif et al.; "Bradykinin-induced accumulation of [2H]inositol-1-phosphate in human embryonic pituitary tumor cells by activation of a B2-receptor"; Neuroscience Letters; vol. 86; pp. 279-283 (1988).

Sharma; "Therapeutic prospects of bradykinin receptor antagonists"; Gen. Pharmac.; vol. 24; No. 2; pp. 267-274 (1993).

Sharma and Magde; "Activation of soluble guanylate cyclase by carbon monoxide and nitric oxide: a mechanistic model"; Methods; vol. 19; pp. 494-505 (1999).

Snyder et al.; "Nitric oxide and carbon monoxide: parallel roles as neural messengers"; Brain Research Reviews; vol. 26; pp. 167-175 (1998).

Srisook et al; "CO from enhanced HO activity or form CORM-2 inhibits both O2- and NO production and downregulates HO-1 expression in LPS-stimulated macrophages"; Biochemical Pharmacology; vol. 71; pp. 317-318 (2006).

Stjernschantz et al; "Preclinical pharmacology of latanoprost, a phenyl-substituted PGF2a analogue"; Advance in Prostaglandin, Thromboxane, and Leukotriene Research; vol. 23; pp. 513-518; (1995).

Stone and Marletta; "Synergistic activation of soluble guanylate cyclase by YC-1 and carbon monoxide: implications for the role of cleavage of the iron-histidine bond during activation by nitric oxide"; Research Paper; Chem. Biol.; vol. 5; pp. 255-261 (1998).

Stumpff et al.; "Stimulatoin of cannabinoid (CB1) and prostanoid (EP2) receptors opens BKCa channels and relaxes ocular trabecular meshwork"; Experimental Eye Research; vol. 80; pp. 697-708 (2005).

Sugrue; "New approaches in antiglaucoma therapy"; Journal of Medicinal Chemistry; vol. 40; No. 18; pp. 2793-2809 (Aug. 29, 1997).

Tamaki et al; "Effect of topical betaxolol on tissue circulation in the human optic nerve head"; Journal of ocular pharmacology and therapeutics; vol. 15; No. 4; pp. 313-321 (1999).

Webb et al.; "Kinin modulation of conventional outflow facility in the bovine eye"; Journal of ocular pharmacology and therapeutics; vol. 22; No. 5; pp. 310-316 (2006).

Wiederholt et al.; "The regulation of trabecular meshwork and ciliary muscle contractility"; Prog. Retinal Eye Res.; vol. 19; pp. 271-295 (2000).

Wiernas et al.; "Effects of bradykin in on signal transduction, cellproliferation, and cytokine, prostaglandin E2 and collagenase-1 release from human corneal epithelial cells"; British Journal of Pharmacology; vol. 123; pp. 1127-1137 (1998).

Woodward et al.; Pharmacological characterization of a novel antiglaucoma agent, bimatoprost (AGN 192024); The Journal of Pharmacology and Experimental Therapeutics; vol. 305; No. 2; pp. 772-775 (2003).

Wu et al.; "A nitric oxide (NO)-releasing derivative of gabapentin, NCX 8001, alleviates neuropathic pain-like behavior after spinal cord and peripheral nerve injury"; British Journal of Pharmacology; vol. 141; pp. 65-74 (2004).

Yokoyama et al.; "Implicatoin of polymodal receptor activities in intraocular pressure elevation by neurogenic inflammation"; Jpn. J. Ophthalmol.; vol. 34; pp. 245-255 (1990).

ALM; "Prostaglandin derivates as ocular hypotensive agents"; Progress in Retinal Eye Research; vol. 17; No. 3; pp. 291-312 (1998).

Bhoola et al.; "Bioregulatoin of kinins: kallikreins, kininogens, and kininases"; Pharmacological Reviews; vol. 44; No. 1; pp. 1-80 (1992).

Boehning and Snyder; "Novel neural modulators"; Annu. Rev. Neurosci. vol. 26; pp. 105-131 (2003).

Boels and Schaller; "Identification and characterization of GPR100 as a novel human G-protein-coupled bradykinin receptor" British Journal of Pharamcology; vol. 140; pp. 932-938 (2003).

Chen et al; "Human ACE and bradykinin B2 receptors form a complex at the plasma membrane"; The FASEB Journal; vol. 20; pp. 2261-2270 (2006).

Chiang; "Effects of intravenous infusions of histamine 5-hydroxytryptamine, bradykinin and prostaglandins on intraocular pressure"; Arch. Int. Pharmacodyn.; vol. 207; pp. 131-138 (1974).

Aclark and Pang; "Advances in glaucoma therapeutics"; Expert Opinion Emerging Drugs; vol. 7; No. 1; pp. 141-163 (2002).

Clark and Yorio; Ophthalmic drug discovery; Nature Rev. Drug Discovery; vol. 2; pp. 448-459 (2003).

Cole and Unger; "Action of bradyinin on intraocular pressure and pupillary diameter"; Ophthal. Res.; vol. 6; pp. 308-314 (1974).

Crider and Sharif; "Adeenylyl cyclase activity mediated by B-adrenoceptors in immortalized human trabecular meshwork and non-pigmented ciliary epithelial cells"; Journal of Ocular Pharmacology and Therapeutics; vol. 18; No. 3; pp. 221-230 (2002).

Evgenov et al; "NO-independent stimulators and activators of soluble guanylate cyclase: discovery and therapeutic potential"; Reviews; Nature; Drug Discovery; vol. 5; pp. 755-768 (Sep. 2006).

Funk et al; "Intraocular pressure and systemic blood pressure after administration of vasoactive substances in hypertensive and normal rats"; Graefe's Arch. Clin. Exp. Ophthalmol.; vol. 223; pp. 145-149 (1985).

Green and Elijah; "Drug effects on aqueous humor formation and pseudofacility in normal rabbit eyes"; Exp. Eye Res.; vol. 33; pp. 239-245 (1981).

Hall; "Bradykinin receptors: pharmacological properties and biological roles"; Pharmac. Ther.; vol. 56; pp. 131-190 (1992).

Hellberg; "Preclinical efficacy of travoprost, a potent and selective FP prostaglandin receptor agonist"; Journal of Ocular Pharmacology; vol. 17; No. 5; pp. 421-432 (2001).

Huang et al.; "Modulation by bradykinin of angiotensin type 1 receptor-evoked RhoA activation of connective tissue growth factor expression in human lung fibroblasts"; Am. J. Physiol. Lung Clel Mol. Physiol.; vol. 290; pp. L1291-L1299 (2006).

Ito et al.; "Bradykinin inhibits development of myocardial infarction through B2 receptor signalling by increment of regional blood flow around the ischaemic lesions in rats"; British Journal of Pharmacology; vol. 138; pp. 225-233 (2003).

Kaufman et al; "Effect of serotonin, histamine and bradykinin on outflow facility following ciliary muscle retrodisplacement in the cynomolgus monkey"; Exp. Eye. Res.; vol. 35; pp. 191-199 (1982).

Kelly and Sharif; "Pharmacological evidence for a functional serotonin-2B receptor in a human uterine smooth muscle cell line"; Journal of Pharmacology and Experimental Therapeutics; vol. 317; No. 3; pp. 1254-1261 (2006).

Kelly et al.; "Real-time intracellular Ca2+ mobilization by Travoprost acid, Bimatoprost, Unoprostone, and other analogs via endogenous mouse, rat and cloned human FP prostaglandin receptors"; Journal of Pharmacology and Experimental Therapeutics; vol. 304; No. 1; pp. 238-245 (2003).

Kimura et al.; "Physiological roles of hydrogen sulfide: synaptic modulation, neuroprotection, and smooth muscle relaxation—Forum Review"; Antioxidants and Redox Signaling; vol. 7; No. 5 & 6; pp. 795-803 (2005).

Lai et al; "A novel bradykinin-related peptide form skin secretions of toad Bombina maxima and its precursor containing six identical copies of the final product"; Biochemical and Biophysical Research Communications; vol. 286; pp. 259-263 (2001).

Lai et al.; "Bombinakinin M gene associated peptide, a novel bioactive peptide from skin secretions of the toad *Bombina maxima*"; Peptides; vol. 24; pp. 199-204 (2003).

Lee et al.; "Cloning of bradykinin precursor cDNAs from skin of *Bombina maxima* reveals novel bombinakinin M antagonists and a bradykinin potential peptide"; Regulatory Peptides; vol. 127; pp. 207-215 (2005).

Leeb-Lundberg et al.; "International union of pharamcology. XLV. Classification of the kinin receptor family: from molecular mechanisms to pathophysiological consequences"; Pharmacological Reviews; vol. 57; No. 1; pp. 27-77 (2005).

Leffler et al; "Nitric oxide increases carbon monoxide production by piglet cerebral microvessels"; Am. J. Physiol. Heart Circ. Physiol; vol. 289; pp. H1442-H1447; (2005).

Llobet et al.; "Bradykinin decreases outflow facility in perfused anterior segments and induces shape changes in passaged BTM cells in vitro"; Invest. Ophthalmol. Vis. Sci.; vol. 40; pp. 113-125 (1999).

Ma et al.; "Expression and cellular localization of the kallikrein-kinin system in human ocular tissues"; Exp. Eye Res.; vol. 63; pp. 19-26 (1996).

Majima et al.; "A nonpeptide mimic of bradykinin blunts the development of hypertension in young spontaneously hypertensive rats"; Hypertension; vol. 35; pp. 437-442 (2000).

Mao et al.; "Correlation between intraocular pressure control and progressive glaucomatous damage in primary open-angle glaucoma"; American Journal of Ophthalmology; vol. 111; pp. 51-55 (Jan. 1991).

Marshall and Moore; "Effect of nitric oxide releasing paracetamol and flurbiprofen on cytokoins production in human blood"; European Journal of Pharmacology; vol. 483; pp. 317-322 (2004).

May et al.; "Evaluation of the ocular hypotensive response of serotonin 5-HT1A and 5-HT2 receptor ligands in conscious ocular hypertensive cynomolgus monkeys"; Journal of Pharmacology and Experimental Therapeutics; vol. 306; No. 1; pp. 301-307 (2003).

Meini et al.; Bradykinin B2 and GPR100 receptors: a paradigm receptor signal transduction pharmacology; British Journal of Pharmacology; vol. 143; pp. 938-941 (2004).

Menniti et al.; "Phosphodiesterases in the CNS: targets for drug development"; Reviews: Nat. Rev. Drug Discovery; vol. 5; pp. 660-670 (2006).

Nathanson; "Direct application of a guanylate cyclase activator lowers intraocular pressure"; Rapid Communication; European Journal of Pharmacology; vol. 147; pp. 155-156 (1988).

Nathanson; "Nitrovasodilators as a new class of hypotensive agents"; Journal of Pharmacology and Experimental Therapeutics; vol. 260; No. 3; pp. 956-965 (1992).

Noda et al.; "Neuroprotective role of bradykinin because of the attenuation of pro-inflammatory cytokine release from activated microglia"; Journal of Neurochemistry; vol. 101; pp. 397-410 (2007).

O'Rourke et al.; "The smooth muscle pharmacology of maximakinin, a receptor-selective, bradykinin-related nonadecapeptide from the venom of the Chinese toad, *Bombina maxima*"; Regulatory Peptides; vol. 121; pp. 65-72 (2004).

Park et al.; "Pharmacological characterization of vasorelaxant effects of BMS-180448, a novel cardioselective ATP-sensitive potassium channel opener, in rat aorta"; J. Pharmacol. Sci.; vol. 92; pp. 218-227 (2003).

Potter and Hunter; "Guanylyl cyclase-linked natriuretic peptide receptors: structure and regulation"; Minireview: The Journal of Biological Chemistry; vol. 276; No. 9; pp. 6057-6060 (Mar. 2, 2001).

Quigley; "Number of people with glaucoma worldwide"; British Journal of Ophthalmology; vol. 80; pp. 389-393 (1996).

Regoli and Barabe; "Pharmacology of Bradykinin and Related Kinins"; Pharmacological Reviews; vol. 32; No. 1; pp. 1-46 (1980).

Rizzi et la.; "Pharmacological characterisation of the first non-peptide bradykinin B2 receptor agonist FR 190997: an in vitro study on human, rabbit and pig vascular B2 receptors"; Naunyn-Schmiedeberg's Arch Pharmacol; vol. 360; pp. 361-367 (1999).

Rodella et al.; "Carbon monoxide and biliverdin prevent endothelial cell sloughing in rats with type 1 diabetes" Free Radical Biology and Medicine; vol. 40; pp. 2198-2205 (2006).

Rohen; "Why is intraocular pressure elevated in chronic simple glaucoma?"; Ophthalmol.; vol. 90; pp. 758-765 (1983).

Schroeder et al.; "Cloning and functional characterization of the ornithokinin receptor"; The Journal of Biological Chemistry; vol. 272; No. 19; pp. 12476-12481 (May 9, 1997).

Scotland et al.; "C-type natriuretic peptide in vascular physiology and disease"; Pharmacology & Therapeutics; vol. 105; pp. 85-93 (2005).

Sharif and Klimko; "Ophthalmic Agents, in Comprehensive Medicinal Chemistry II"; vol. 6; Chapter 6.12; pp. 397-320; Eds: D.J. Triggle and J.B. Taylor; Elsevier Oxford, 2007.

Sharif and Whiting; "Identification of B2-bradykinin receptors in guinea pig brain regions, spinal cord and peripheral tissues"; Neurochem Int. vol. 18; No. 1; pp. 89-96 (1991).

Sharif and Whiting; "The neuropeptide bradykinin stimulates phosphoinositide turnover in HSDM1C1 cells: B2-antagonist-sensitive responses and receptor studies"; Neurochemical Research; vol. 18; No. 12; pp. 1313-1320 (1993).

\* cited by examiner

BRADYKININ RECEPTOR AGONISTS AND USES THEREOF TO TREAT OCULAR HYPERTENSION AND GLAUCOMA

CROSS-REFERENCE TO RELATED APPLICATION

This application claims priority under 35 U.S.C. §119 to U.S. Provisional Patent Application No. 61/374,740, filed Aug. 18, 2010, the entire contents of which are incorporated herein by reference.

FIELD OF THE INVENTION

The invention relates to methods and compositions to treat ocular disorders associated with elevated intraocular pressure (IOP). More specifically the invention relates to disorders including, but not limited to, ocular hypertension and glaucoma.

BACKGROUND OF THE INVENTION

Bradykinin (BK) is an endogenous nonapeptide (H-Arg-Pro-Pro-Gly-Phe-Ser-Pro-Phe-Arg-OH; SEQ ID NO: 1) that is generated by cleavage of the precursor polypeptide (kininogen) by specific proteases (kallikriens) within numerous tissues of the body (Regoli, D. and Barabe, J. *Pharmacol. Rev.*, 32, 1-46, 1980; Hall, J. M., *Pharmacol. Ther.*, 56, 131-190, 1992; Leeb-Lundberg et al., *Pharmacol. Rev.* 57: 27-77, 2005). Certain enzymes of the kininase family degrade BK and related peptides and thus inactivate these peptides. All components of the kallkrien/kinin system, including specific receptors activated by BK and related peptides, are present in the human eye cells and tissues (Ma et al., *Exp. Eye Res.* 63: 19-26, 1996; Sharif and Xu, *Exp. Eye Res.* 63: 631-637, 1996). BK and another endogenous peptide (Lys-BK; Lys-Arg-Pro-Pro-Gly-Phe-Ser-Pro-Phe-Arg; SEQ ID NO: 2) interact with two major BK receptor-subtypes, namely $B_1$ and $B_2$ to produce their biological effects (Regoli and Barabe, *Pharmacol. Rev.*, 32, 1-46, 1980; Hall, *Pharmacol. Ther.*, 56, 131-190, 1992; Leeb-Lundberg et al., *Pharmacol. Rev.* 57: 27-77, 2005).

The $B_2$-subtype is found under normal physiological conditions, while the $B_1$-subtype is typically induced during injury or trauma (Hall, J. M., *Pharmacol. Ther.*, 56, 131-190, 1992; Leeb-Lundberg et al., *Pharmacol. Rev.* 57: 27-77, 2005). While the $B_1$-subtype has a low affinity for BK and a high affinity for Des-Arg$^9$-BK (Arg-Pro-Pro-Gly-Phe-Ser-Pro-Phe; SEQ ID NO: 3) and Lys-BK, the $B_2$-subtype has a high affinity for BK and Lys-BK but a low affinity for Des-Arg$^9$-BK. Both receptor subtypes have been cloned and shown to be coupled to G-proteins and phospholipase C and their activation results in the generation of the second messengers inositol trisphosphate ($IP_3$) and diacylglycerol (DAG) (Bhoola et al., *Pharmacol. Rev.* 44: 1080, 1992; Hall, J. M., *Pharmacol. Ther.*, 56, 131-190, 1992; Leeb-Lundberg et al., *Pharmacol. Rev.* 57: 27-77, 2005). While $IP_3$ mobilizes intracellular $Ca^{2+}$ ($[Ca^{2+}]_i$) DAG phosphorylates protein kinase C and together these events lead to the final biological response such as cell shape change, tissue contraction or fluid secretion.

Additional events ensuing from elevation of $[Ca^{2+}]_i$ include activation of nitric oxide synthase (NOS) to produce nitric oxide (NO) that in turn activates guanylyl cyclase to produce cyclic guanosine monophosphate (cGMP), and activation of cycloxygenases and/or phospholipase $A_2$ that produce endogenous prostaglandins that in turn elevate intracellular cyclic adenosine monophosphate (cAMP) (Leeb-Lundberg et al., *Pharmacol. Rev.* 57: 27-77, 2005). Activation of the $B_2$-receptor can also lead to inhibition of cAMP production in host cells transfected with the human recombinant $B_2$ receptors (Meini et al., *Brit. J. Pharmacol.* 143: 938-941, 2004). The majority of the physiological and pathological effects of BK are mediated by the $B_2$-receptor-subtype. However, pharmacological evidence has pointed to two additional BK-receptor subtypes, namely $B_3$ and $B_4$ (Hall, *Pharmacol. Ther.*, 56, 131-190, 1992; Sharma, *Gen. Pharmacol.*, 24, 267-274, 1993). $B_3$ and $B_4$ receptor subtypes are actually stimulated by certain peptide BK antagonists whereas the $B_1$ and $B_2$ subtypes are blocked by the latter antagonists (Sharma, J. N., *Gen. Pharmacol.*, 24, 267-274, 1993). While the presence of $B_3$ or $B_4$ receptor subtypes in the eye has not been investigated to-date, there is precedence for their existence in this organ since there is a robust BK-precursor and BK-generating enzyme pool in human ocular tissues and the presence of $B_1$ and $B_2$ receptors (Ma et al., *Exp. Eye Res.*, 63: 19-26, 1996).

Two new families of peptides related to BK, namely ovikinins (Schroder et al. *J. Biol. Chem.* 272: 12475-12481, 1997) and bombinakinins (Lai et al., *Biochem. Biophys. Res. Comm.* 286: 259, 2001; Lai et al. *Peptides*, 24: 199, 2003; O'Rouke et al., *Regul. Peptides* 121: 65, 2004; Lee et al., *Regul. Peptides*, 127: 207, 2005) have been discovered recently that may react with BK receptors or similar receptors. Additionally, a new receptor termed GPR100 has been recently discovered with which BK also interacts (Boels and Schaller, *Br. J. Pharmacol.* 140: 932-938, 2003).

Additional useful properties imparted by BK or BK mimetics include the lowering of mRNA of connective tissue growth factor (CTGF) (Huang et al. *Am. J. Physiol. Lung Cell Mol. Physiol.* 290: L1291-L1299, 2006), a fibrotic cytokine that has been implicated in the possible etiology of ocular hypertension by promoting deposition of collagen and fibronectin in the TM area (International Patent Application No. PCT/US2003/012521 to Fleenor et al. published Nov. 13, 2003 as WO 03/092584); BK-induced inactivation of RhoA (*Am. J. Physiol. Lung Cell Mol. Physiol.* 290: L129-L1299, 2006); BK-induced blunting of systemic hypertension (Majima et al., *Hypertension* 35: 437-442, 2000) and BK-induced increase in blood flow (Ito et al. *Br. J. Pharmacol.* 138: 225-233, 2003), which can be beneficial for retinoprotection (Tamaki et al., *J. Ocular Pharmacol. Ther.* 15: 313-321, 1999). In addition, BK has been shown to attenuate the release of proinflammatory cytokines from activated microglial cells (Noda et al., *J. Neurochem.* 101: 397-410, 2007).

There are a number of ocular conditions that are caused by, or aggravated by, damage to the optic nerve head, degeneration of ocular tissues, and/or elevated intraocular pressure (IOP). For example, "glaucomas" are a group of debilitating eye diseases that are a leading cause of irreversible blindness in the United States and other developed nations. Primary Open Angle Glaucoma ("POAG") is the most common form of glaucoma (Quigley, *Br. J. Ophthalmol.*, 80: 389-393, 1996). The disease is characterized by the degeneration of the trabecular meshwork, leading to obstruction of the normal ability of aqueous humor to leave the eye without closure of the space (e.g., the "angle") between the iris and cornea (Rohen, *Ophthalmol.* 90: 758-765, 1983; Quigley, *Br. J. Ophthalmol.*, 80: 389-393, 1996). A characteristic of such obstruction in this disease is an increased IOP, resulting in progressive visual loss and blindness if not treated appropriately and in a timely fashion. The disease is estimated to affect between 0.4% and 3.3% of all adults over 40 years old. Moreover, the prevalence of the disease rises with age to over 6% of those 75 years or older. Thus, close to 70 million are afflicted by glaucoma (Quigley, *Br. J. Ophthalmol.,* 80: 389-393, 1996).

Glaucoma affects three separate tissues in the eye. The elevated IOP associated with POAG is due to morphological and biochemical changes in the trabecular meshwork (TM), a tissue located at the angle between the cornea and iris, and ciliary muscle (CM) bundles. Most of the nutritive aqueous humor exits the anterior segment of the eye through the TM. The progressive loss of TM cells and the build-up of extracellular debris in the TM of glaucomatous eyes leads to increased resistance to aqueous outflow, thereby raising IOP. Elevated IOP, as well as other factors such as ischemia, cause degenerative changes in the optic nerve head (ONH) leading to progressive "cupping" of the ONH and loss of retinal ganglion cells and axons. The detailed molecular mechanisms responsible for glaucomatous damage to the TM, ONH, and the retinal ganglion cells are unknown.

Twenty years ago, the interplay of ocular hypertension, ischemia and mechanical distortion of the optic nerve head was heavily debated as the major factors causing progression of visual field loss in glaucoma. Since then, other factors including excitotoxicity, nitric oxide, absence of vital neurotrophic factors, abnormal glial/neuronal interplay and genetics have been implicated in the degenerative disease process. The consideration of molecular genetics deserves some discussion insofar as it may ultimately define the mechanism of cell death, and provide for discrimination of the various forms of glaucoma. Within the past 10 years, over 15 different glaucoma genes have been mapped and 7 glaucoma genes identified. However, despite such progress, the glaucomas still remain poorly understood.

Glaucoma is a progressive disease which leads to optic nerve damage and, ultimately, total loss of vision. Since there is a good correlation between IOP control and prevention/reduction of glaucomatous damage in POAG patients (Mao et al., *Am. J. Ophthalmol.* 111: 51-55, 1991), several therapeutic agents have been developed to treat ocular hypertension (Clark and Yorio, *Nature Rev. Drug Discovery,* 2: 448-459, 2003; Sharif and Klimko, Ophthalmic Agents, in *Comprehensive Medicinal Chemistry II.,* Vol. 6, Chapter 6.12, p. 297-320; Eds: D. J. Triggle and J. B. Taylor, Elsevier Oxford, 2007). Thus, it is known that elevated IOP can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics. Unfortunately, many of the drugs conventionally used to treat ocular hypertension have a variety of problems. For instance, miotics such as pilocarpine can cause blurring of vision and other visual side effects, which may lead either to decreased patient compliance or to termination of therapy. Systemically administered carbonic anhydrase inhibitors can also cause serious side-effects such as nausea, dyspepsia, fatigue, and metabolic acidosis, which can affect patient compliance and/or necessitate the termination of treatment. Another type of drug, beta-blockers, has increasingly become associated with serious pulmonary side effects attributable to their effects on beta-2 receptors in pulmonary tissue. Sympathomimetics may cause tachycardia, arrhythmia and hypertension. Recently, certain prostaglandins and prostaglandin derivatives have been described in the art as being useful in reducing IOP. Typically, however, prostaglandin therapy for the treatment of elevated IOP is attended by undesirable side-effects, such as irritation and hyperemia of varying severity and duration. There is, therefore, a continuing need for therapies that control elevated IOP associated with glaucoma without the degree of undesirable side-effects attendant to most conventional therapies.

SUMMARY OF THE INVENTION

The invention provides compounds that are bradykinin agonists. The invention further provides compositions and methods for treating and/or preventing an ocular condition associated with elevated intraocular pressure (IOP), such as ocular hypertension and glaucoma. In certain aspects, a method of the invention comprises administering to a patient a composition comprising a therapeutically effective amount of a compound of Formula 1 in a pharmaceutically acceptable ophthalmic vehicle.

Specific preferred embodiments of the invention will become evident from the following more detailed description of certain preferred embodiments and the claims.

DETAILED DESCRIPTION OF THE INVENTION

There are conflicting reports in the literature as to the functions and involvement of BK in the modulation of IOP in various animal models. For example, while intravenous infusion of BK apparently lowered IOP (Chiang et al., *Arch. Int. Pharmacodyn. Ther.* 207: 131-138, 1974; Funk et al., *Graefes Arch. Clin. Exp. Ophthalmol.* 223: 145-149, 1985), injection of BK directly into the anterior chamber of the eye raised IOP and caused intense miosis (Cole and Ungar, *Ophthalmic Res.* 6: 308-314, 1974; Yokahama et al., *Jpn. J. Ophthalomol.* 34: 245-255, 1990) and increased both aqueous humor inflow and outflow (Green and Elijah, *Exp. Eye Res.* 33: 239-245, 1981). Furthermore, BK either had no effect on aqueous humor outflow (no ciliary muscle retrodisplacement) or decreased outflow (with ciliary muscle retrodisplacement) in cynomolgus monkey eyes upon injection of BK into the eye anterior chamber (Kaufman et al. *Exp. Eye Res.* 35: 191-199, 1982). Additionally, in perfused human and bovine anterior eye segments BK decreased outflow facility (Llobet et al., *Invest. Ophthalmol. Vis. Res.,* 40: 113-125, 1999), while another group has recently demonstrated an apparent increase in outflow in bovine eyes (Webb et al., *J. Ocular Pharmacol. Ther.* 22: 310-316, 2006). Such conflicting data coupled with an existing patent (U.S. Pat. No. 6,500,831) that contemplated the need for BK antagonists to elicit ocular hypotension has resulted in confusion about the potential role of endogenous BK and related peptides and their receptors in the modulation of IOP and ocular hypertension.

Some obvious drawbacks and reasons for the lack of consistent observations noted above are probably related to species differences in the effects of BK on IOP changes and on the fact that BK is a labile peptide that can easily and rapidly be inactivated by kininases and other proteases when it comes into contact with body fluids (Hall, *Pharmacol. Ther.,* 56, 131-190, 1992).

In certain embodiments, the invention provides compounds that can be represented by the general Formula 1:

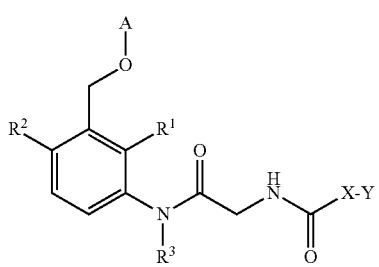

(Formula 1)

wherein,
$R^1$, $R^2$ independently=—$CH_3$ or —Cl;
$R^3$=$C_1$-$C_3$alkyl;

A is:

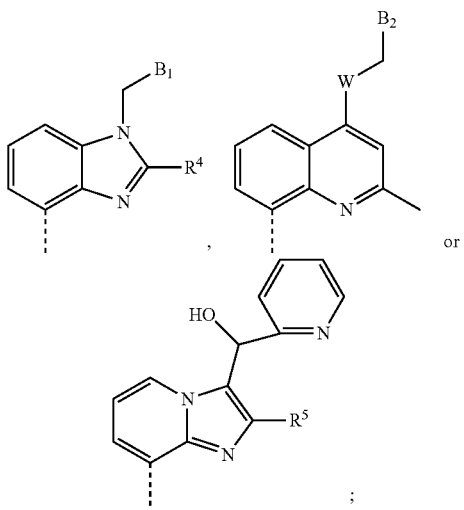

$R^4$=—$OR^5$, —$NR^7R^{10}$ or —$R^5$;
$R^5$=$C_1$-$C_3$ alkyl;
X=—$(CH_2)_n$— or —$CF_2CH_2$—;
n=1-3;
Y is:

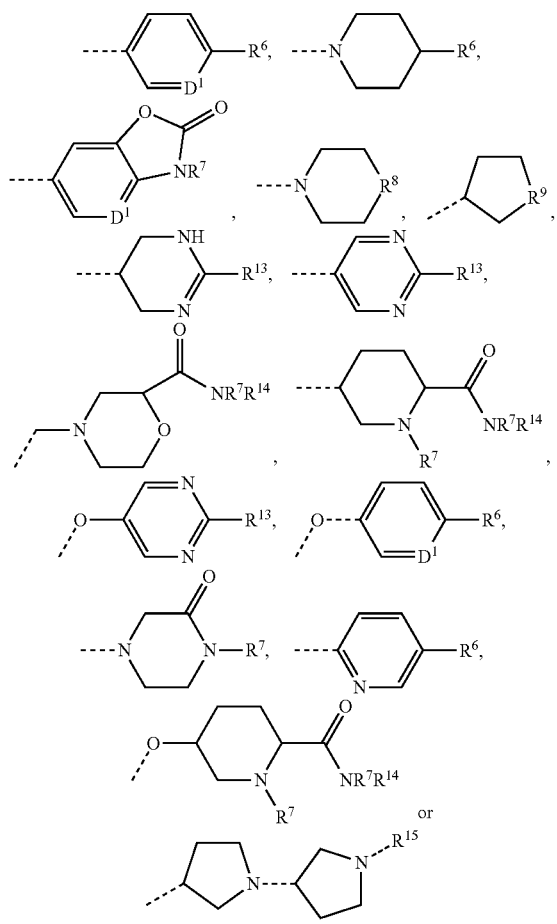

$D_1$=N, CH, $CR^5$, or $COR^5$;
$R^6$=—C(O)$OR^{10}$, —N($R^{10}$)C(O)$R^{11}$, —N($R^{10}$)S($O_2$)$R^{11}$, —C(O)N($R^{10}$)($R^{11}$), —N($R^{10}$)C(O)$OR^{11}$, —$NR^{10}$C(O) $NR^7R^{11}$, $NR^{10}R^{12}$, or —$(CH_2)_mNR^{10}R^{12}$;
$R^7$=H or $C_1$-$C_3$ alkyl;

$R^8$=O, NC(O)$R^{11}$, NS($O_2$)$R^{11}$, NC(O)$OR^{11}$, NC(O)$NR^7R^{11}$, or $NR^{11}$;
$R^9$=NC(O)$R^{11}$, NS($O_2$)$R^{11}$, NC(O)$OR^{11}$, NC(O)$NR^7R^{11}$, or $NR^{11}$;
$R^{10}$=H or $C_1$-$C_3$ alkyl;
$R^{11}$=H, $C_1$-$C_4$ alkyl, or —$(CH_2)_p$—Z;
$R^{12}$=H, $C_1$-$C_3$ alkyl, or —C(O)$R^7$;
m=1-3; p=2-4;
Z=—OH or —$OR^{12}$;
$R^{13}$=—N($R^{10}$)C(O)$R^{11}$, —N($R^{10}$)S($O_2$)$R^{11}$, —C(O)N($R^{10}$)($R^{11}$), —N($R^{10}$)C(O)$OR^{11}$, or —$NR^{10}$C(O)$NR^7R^{11}$;
$R^{14}$=—H, —$CH_3$, or -cyclopropyl;
$R^{15}$=—H, $C_1$-$C_3$ alkyl, C(O)$OR^{11}$, —C(O)N($R^{10}$)($R^{11}$), or —$(CH_2)_mNR^{10}R^{12}$;
W=—O— or —NH—;
$B_1$ is:

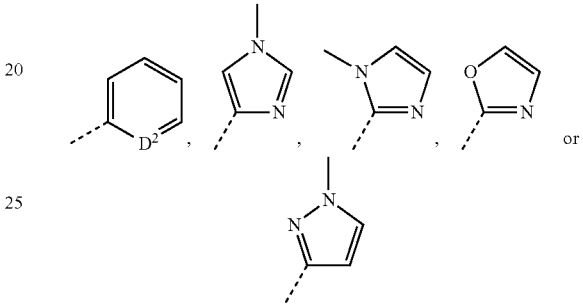

$D^2$=N, CH or CF;
; and
$B_2$ is:

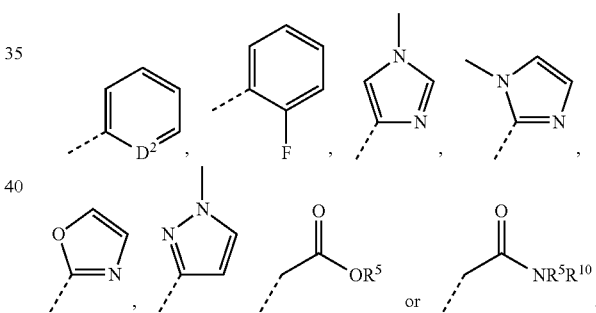

$D^2$=N, CH or CF;
Preferred compounds of Formula 1 are those in which:
$R^1$, $R^2$ independently=—$CH_3$ or —Cl;
$R^3$=$C_1$-$C_3$ alkyl;
A is:

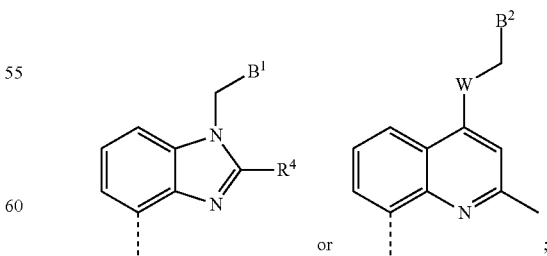

$R^4$=—$OR^5$ or —$NR^7R^{10}$;
$R^5$=$C_1$-$C_3$ alkyl
X=—$(CH_2)_n$—;
n=1-3;

Y is:

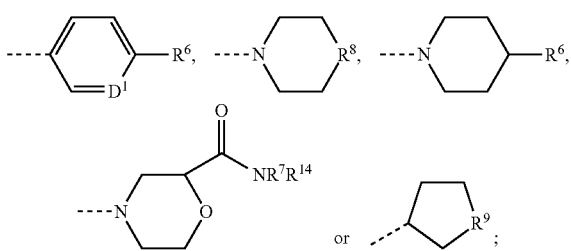

D₁=N, CH, CR⁵, or COR⁵;
R⁶=—N(R¹⁰)C(O)R¹¹, —C(O)N(R¹⁰)(R¹¹), or —NR¹⁰C(O)OR¹¹;
R⁷=—H or C₁-C₃ alkyl;
R⁸=—O—, —NC(O)R¹¹, —NC(O)OR¹¹, or —NC(O)NR⁷R¹¹;
R⁹=NC(O)R¹¹ or NC(O)OR¹¹;
R¹⁰=—H or C₁-C₃ alkyl;
R¹¹=—H, C₁-C₄ alkyl or —(CH₂)ₚ—Z;
R¹⁴=—H, —CH₃, or -cyclopropyl;
p=2-4
Z=—OH or —OR¹²
W=—O— or —NH—;
B₁ is:

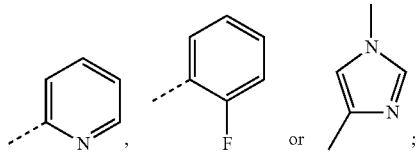

and
B²=B¹.

Other preferred compounds of Formula 1 are:
Compound 7, 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperazine-1-carboxamide;
Compound 8, 3-(4-acetamidopiperidin-1-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide;
Compound 28, 3-(4-acetamidophenyl)-N-(2-((2,4-dichloro-3-(((2-methyl-4-(pyridin-2-ylmethoxy)quinolin-8-yl)oxy)methyl)phenyl)(methyl)amino)-2-oxoethyl)propanamide;
Compound 32, 3-(6-acetamidopyridin-3-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide;
Compound 33, 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylbenzamide;
Compound 34, (S)-tert-butyl 3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)carbamoyl)pyrrolidine-1-carboxylate;
Compound 44, 4-(2-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2-oxoethyl)-N-methylmorpholine-2-carboxamide;
Compound 56, 4-(3-((2-((3-(((2-methoxy-1-(pyridin-2-ylmethyl)-1H-benzo[d]imidazol-4-yl)oxy)methyl)-2,4-dimethylphenyl)(methyl)amino)-2-oxoethyl)amino)-3-oxopropyl)-N-methylbenzamide;
Compound 64, 5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpicolinamide;
Compound 74, 3-(6-(2-aminoacetamido)pyridin-3-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide; or
Compound 78, 4-(3-((2-((2,4-dichloro-3-(((2-methoxy-1-((1-methyl-1H-imidazol-4-yl)methyl)-1H-benzo[d]imidazol-4-yl)oxy)methyl)phenyl)(methyl)amino)-2-oxoethyl)amino)-3-oxopropyl)-N-methylbenzamide.

In certain embodiments, a BK agonist of the invention is a compound shown in Table 1.

TABLE 1

| Structure | Compound # |
|---|---|
| (structure) | 1 |
| (structure) | 2 |
| (structure) | 3 |

TABLE 1-continued
| Structure | Compound # |
|---|---|
| 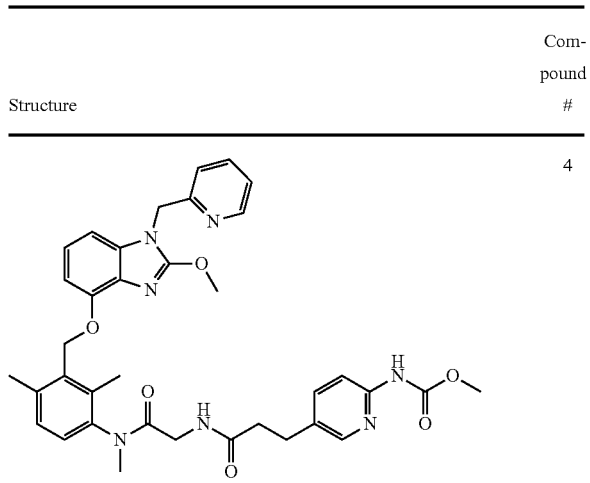 | 4 |
| 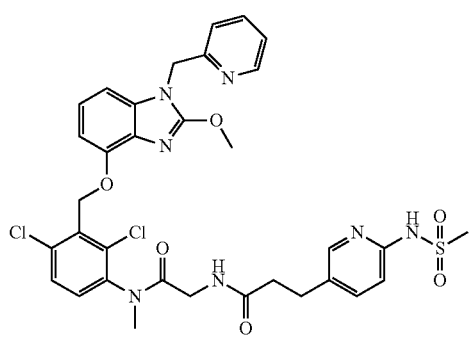 | 5 |
| 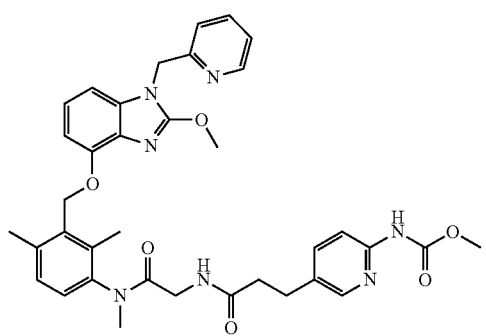 | 6 |
| 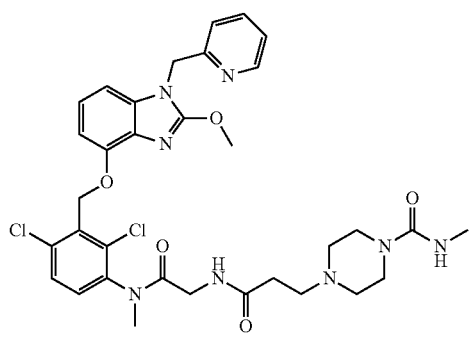 | 7 |
| 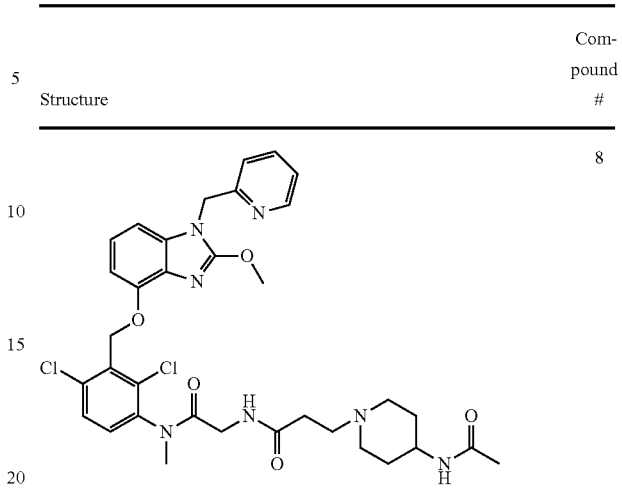 | 8 |
| 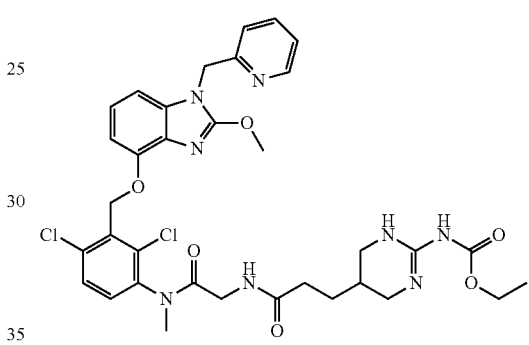 | 9 |
| 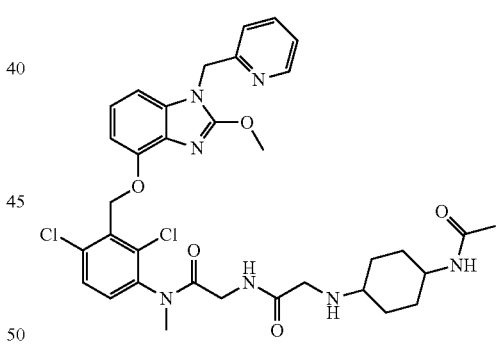 | 10 |
| 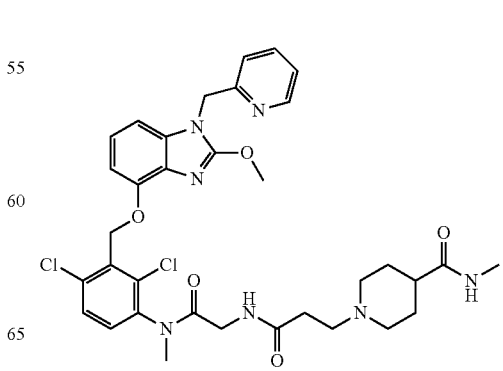 | 11 |

TABLE 1-continued
| Structure | Compound # |
|---|---|
| 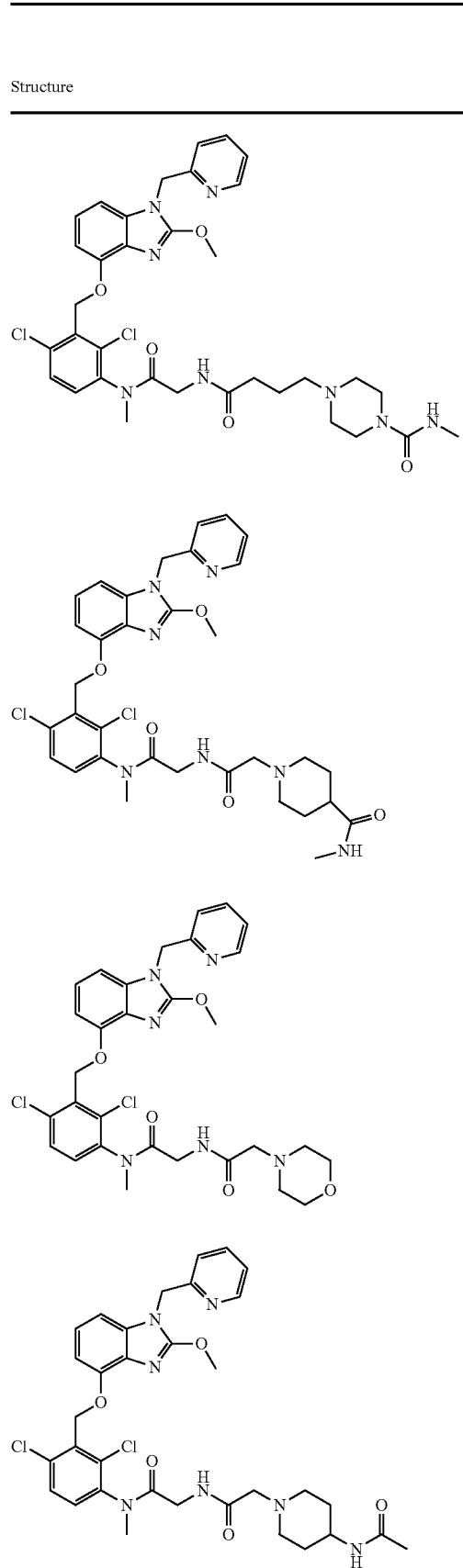 | 12 |
| 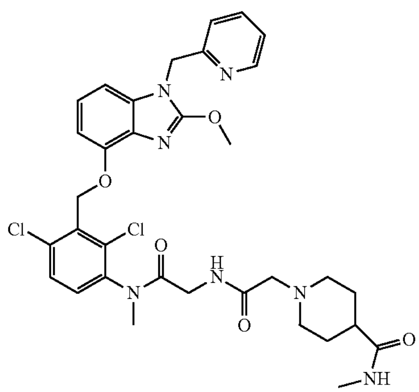 | 13 |
| 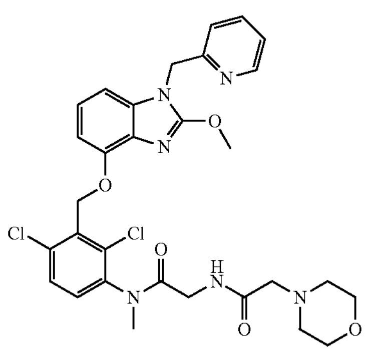 | 14 |
| 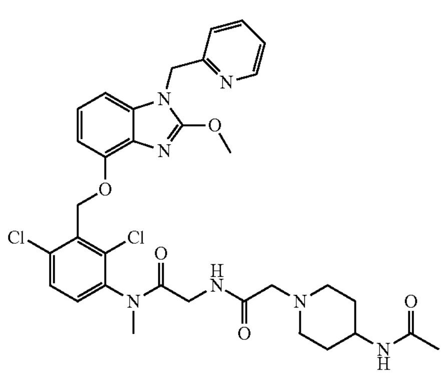 | 15 |
TABLE 1-continued
| Structure | Compound # |
|---|---|
| 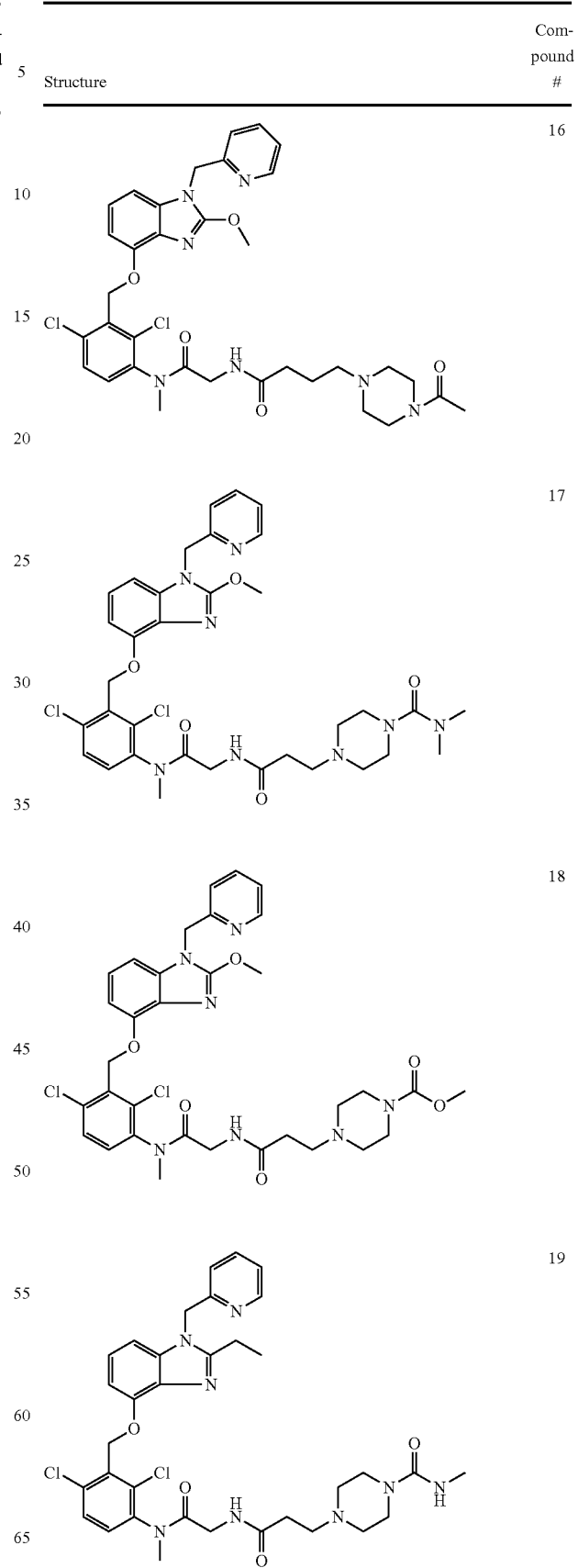 | 16 |
| 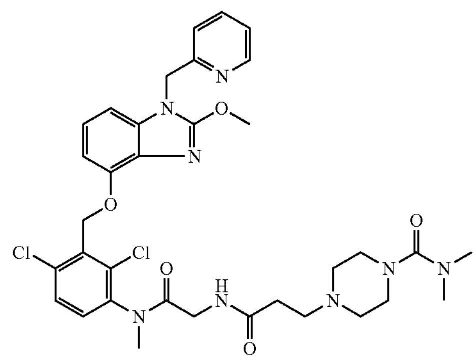 | 17 |
| 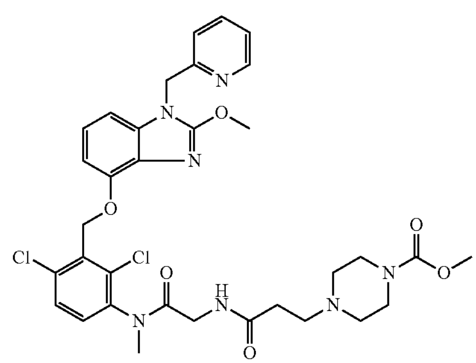 | 18 |
| 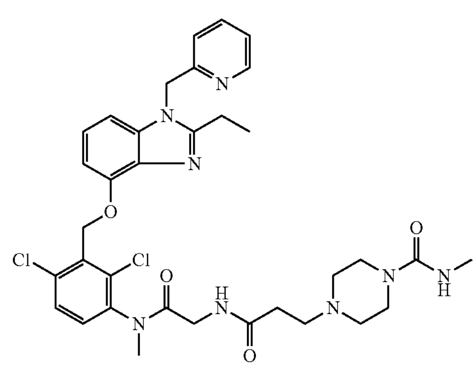 | 19 |

TABLE 1-continued

| Structure | Compound # |
|---|---|
| (structure) | 20 |
| (structure) | 21 |
| (structure) | 22 |
| (structure) | 23 |
| (structure) | 24 |
| (structure) | 25 |
| (structure) | 26 |
| (structure) | 27 |

TABLE 1-continued
| Structure | Compound # |
|---|---|
| 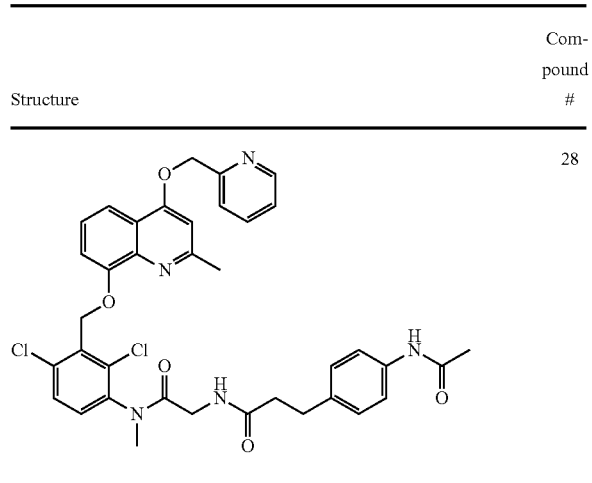 | 28 |
| 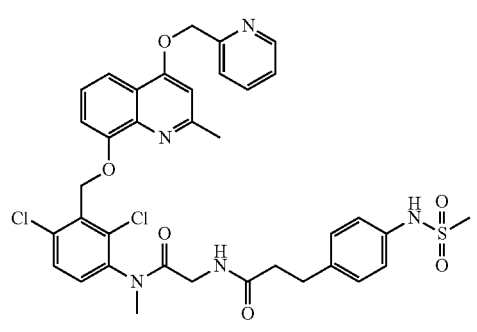 | 29 |
| 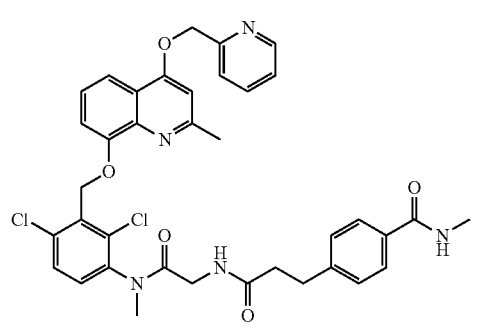 | 30 |
| 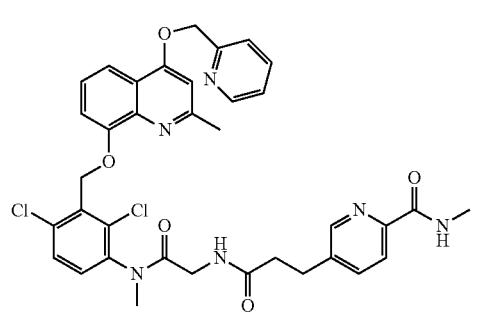 | 31 |
TABLE 1-continued
| Structure | Compound # |
|---|---|
| 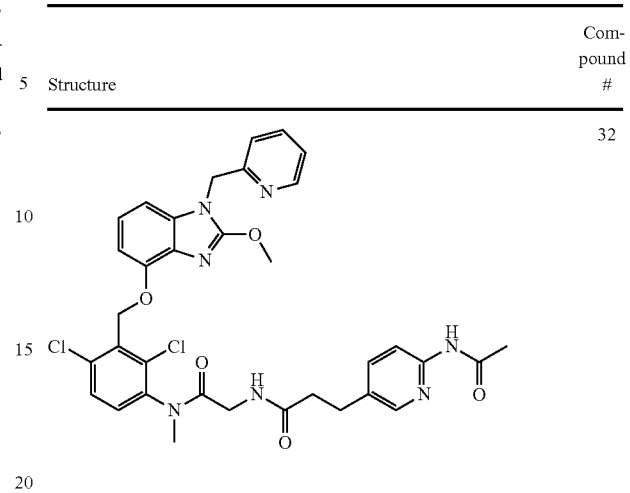 | 32 |
| 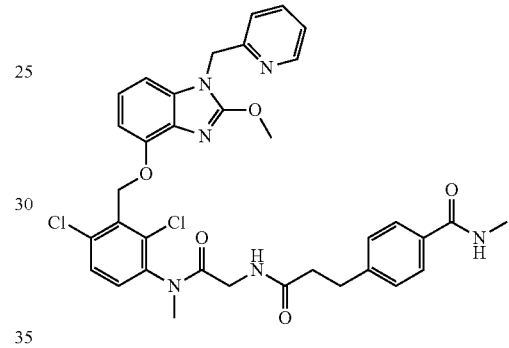 | 33 |
| 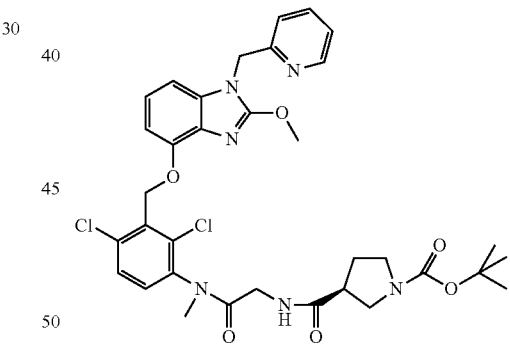 | 34 |
| 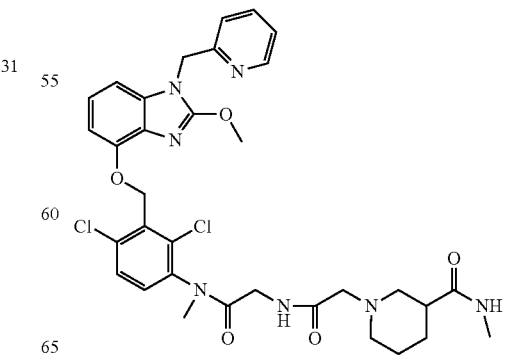 | 35 |

TABLE 1-continued
| Structure | Compound # |
|---|---|
| 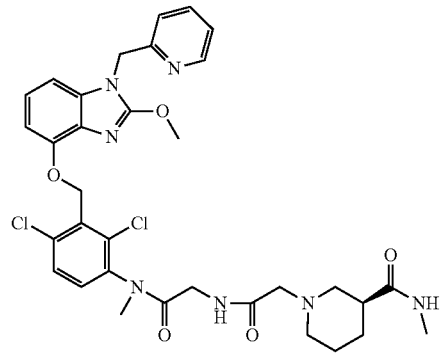 | 36 |
| 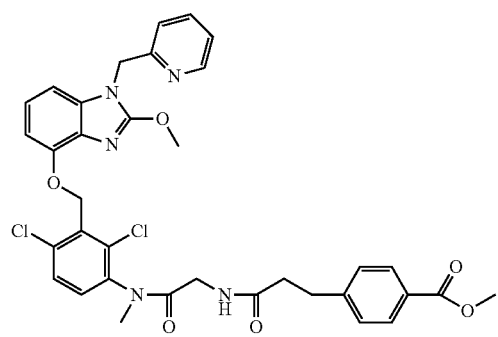 | 37 |
| 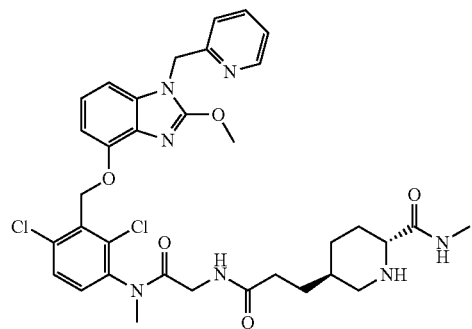 | 38 |
| 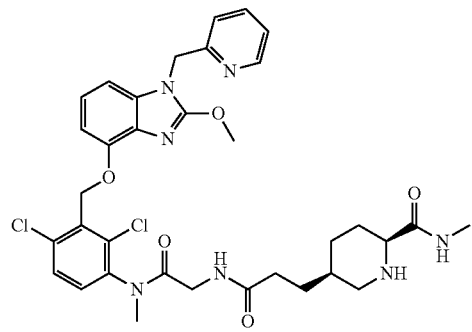 | 39 |
TABLE 1-continued
| Structure | Compound # |
|---|---|
| 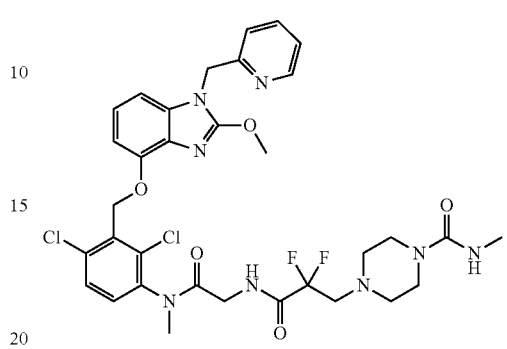 | 40 |
| 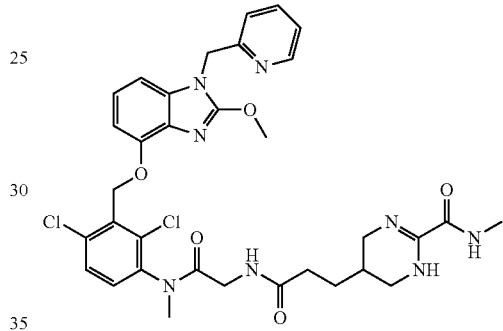 | 41 |
| 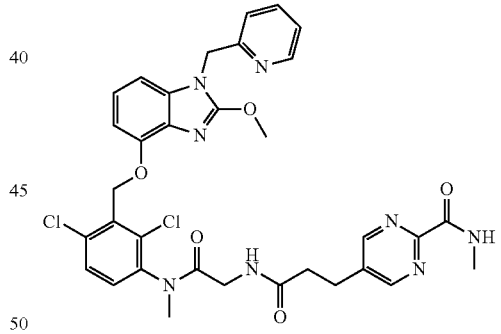 | 42 |
| 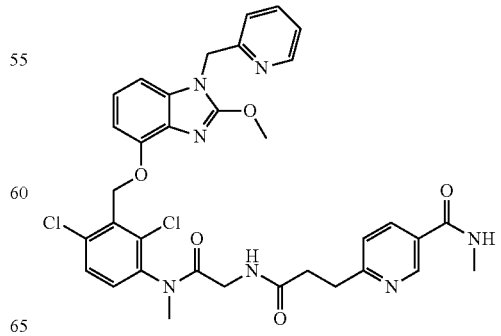 | 43 |

TABLE 1-continued
| Structure | Compound # |
|---|---|
| 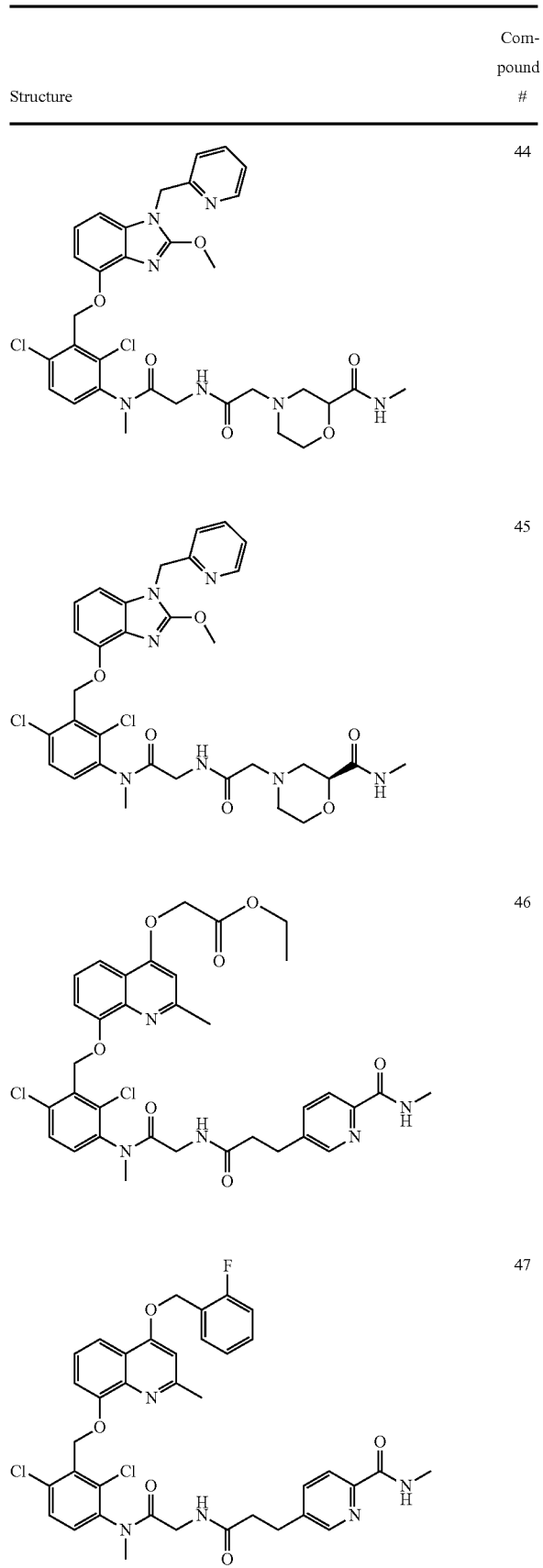 | 44 |
| 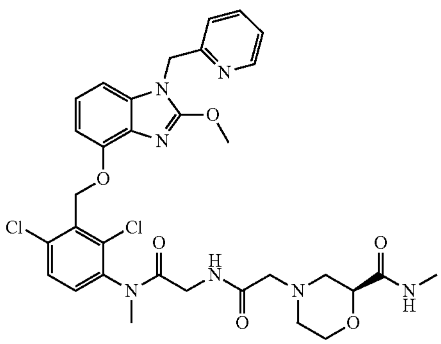 | 45 |
| 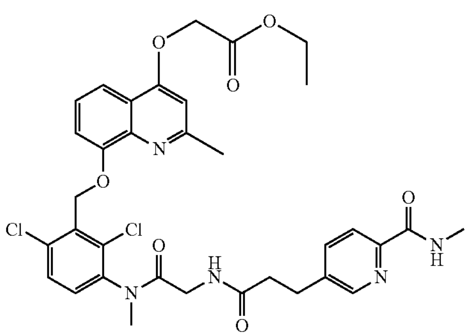 | 46 |
| 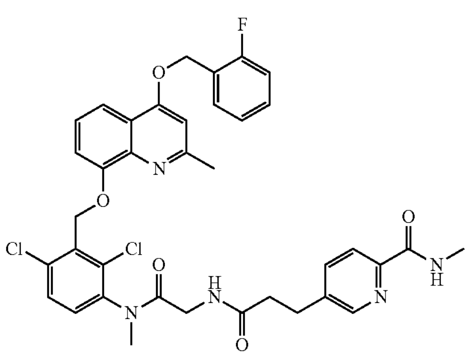 | 47 |
TABLE 1-continued
| Structure | Compound # |
|---|---|
| 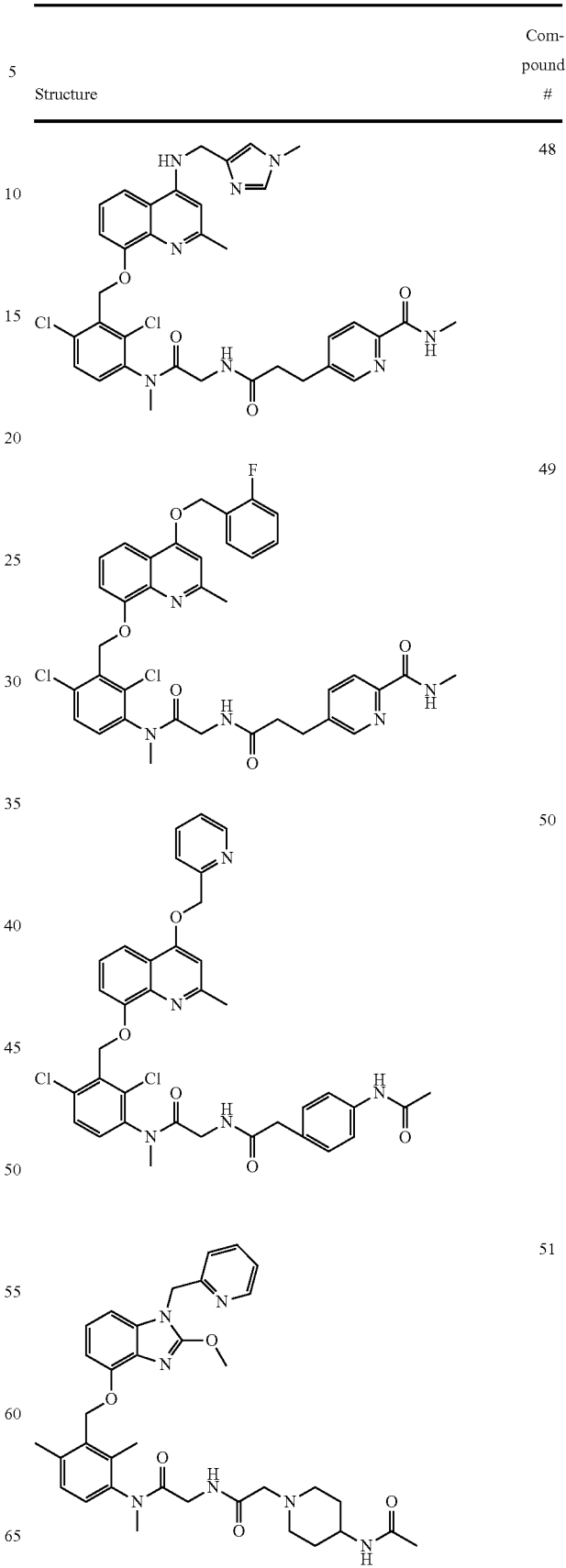 | 48 |
| | 49 |
| | 50 |
| | 51 |

TABLE 1-continued
| Structure | Compound # |
|---|---|
| 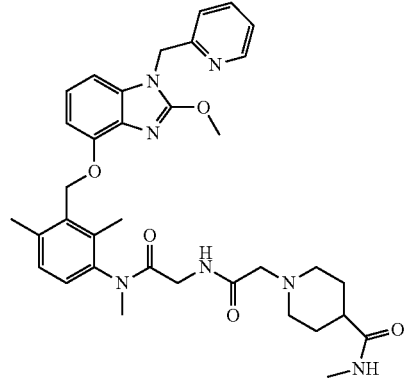 | 52 |
| 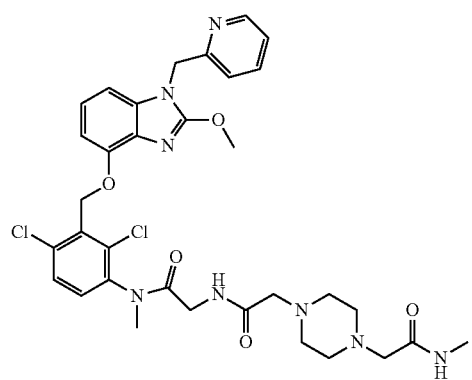 | 53 |
| 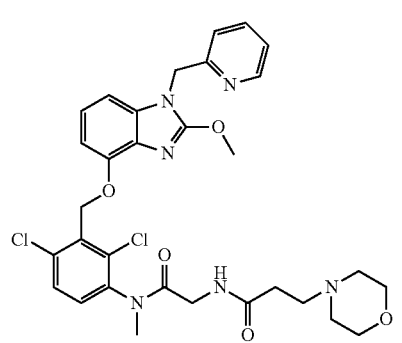 | 54 |
| 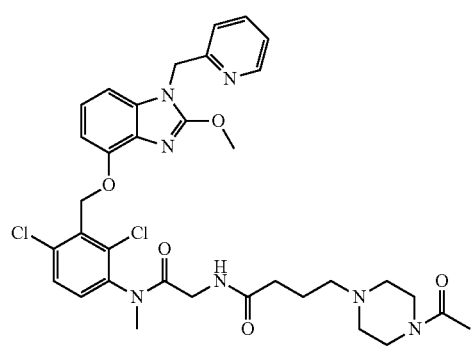 | 55 |
TABLE 1-continued
| Structure | Compound # |
|---|---|
| 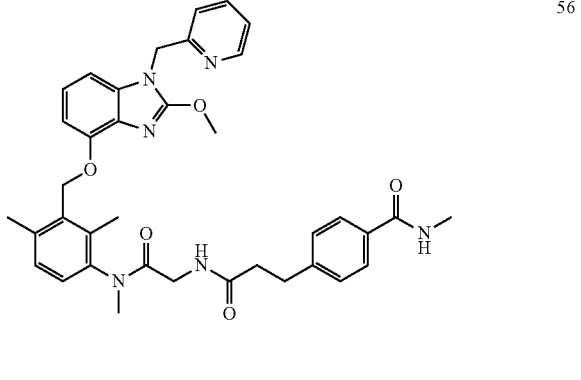 | 56 |
| 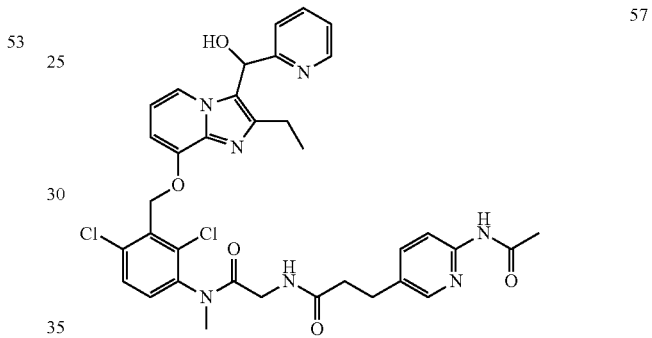 | 57 |
| 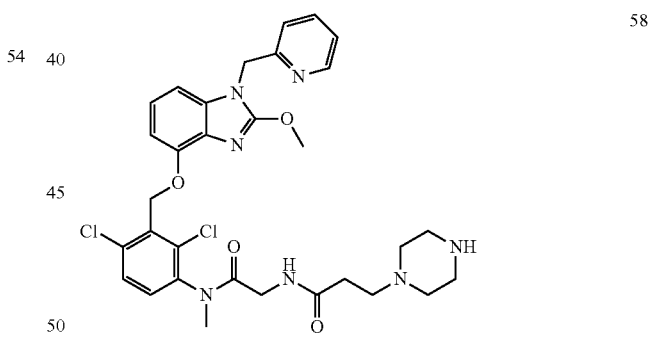 | 58 |
| 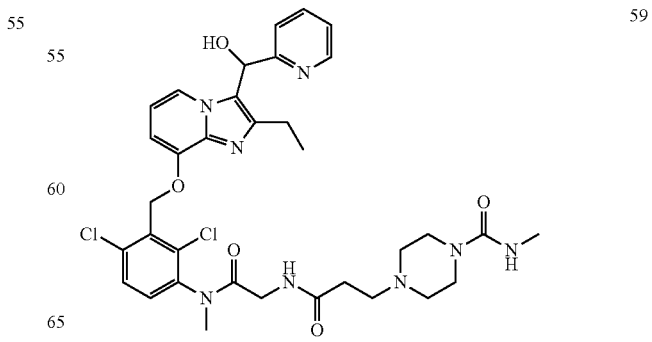 | 59 |

TABLE 1-continued

| Structure | Compound # |
|---|---|
| (structure) | 60 |
| (structure) | 61 |
| (structure) | 62 |
| (structure) | 63 |
| (structure) | 64 |
| (structure) | 65 |
| (structure) | 66 |
| (structure) | 67 |

TABLE 1-continued
| Structure | Compound # |
|---|---|
| 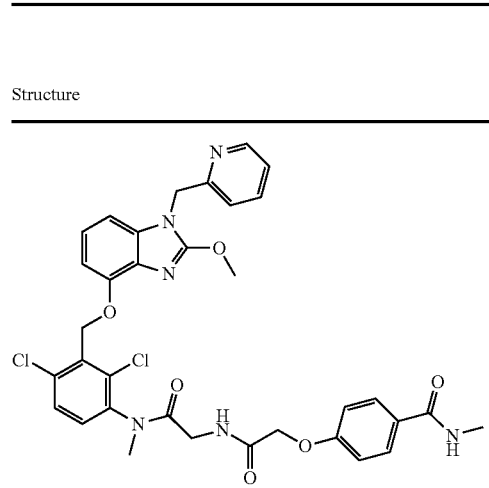 | 68 |
| 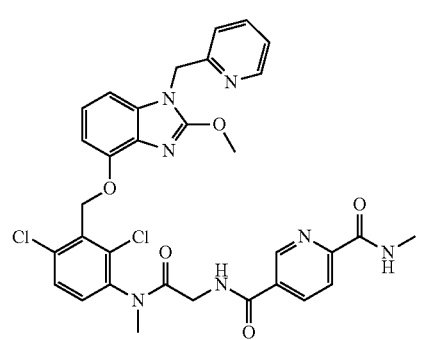 | 69 |
| 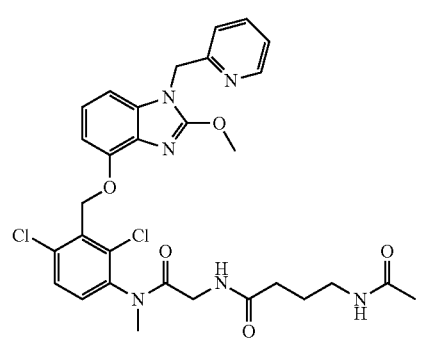 | 70 |
| 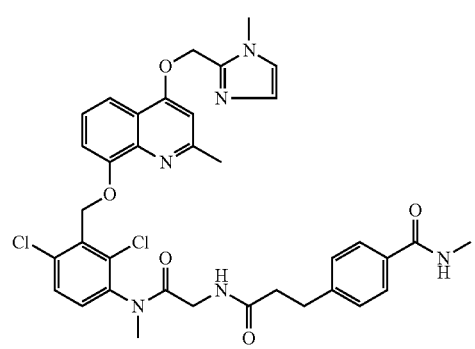 | 71 |
TABLE 1-continued
| Structure | Compound # |
|---|---|
| 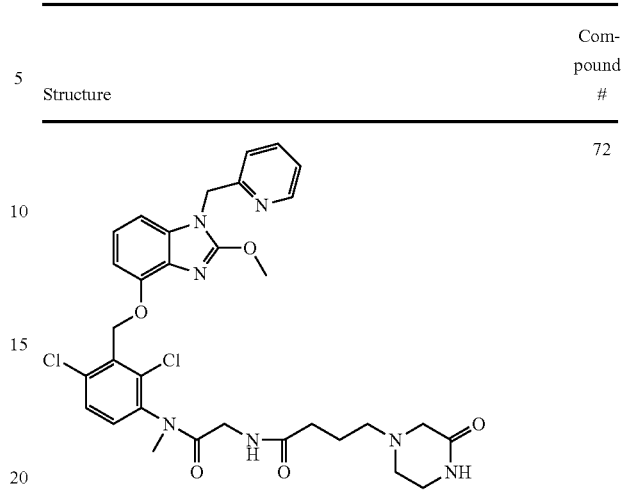 | 72 |
| 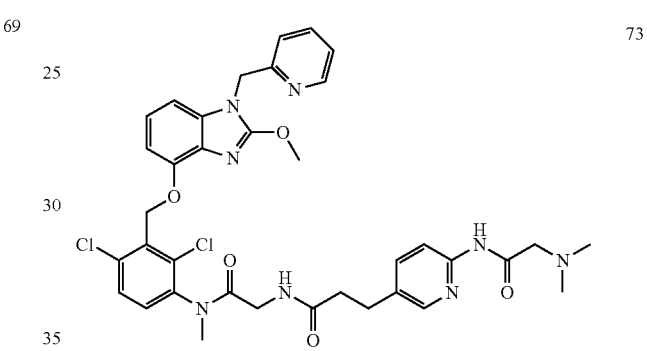 | 73 |
| 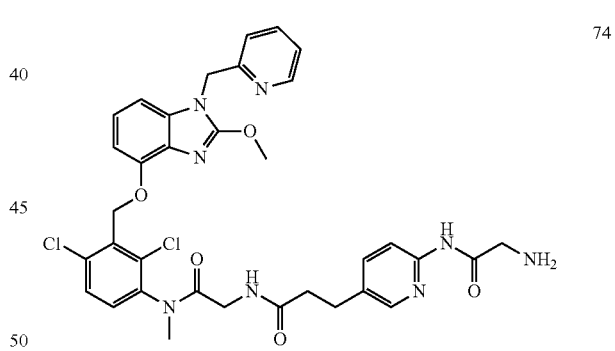 | 74 |
| 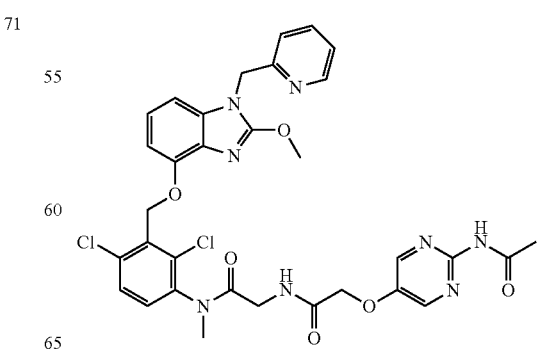 | 75 |

TABLE 1-continued

| Structure | Compound # |
|---|---|
| 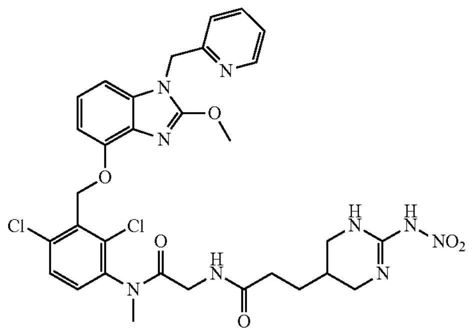 | 76 |
| 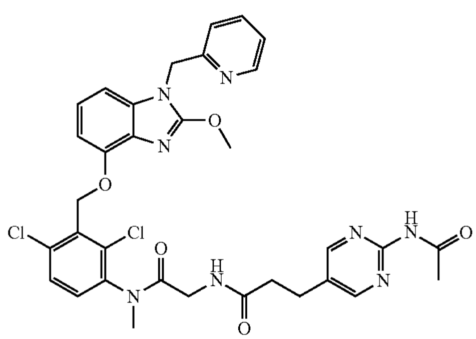 | 77 |
| 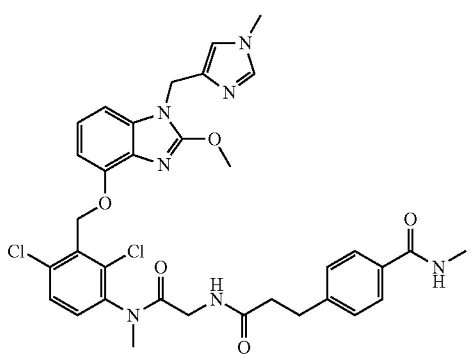 | 78 |
| 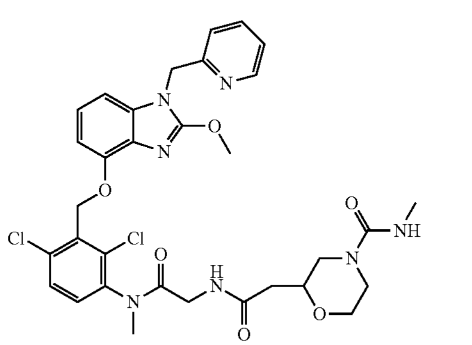 | 79 |
| | 80 |
| | 81 |
| | 82 |
| | 83 |

TABLE 1-continued
| Structure | Compound # |
|---|---|
| 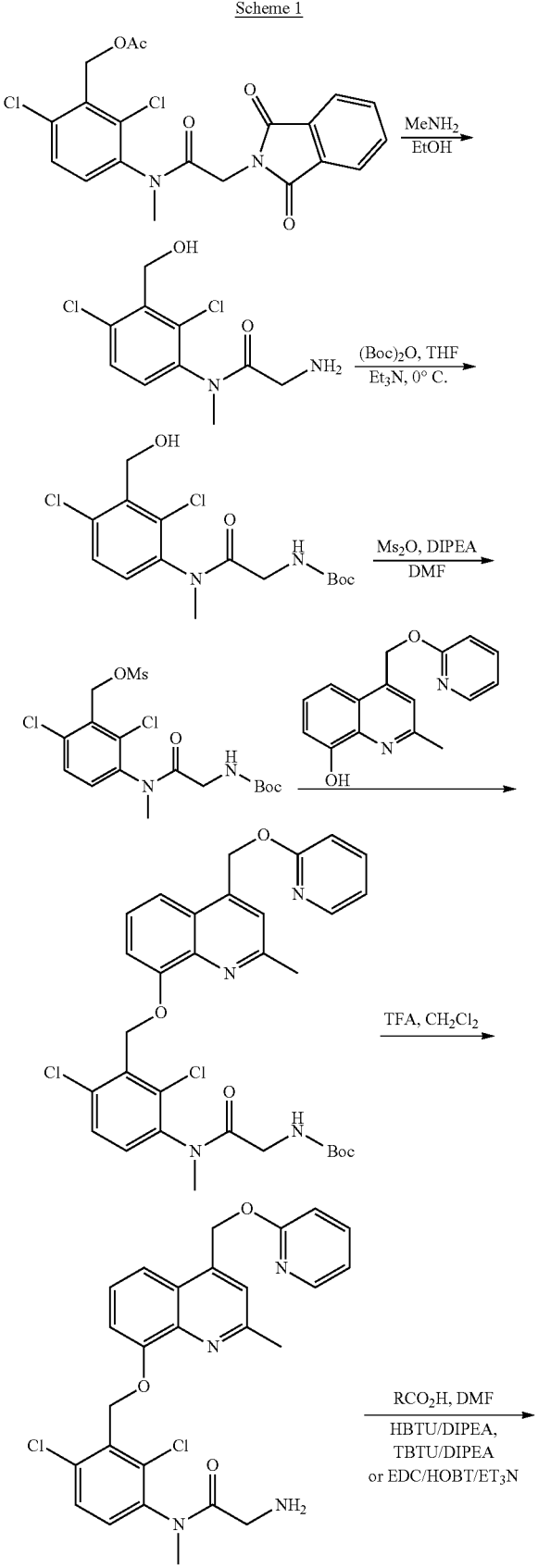 | 84 |
| 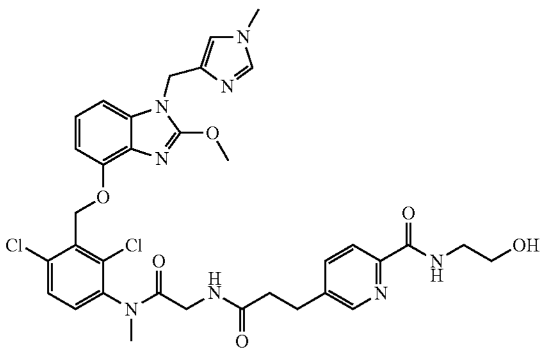 | 85 |
| 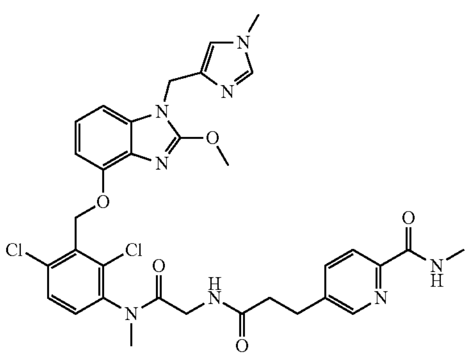 | 86 |
| 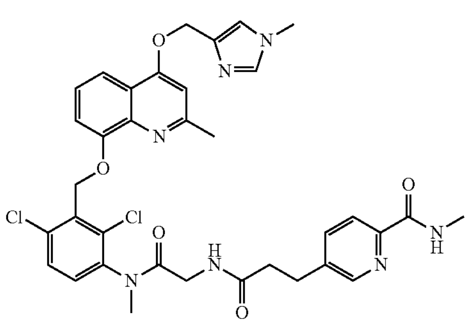 | 87 |
As used herein, a "bradykinin agonist" or "BK agonist" refers to a compound of Formula 1.
A BK agonist of the invention can be generated, for example, as described in the following Schemes.
Scheme 1

Scheme 2
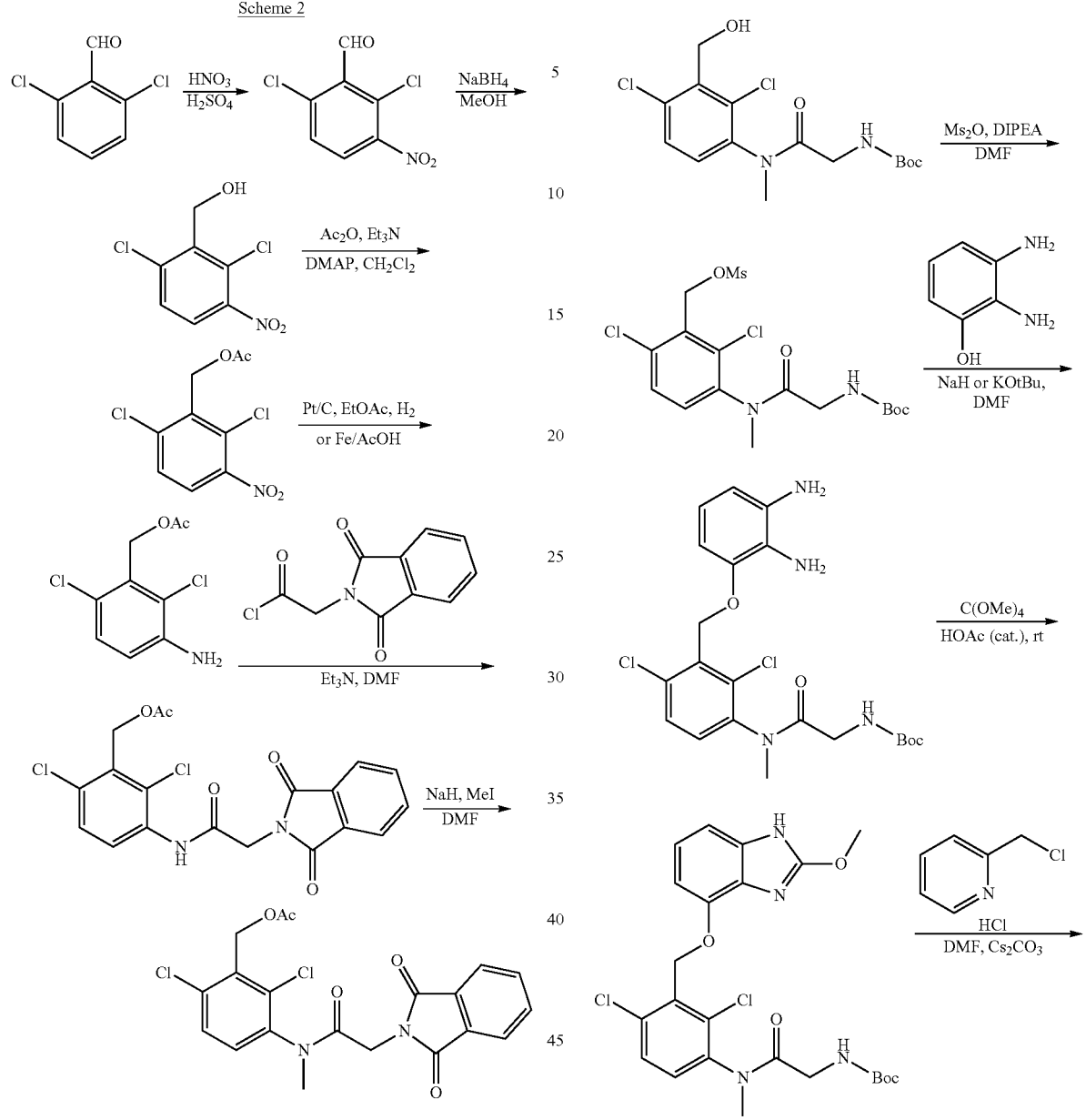
Scheme 3
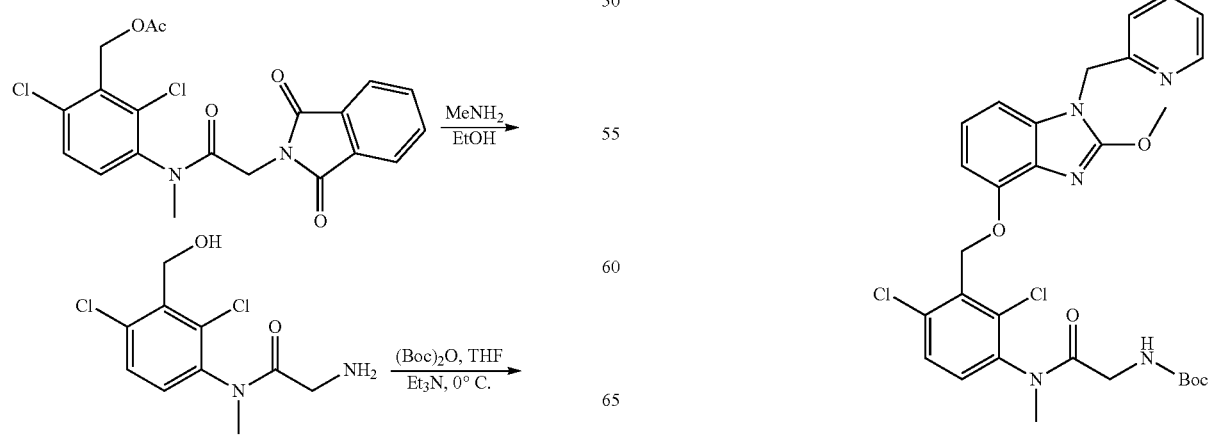

Scheme 4
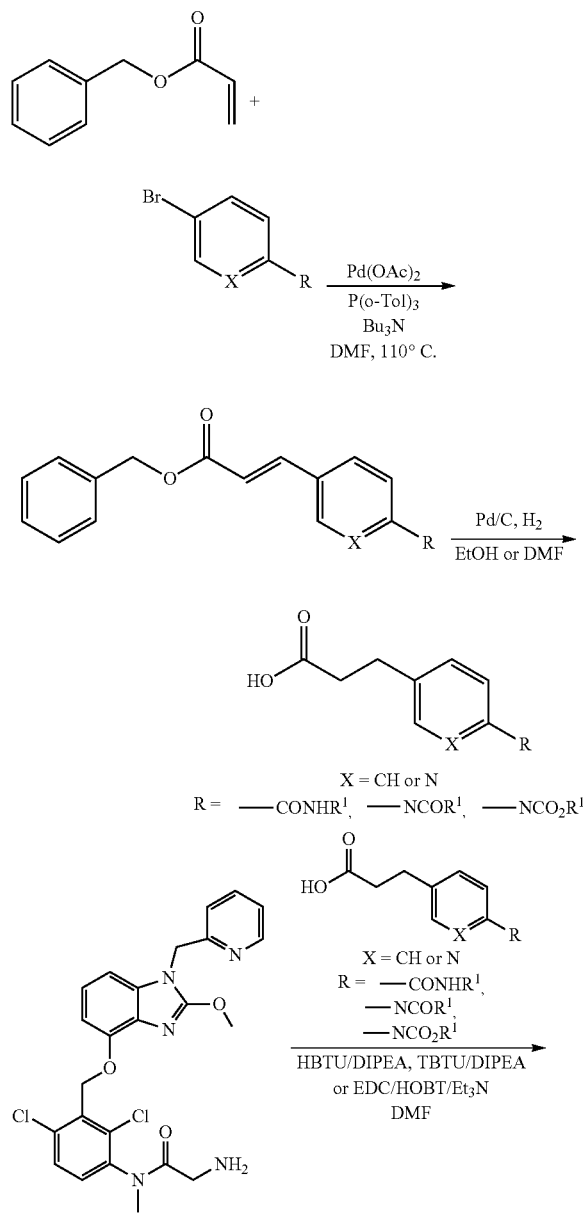
Scheme 5
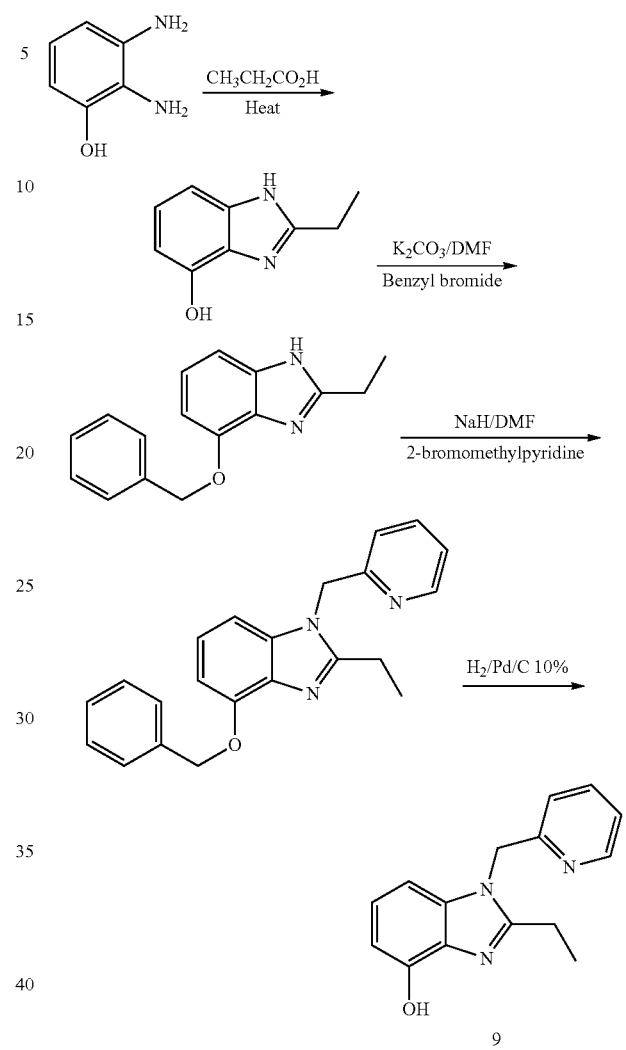
Scheme 6
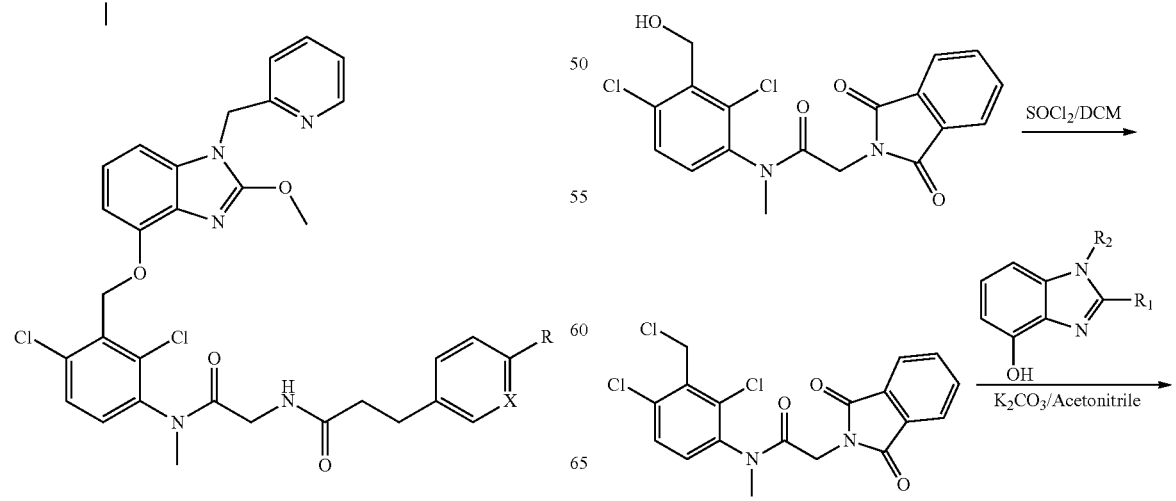

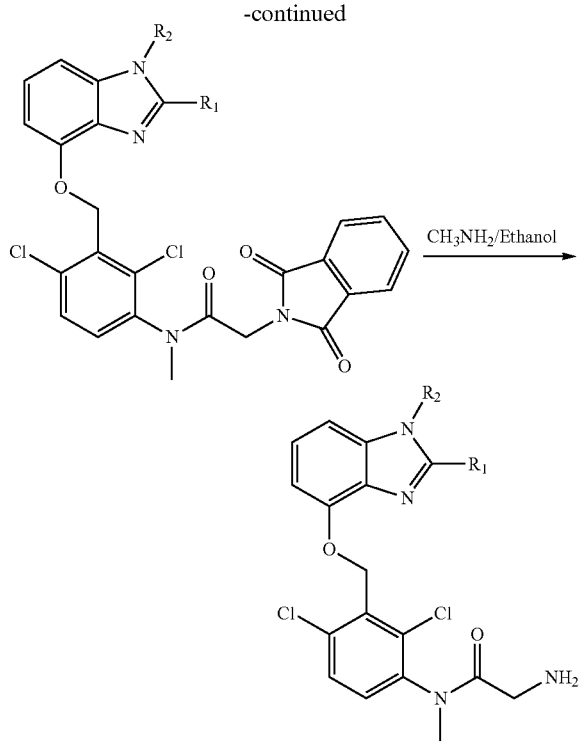

Scheme 7

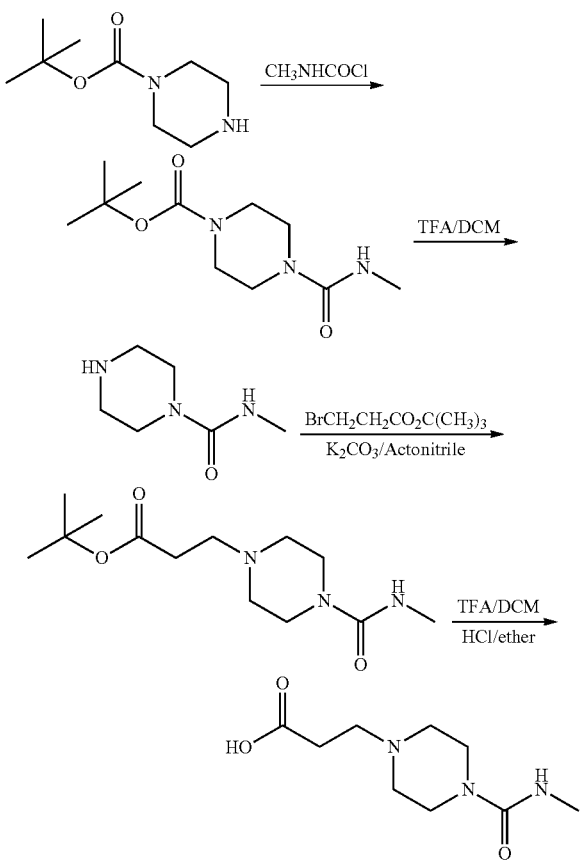

The invention provides methods for treating or preventing ocular hypertension and ocular diseases associated with elevated intraocular pressure (IOP), such as glaucoma. In certain embodiments, the methods of the invention comprise the step of administering a pharmaceutical composition to the eye of a patient, wherein the composition comprises a therapeutically effective amount of a non-peptide bradykinin (BK) agonist and a pharmaceutically acceptable ophthalmologic carrier.

In particular embodiments, the invention provides pharmaceutical compositions comprising at least one non-peptide BK agonist. The pharmaceutical compositions of the invention can be used to control IOP in a patient, thereby treating or preventing ocular hypertension and diseases associated with elevated IOP, such as glaucoma. As used herein, the phrases "control IOP" and "controlling IOP" refer to the ability of a pharmaceutical composition of the invention to prevent an increase of a patient's IOP and/or to lower a patient's existing IOP. Thus, a pharmaceutical composition of the invention can be used, for example, to prevent ocular hypertension from progressing into an ocular disease associated with elevated IOP, such as glaucoma. Alternatively, a pharmaceutical composition of the invention can be used, for example, to treat a patient who has been diagnosed with glaucoma, thereby reducing the patient's elevated IOP and improving and/or restoring vision to the patient.

As used herein, the term "patient" includes human and animal subjects.

The term "therapeutically effective amount" refers to the amount of a pharmaceutical composition of the invention determined to produce a therapeutic response in a mammal. Such therapeutically effective amounts are readily ascertained by one of ordinary skill in the art and using methods as described herein.

As used herein, the term "pharmaceutically acceptable ophthalmic carrier" refers to those carriers that cause at most, little to no ocular irritation, provide suitable preservation if needed, and deliver one or more non-peptide BK agonists of the present invention in a homogenous dosage.

The terms "pharmaceutical composition" and "composition" as used herein refer to a composition comprising a pharmaceutically acceptable ophthalmologic carrier, excipient, or diluent and a BK agonist as described herein that is capable of inducing a desired therapeutic effect (e.g. lowering IOP or preventing an increase in IOP) when properly administered to a patient.

Compounds of the invention may exist as one or more stereoisomers and mixtures thereof, wherein asymmetric or chiral centers are present. Stereoisomers include enantiomers and diastereomers, and mixtures of enantiomers or diastereomers.

Various geometric isomers and mixtures thereof may exist in the compounds of the present invention, resulting from the disposition of substituents around a carbon-carbon double bond, a carbon-nitrogen double bond, a cycloalkyl group, or a heterocycle group.

All such isomers and mixtures thereof are specifically included within the scope of this invention. Individual stereoisomers of compounds of the present application may be prepared synthetically using techniques well known to those of skill in the art.

It is to be understood that compounds disclosed herein may exhibit the phenomenon of tautomerism.

Thus, the formulae drawings depicting chemical structures of certain compounds of the invention can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Furthermore, certain embodiments of the present invention comprise pharmaceutically acceptable salts of compounds according to Formula I. Pharmaceutically acceptable salts comprise, but are not limited to, soluble or dispersible forms of compounds according to Formula I that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

In order to reduce possible ocular side-effects such as redness (hyperemia) or irritation, the compositions of this invention can be converted to suitable prodrugs by incorporation of acceptable functional groups to the non-peptide BK agonists, such that the prodrug would readily and rapidly penetrate the cornea and be then hydrolyzed to release the active species of the conjugate molecule into the aqueous humor. In this way, the residence time for the drug on the ocular surface is reduced along with the reduced extent and duration of ocular surface side-effects. A prodrug can be identified and generated using techniques well known to those skilled in the art (e.g. for ocular hypotensive prostaglandins isopropyl esters or amides are known; Stjernschantz et al. *Adv. Prostaglandin. Thrombox. Leukotr. Res.*, 23: 513-518, 1995; Woodward et al. *J. Pharmacol. Exp. Ther.* 305: 772-785, 2003).

The compositions of the invention can be administered to an eye of a patient as solutions, suspensions, or emulsions (dispersions) in a suitable ophthalmic carrier. For example, the compositions can be delivered topically to the eye in the form of drops, sprays, or gels. Alternatively, the compositions can be administered by injection (e.g., intravitreal, intracameral, intraocular, intraorbital, and/or subconjunctival and/or sub-tenon injection). The compositions can also be administered by means of an implantable device, which can be attached, for example, to a subconjunctival, intracameral, or intravitreal region of the eye.

In preparing compositions for topical administration, the BK agonists are generally formulated from about 0.00005 to about 1.0 percent by weight (wt %). The BK agonists are preferably formulated between about 0.0003 to about 0.3 wt % and, more preferably, between about 0.0005 and about 0.03 wt %. In a particular embodiment, the formulation is about 0.003% or 0.005%. In general, the compositions will be solutions, having a pH between about 4.5 and about 7.4. While the precise regimen is left to the discretion of the clinician, the resulting formulation(s) are preferably administered by placing one drop of each solution(s) in each eye one to four times a day, or as directed by the clinician.

Other ingredients which may be desirable to use in the ophthalmic preparations of the present invention include preservatives, surfactants (such as tyloxapol), co-solvents (such as polyethylene glycol, including, but not limited to, PEG 400), buffers, tonicity building agents, viscosity building agents and penetration enhancers. Viscosity building agents, such as xanthan gum, carbomer, hydroxymethyl cellulose, hydroxyethyl cellulose, methylcellulose, polyvinylpyrrolidine, a polymer matrix such as CAPA4101 or the like, may be added to the compositions of the present invention to improve the retention of the compound in the conjunctival sac or surrounding area. In order to prepare sterile ophthalmic ointment formulations, the BK agonist may be combined with a preservative in an appropriate vehicle, such as white petroleum, mineral oil or liquid lanolin. Sterile ophthalmic gel formulations may be prepared by suspending the BK agonist in a hydrophilic base prepared from the combination of, for example, carbopol-940, or the like, according to the methods known in the art for other ophthalmic formulations. Other compositions of the present invention may contain penetration enhancing agents such as cremephor and tween 80, in the event the BK agonists are less penetrating in the eye.

In other embodiments, a pharmaceutical composition of the invention comprising a non-peptide BK agonist can be administered to a patient alone or in combination with other IOP-lowering agents to increase the potency, efficacy and/or duration of the IOP reduction. Numerous agents known to lower IOP have been previously described (Sugrue, *J. Med. Chem.* 40: 2793-2809, 1997; Clark and Pang, *Expert Opin. Emerg. Drugs,* 7: 141-163, 2002; Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007) including, but not limited to, carbonic anhydrase inhibitors, beta-blockers, prostaglandins, alpha-2 agonists, serotonin-2 agonists, alpha-1 antagonists, dopamine agonists, Rho kinase inhibitors, myosin-II $Ca^{2+}$-ATPase inhibitors, matrix metalloproteinase activators, Activator protein-1 (AP-1) activators (U.S. Pat. No. 7,005,446), natriuretic peptide receptor-B agonists (Potter and Hunter, *J. Biol. Chem.* 276: 6057-6060, 2001; Scotland and Ahluwalia, *Pharmacol. Ther.* 105: 85-93, 2005), $K^+$-channel blockers (European patent EP1772514) and maxi-K-channel activators (Park et al. *J. Pharmacol. Sci.,* 92: 218-227, 2003; Stumpff et al., *Exp. Eye Res.* 80: 697-708, 2005), phosphodiesterase inhibitors (Menniti et al. *Nat. Rev. Drug Discov.,* 5: 660-670, 2006), stimulators/activators of membrane-bound and cytosolic soluble adenylyl and/or guanylyl cyclases (Evgenov et al. *Nature Rev. Drug Discovery* 5: 755-768, 2006). Other compounds and compound classes described for lowering IOP are also useful for the current invention (Clark and Yorio, *Nature Rev. Drug Discovery,* 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007; International Publication No. WO 2006/041875; U.S. Pat. No. 7,005,446). Dual and multipharmacophoric agents can be also contemplated and synthesized by those skilled in the art of conjugating BK agonists with one or more of the agents mentioned above or cited in the publications above.

Just as nitric oxide (NO) liberated de novo from NO-donors or other biological processess have demonstrated physiological and pathological roles, two other compounds, carbon monoxide (CO; Snyder et al., Brain Res. Rev. 26: 167-175, 1998) and hydrogen sulfide ($H_2S$; Boehning and Snyder, *Ann. Rev. Neurosci.* 26: 1050131, 2003; Kimura et al., *Antioxid. Redox Signal.* 7: 795-803, 2005), produced endogenously or delivered exogenously also mediate important biological functions. While CO appears to be able to activate soluble guanylyl cyclase (sGC), and NO can increase CO production (Leffler et al., *Am. J. Physiol. Heart Circ. Physiol.* 289: H1442-H1447, 2005), CO and NO can also act synergistically (Stone and Marletta, Chem. Biol. 5: 255-261, 1998; Sharma and Magde, Methods: 19: 494-505, 1999) Thus, sGC may be activated by NO and CO. Although $H_2S$ has not been shown yet to activate sGC, because it relaxes smooth muscle (Kimura et al., *Antioxid. Redox Signal.* 7: 795-803, 2005), it is likely that sGC is involved in this process. Also, $H_2S$ has recently been shown to lower IOP in rabbits (PCT Application WO 2006/119258). Therefore, in some embodiments, the bradykinin receptor agonists may be advantageously combined with or conjugated with NO-donors and/or CO-donors (tricarbonylchloro[glycinato]ruthenium, tricarbonylchloro[glutamic acidato]ruthenium, tricarbonylchloro[lysinato]ruthenium; tricarbonylchloro[alanato]ruthenium, (Rodella et al., *Free Radical Biol. Med.* 40: 2198-2205, 2006); tricarbonyldichlororuthenium (II) dimer, (Srisook et al., *Biochem. Pharmacol.* 71: 307-318, 2006)), and/or $H_2S$-donors (NaHS; NaS) to achieve synergistic or additive reduction in IOP.

A pharmaceutical composition of the invention may also include an agent that is a source of NO. NO-donors usually cause hyperemia and typically do not exhibit high efficacy in vivo for IOP-lowering. However, a derivative of the anti-epileptic drug gabapentin, NCX8001 ([1-(aminomethyl-cyclohexane acetic acid 3-(nitroxymethyl)phenyl ester]), has been synthesized and shown to be bioavailable and to be a slow releaser of NO and that activates soluble guanylyl cyclase (Wu et al *Br. J. Pharmacol.* 141: 65-74, 2003). The slow NO-releasing compound NCX8001 may readily penetrate the cornea and be hydrolyzed in the aqueous humor to release NO to lower IOP, thereby limiting its hyperemic potential. Therefore, in some embodiments, NCX8001 may be included in a pharmaceutical composition for ocular administration to lower IOP. Other agents that may prove suitable NO donors for lowering IOP include nitroparacetamol and nitroflurbiprofen (*Eur. J. Pharmacol.* 483: 317-322, 2004) and nitroglycerin, isosorbide, sodium nitroprusside, minoxidil and molsidomine also lower IOP (Nathanson *Eur. J. Pharmacol.* 147: 155-156, 1988; Nathanson, *J. Pharmacol. Exp. Ther.* 260: 956-965, 1992; U.S. Pat. No. 5,500,230).

A phosphodiesterase inhibitor is a drug that blocks one or more of the subtypes of the enzyme phosphodiesterase (PDE), therefore preventing the inactivation of the intracellular second messengers, cyclic adenosine monophosphate (cAMP) and cyclic guanosine monophosphate (cGMP), by the respective PDE subtype(s). Of these, there are at least two types, non-selective and selective. Since cAMP and cGMP are known to relax ciliary muscle (Stumpff et al. *Exp. Eye Res.* 80: 697-708, 2005; Wiederholt et al. *Prog. Retinal Eye Res.* 19: 271-295, 2000), a process that leads to change of the TM topography and thus resulting in an increase in the aqueous humor outflow (Stumpff et al. *Exp. Eye Res.* 80: 697-708, 2005; Wiederholt et al. *Prog. Retinal Eye Res.* 19: 271-295, 2000). Thus, PDE inhibitors could be advantageously combined with BK agonists to enhance the efficacy and/or duration of IOP-lowering induced the BK agonists. Various examples of non-selective phosphodiesterase inhibitors include (1) caffeine; (2) bronchodilator theophylline; and, (3) IBMX (3-isobutyl-1-methylxanthine), the latter of which, at least, is used as investigative tool in pharmacological research. Of the selective inhibitors, there are various ones typically related to the inhibitors subtype.

Examples of PDE1-selective inhibitors are Vinpocetine and IC224. (Menniti et al., *Nature Rev. Drug Discov.*, 5: 660-670, 2006). Examples of PDE2-selective inhibitors are erythro-9-(2-hydroxy-3-nonyl)-adenine (EHNA) and BAY 60-7550. (Menniti et al., *Nature Rev. Drug Discov.*, 5: 660-670, 2006).

Examples of PDE3-selective inhibitors are enoximone, milrinone, and cilostamide. All are used clinically for short-term treatment of cardiac failure. Clinically these drugs mimic sympathetic stimulation and increase cardiac output. (Menniti et al., *Nature Rev. Drug Discov.*, 5: 660-670, 2006) Further suitable examples are disclosed in U.S. Pat. No. 6,156,753, the contents of which are hereby incorporated by reference as if it were presented herein in its entirety.

An example of a PDE4-selective inhibitor is rolipram. It is used as investigative tool in pharmacological research. PDE4 is the major cAMP-metabolizing enzyme found in inflammatory and immune cells. PDE4 inhibitors have potential as anti-inflammatory drugs especially in airway diseases. They suppress the release of inflammatory signals, such as, but not limited to, cytokines, and inhibit the production of reactive oxygen species. PDE4 inhibitors have a high therapeutic and commercial potential as non-steroidal disease controllers in inflammatory airway diseases such as asthma, COPD and rhinitis (Menniti et al., *Nature Rev. Drug Discov.*, 5: 660-670, 2006). Further suitable examples are disclosed in U.S. Pat. No. 6,127,363, the contents of which are hereby incorporated by reference as if it were presented herein in its entirety.

Examples of PDE5-selective inhibitors are sildenafil, tadalafil, vardenafil, udenafil, and avanafil. A main use for these PDE5 inhibitors are remedies for erectile dysfunction (Menniti et al., *Nature Rev. Drug Discov.*, 5: 660-670, 2006). Further suitable compounds are those disclosed in WO 94/28902, WO 96/16644, and WO 01/19802, the contents of all which are hereby incorporated by reference as if they were presented herein their entirety, including, but not limited to the griseolic acid derivatives, 2-phenylpurinone derivatives, phenylpyridone derivatives, fused and condensed pyrimidines, pyrimidopyrimidine derivatives, purine compounds, quinazoline compounds, phenylpyrimidinone derivative, imidazoquinoxalinone derivatives, pyrazolopyrimidinones, such as, but not limited to, 5-(2-ethoxy-5-morpholinoacetylphenyl)-1-methyl-3-n-propyl-1,6-dihydro-7H-p yrazolo[4,3d]pyrimidin-7-one, 5-(5-morpholinoacetyl-2-n-propoxyphenyl)-1-methyl-3-n-propyl-1,6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonyl) phenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl 1,3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d]pyrimidin-7-one, 5-[2-ethoxy-5-(1-methyl-2-imidazolyl)phenyl]-1-methyl-3-n-propyl-1,6-dihydro-7H-pyrazolo[4,3-d]pyrimidin-7-one, 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid-4(3H)-one, 7-methylthio-4-oxo-2-(2-propoxyphenyl)-3,4-dihydro-pyrimido[4,5-d] pyrimidine, 6-hydroxy-2-(2-propoxyphenyl)pyrimidine-4-carboxamide, 1-ethyl-3-methylimidazo[1,5a]quinoxalin-4 (5H)-one, 4-phenylmethylamino-6-chloro-2-(1-imidazoloyl)quinazoline, 5-ethyl-8-[3-(N-cyclohexyl-N-methylcarbamoyl)-propyloxy]-4,5-dihydro-4-oxo-pyrido[3,2-e]-pyrrolo[1,2-a]pyrazine, 5'-methyl-3'-(phenylmethyl)-spiro[cyclopentane-1,7'(8'H)-(3'H)-imidazo[2,1-b]purin]-4' (5'H)-one, 1-[6-chloro-4-(3,4-methylenedioxybenzyl)-aminoquinazolin-2-yl)piperidine-4-carboxylic acid, (6R, 9S)-2-(4-trifluoromethyl-phenyl)methyl-5-methyl-3,4,5,6a, 7,8,9,9a-octahydrocyclopent[4,5]-imidazo[2,1-b]-purin-4-one, 1-t-butyl-3-phenylmethyl-6-(4-pyridyl)pyrazolo[3,4-d]-pyrimid-4-one, 1-cyclopentyl-3-methyl-6-(4-pyridyl)-4, 5-dihydro-1H-pyrazolo[3,4-d]pyrimid-4-one, 2-butyl-1-(2-chlorobenzyl)-6-ethoxy-carbonylbenzimidaole, 2-(4- carboxy-piperidino)-4-(3,4-methylenedioxy-benzyl)amino-6-nitroquinazoline and 2-phenyl-8-ethoxycycloheptimidazole.

The PDE6's are distributed in the retina and have been implicated with retinal degeneration (Menniti et al., *Nature Rev. Drug Discov.*, 5: 660-670, 2006). Selective inhibitors comprise sildenafil, zaprinast, and dipyridamole.

An example of a PDE7-selective inhibitor is Dipyridamole. The PDE8's are distributed throughout the cortex, striatum, hippocampus, and cerebellum and have been implicated with Parkinson's disease and psychosis (Menniti et al., *Nature Rev. Drug Discov.* 5: 660-670, 2006).

An example of a PDE8-selective inhibitor is Dipyridamole. The PDE8's are distributed throughout the cortex, striatum, and hippocampus and have been implicated with Alzheimer's disease (Menniti et al., *Nature Rev. Drug Discov.*, 5: 660-670, 2006).

An example of a PDE9-selective inhibitor is BAY 73-6691. The PDE9's are distributed throughout the brain and have been implicated with neurodegeneration and cognitive issue (Menniti et al., *Nature Rev. Drug Discov.*, 5: 660-670, 2006).

Examples of PDE10-selective inhibitors include papaverine and PQ-10. The PDE10's have been implicated with psychosis (Menniti et al., *Nature Rev. Drug Discov.*, 5: 660-670, 2006).

An example of a PDE11-selective inhibitor is tadalafil (Menniti et al., *Nature Rev. Drug Discov.*, 5: 660-670, 2006).

Pharmaceutical compositions of the invention can also be advantageously combined with suitable neuroprotective agents such as memantine, eliprodil, $Ca^{2+}$-channel blockers, betaxolol, etc. (Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007) to obtain IOP-lowering and protection of retinal ganglion cells (RGC). Since angiotensin converting enzyme (ACE) inhibitors appear to potentiate the effects of endogenous and exogenous BK independent of blocking BK inactivation, and ACE and $B_2$-receptors form a complex (Chen et al., *FASEB J.* 13: 2261-2270, 2006), a combination of BK agonists and ACE inhibitors (e.g. captopril; omapatrilat; enalapril, etc) may also be useful for lowering IOP and RGC protection.

As demonstrated in the Examples below, BK agonists can increase outflow of aqueous humor in the eye, thereby lowering intraocular pressure (IOP). In certain embodiments, the invention provides methods for lowering IOP comprising administering to a patient in need thereof a therapeutically effective amount of a non-peptide BK agonist in combination with an aqueous humor production (inflow) inhibitor. In other embodiments, the invention provides pharmaceutical compositions comprising at least one non-peptide BK agonist and/or at least one aqueous humor inflow inhibitor. The combination therapy of the invention provides the benefit of lowering IOP by two mechanisms, including inducing uveoscleral outflow of aqueous humor and inhibiting aqueous humor inflow, which can allow for reduced dosages of the compounds thereby lowering the risk of side effects. In certain embodiments, the BK agonist and aqueous humor inflow inhibitor are administered concurrently in separate pharmaceutical compositions. In other embodiments, the BK agonist and aqueous humor inflow inhibitor are administered formulated together in a pharmaceutical composition. In yet other embodiments, the BK agonist and aqueous humor inflow inhibitor are administered sequentially in separate pharmaceutical compositions.

Non-limiting examples of "aqueous humor inflow inhibitors" include β-blockers (e.g. betaxolol; timolol; levobunolol; U.S. Pat. Nos. 4,883,814, 6,399,605; Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007), α-2 agonists (e.g. brimonidine; apraclonidine; U.S. Pat. Nos. 5,212,196; 5,612,364; U.S. Pat. Nos. 4,883,814, 6,399,605; Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007), carbonic anhydrase inhibitors (e.g. brinzolamide; dorzolamide; U.S. Pat. Nos. 5,153,192; 5,240,923; 5,464,831; 5,538,966; 5,620,970; 6,242,441; 6,242,442; 6,316,441); serotonin-2 agonists (e.g. R-DOI; α-methyl-serotonin; U.S. Pat. No. 6,664,286), and other classes of compounds that exert their IOP-lowering effects in whole or in part by inhibiting the production of aqueous humor (inflow pathway) (Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007).

Preparing Compounds

The procedures below are representative of the methods used to prepare these compounds. One skilled in the art of organic synthesis could prepare these compounds in a number of ways using known methods. The methods are provided for the illustration purposes only.

Preparation of 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-(2-methoxyethyl)benzamide (1)

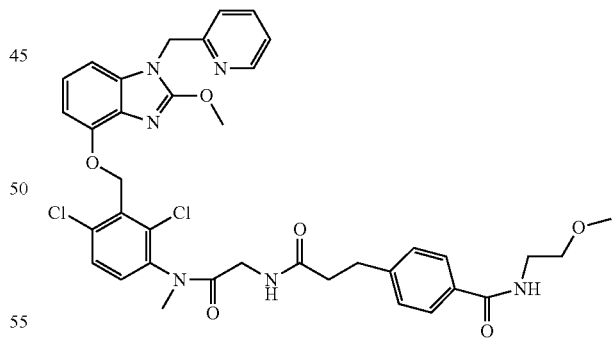

A solution of (E)-benzyl 3-(4((2-methoxyethyl)carbamoyl)phenyl)acrylate (1.0 g, 3.38 mmol) in ethanol (50 ml) is hydrogenated over 10% Pd/C (100 mg) at 50 psi for 24 h. The catalyst is removed by filteration and the solvent removed under vacuum to give 3-(4-((2-methoxyethyl)carbamoyl)phenyl)propanoic acid as a clear oil that solidifies on standing. MS (ESI) 251 (M+), 1H NMR (CDCl$_3$); 1.24 (t, 3H, J=6.8 Hz), 2.686 (t, 2H, J=7.2 Hz), 3.00 (t, 2H, J=7.2 Hz), 3.39 (s, 3H), 3.57 (t, 2H, J=5.2 Hz), 3.63 (t, 2H, J=5.2 Hz), 3.69-3.74 (m, 1H), 7.27 (d, 2H, J=8.4 Hz), 7.73 (d, 2H, J=8.4

Hz). A mixture of 2-amino-N-(2,4-dichloro-3-(((2-methoxy-1-(pyridin-2-ylmethyl)-1H-benzo[d]imidazol-4-yl)oxy)methyl)phenyl)-N-methylacetamide (400 mg, 0.8 mmol), 3-(4-((2-methoxyethyl)carbamoyl)phenyl)propanoic acid (251 mg, 1.0 mmol) and TBTU (O-(Benzotriazol-1-yl)-N,N,N',N'-tetramethyluronium tetrafluoroborate) (321 mg, 1.0 mmol) and diisopropyl amine (0.42 ml) are dissolved in DMF (20 mL) and stirred for 12 h at 23° C. The mixture was poured into water and extracted with ethyl acetate (3×, 50 mL). The ethyl acetate layer is washed with saturated sodium bicarbonate, 1 N HCl then dried over sodium sulfate and concentrated to give a tan oil. The oil was purified by silica gel chromatography using 10% methanol in dichloromethane with 0.1% NH$_4$OH as eluant to give 4-(3-((2-((2-(2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-(2-methoxyethyl)benzamide (1) as a tan solid, 250 mg (43%). MS (ESI) 733 (M$^+$); $^1$H NMR (CDCl$_3$) 2.53 (d, 2H, J=6.8 Hz), 2.89 (d, 2H, J=6.8 Hz), 3.23 (s, 3H), 3.37 (s, 3H), 3.54-3.55 (m, 2H), 3.56-3.62 (m, 2H), 4.21 (s, 3H), 5.29-5.28 (m, 2H), 5.67 (s, 2H), 6.31-6.37 (m, 1H), 6.42-6.55 (m, 1H), 6.75-6.85 (m, 2H), 6.89-6.92 (m, 1H), 7.02-7.08 (m, 1H), 7.15-7.28 (m, 6H), 7.45-7.46 (m, 1H), 7.51-7.59 (m, 1H), 7.67-7.69 (m, 1H), 8.55-8.58 (m, 1H).

Preparation of methyl (5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)pyridin-2-yl)carbamate (2)

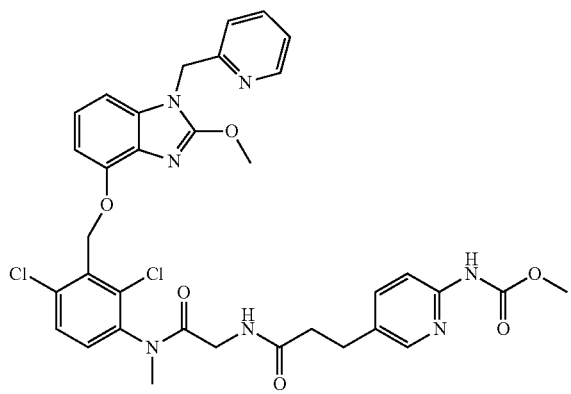

2-amino-N-(2,4-dichloro-3-(((2-methoxy-1-(pyridin-2-ylmethyl)-1H-benzo[d]imidazol-4-yl)oxy)methyl)phenyl)-N-methylacetamide and 3-(6-((methoxycarbonyl)amino)pyridin-3-yl)propanoic acid were combined as previously described for compound 1 to give 2. LCMS (+APCI) 706 (M$^+$). $^1$H-NMR (CDCl$_3$, δ ppm): 8.58 (m, 1H), 8.06 (d, J=2.0 Hz, 1H), 7.85 (d, J=8.8 Hz, 1H), 7.72 (bs, 1H), 7.58 (dt, J=1.6, 7.6 Hz, 1H), 7.51 (2.0, 8.4 Hz, 1H), 7.47 (d, J=8.4 Hz, 1H), 7.21 (d, J=8.4 Hz, 1H), 7.19 (m, 1H), 7.04 (t, J=8.0 Hz, 1H), 6.92 (d, J=8.0 Hz, 1H), 6.83 (d, J=7.6 Hz, 1H), 6.81 (d, J=8.0 Hz, 1H), 6.40 (bt, 1H), 5.67 (d, J=1.6 Hz, 2H), 5.28 (s, 2H), 4.21 (s, 3H), 3.78 (s, 3H), 3.75 (m, 1H), 3.50 (dd, J=4.0, 17.6 Hz, 1H), 3.23 (s, 3H), 2.88 (dd, J=7.6 Hz, 2H), 2.49 (t, J=7.6 Hz, 2H). Calcd. for C$_{34}$H$_{33}$Cl$_2$N$_7$O$_6$+1H$_2$O: C, 56.36; H, 4.87; N, 13.53. Found: C, 56.34; H, 4.68; N, 13.24.

N-(2-((3-(((2-methoxy-1-(pyridin-2-ylmethyl)-1H-benzo[d]imidazol-4-yl)oxy)methyl)-2,4-dimethylphenyl)(methyl)amino)-2-oxoethyl)-3-(2-oxo-2,3-dihydrooxazolo[4,5-b]pyridin-6-yl)propanamide (3)

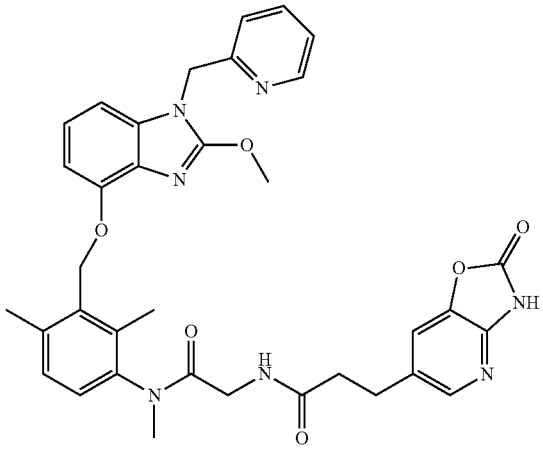

2-amino-N-(2,4-dimethyl-3-(((2-methoxy-1-(pyridin-2-ylmethyl)-1H-benzo[d]imidazol-4-yl)oxy)methyl)phenyl)-N-methylacetamide and 3-(2-oxo-2,3-dihydrooxazolo[4,5-b]pyridin-6-yl)propanoic acid were used to prepare 3 as described above for compound 1. LCMS (+APCI) 650 (M$^+$). $^1$H-NMR (CDCl$_3$, δ ppm): 8.59 (m, 1H), 7.85 (d, J=2.0 Hz, 1H), 7.60 (dt, J=2.0, 7.6 Hz, 1H), 7.22 (m, 2H), 7.05 (t, J=8.0 Hz, 1H), 6.95 (d, J=7.6 Hz, 1H), 6.90 (d, J=8.0 Hz, 1H), 6.82 (m, 3H), 6.73 (bt, 1H), 5.30 (m, 4H), 4.21 (s, 3H), 3.72 (dd, 4.0, 18.0 Hz, 1H), 3.44 (dd, J=4.4, 18.0 Hz, 1H), 3.25 (s, 3H), 2.95 (m, 2H), 2.56 (m, 2H), 2.33 (s, 3H), 2.27 (s, 3H). Calcd. for C$_{35}$H$_{35}$N$_7$O$_6$+0.3H$_2$O: C, 64.17; H, 5.48; N, 14.97. Found: C, 64.06; H, 5.46; N, 14.96.

methyl (5-(3-((2-((3-(((2-methoxy-1-(pyridin-2-ylmethyl)-1H-benzo[d]imidazol-4-yl)oxy)methyl)-2,4-dimethylphenyl)(methyl)amino)-2-oxoethyl)amino)-3-oxopropyl)pyridin-2-yl)carbamate (4)

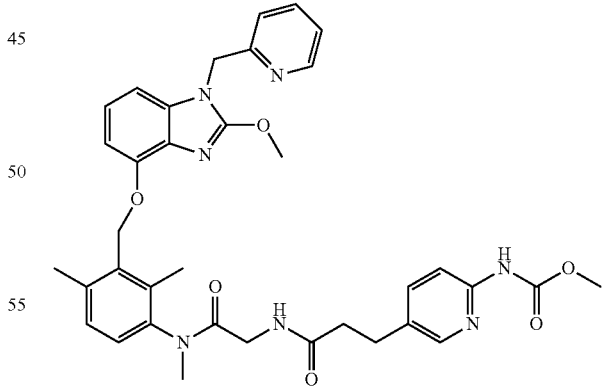

2-amino-N-(3-(((2-methoxy-1-(pyridin-2-ylmethyl)-1H-benzo[d]imidazol-4-yl)oxy)methyl)-2,4-dimethylphenyl)-N-methylacetamide and 3-(6-((methoxycarbonyl)amino)pyridin-3-yl)propanoic acid were used to prepare 4 using the method described for 1. LCMS (+APCI) 666 (M$^+$). $^1$H-NMR (CDCl$_3$, δ ppm): $^1$H-NMR (CDCl$_3$, δ ppm): 8.58 (m, 1H), 8.06 (d, J=1.6 Hz, 1H), 7.85 (d, J=8.4 Hz, 1H), 7.55 (m, 3H), 7.20 (m, 1H), 7.13 (d, J=8.0 Hz, 1H), 7.03 (m, 2H), 6.93 (d, J=8.0 Hz, 1H), 6.81 (m, 2H), 6.43 (bt, J=4.0 Hz, 1H), 5.41 (s, 2H), 5.28 (s, 2H), 4.20 (s, 3H), 3.79 (s, 3H), 3.69 (dd, J=4.4, 18.0 Hz, 1H), 3.47 (dd, J=4.0, 18.0 Hz, 1H), 3.21 (s, 3H), 2.88 (t, J=7.6 Hz, 2H), 2.49 (s, 3H), 2.47 (m, 2H), 2.31 (s, 3H). Calcd. for $C_{36}H_{39}N_7O_6+0.8H_2O$: C, 63.57; H, 6.02; N, 14.42. Found: C, 63.64; H, 5.93; N, 14.53.

Preparation of N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)-3-(6-(methylsulfonamido)pyridin-3-yl)propanamide (5)

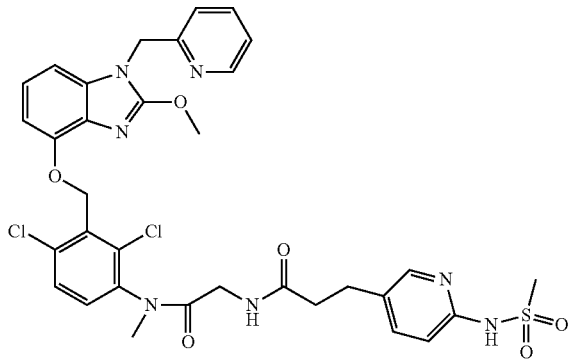

Compound 5 was prepared from 3-(6-(methylsulfonamido)pyridin-3-yl)propanoic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide described for compound 1. MS (APCI) 737(M+), $^1$H NMR (CDCl$_3$) 2.41-2.51 (m, 2H), 2.65 (s, 3H), 2.81-2.92 (m, 2H), 3.05 (s, 3H), 3.22 (s, 3H), 3.33-3.52 (m, 1H), 3.37-3.90 (m, 1H), 5.40 (s, 2H), 5.61 (s, 2H), 6.50-6.61 (m, 1H), 6.71 (s, 1H), 7.17-7.3 (m, 4H), 7.34-7.42 (m, 1H), 7.42-7.52 (m, 1H), 7.55-7.63 (m, 2H), 7.70-7.80 (m, 1H), 7.82-7.95 (m, 1H), 8.04 (s, 1H), 8.61-8.68 (m, 1H).

Preparation of 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperazine-1-carboxamide (7)

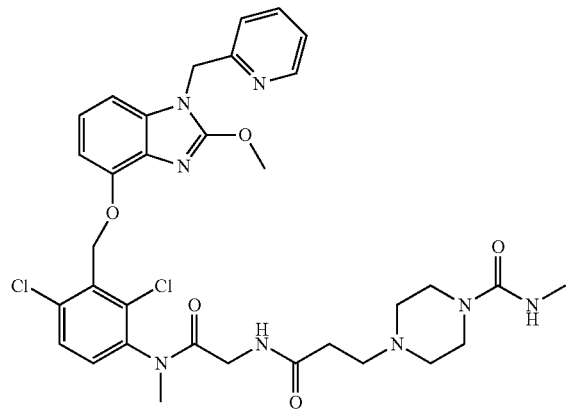

To a cold solution (ice bath) of piperazine-1-carboxylic acid tert-butyl ester (9.0 g, 48.32 mmol) and triethylamine (9.8 g, 96.64 mmol) in dichloromethane (100 mL) was slowly added a solution of methylaminoformyl chloride (5.0 g, 53.5 mmol) in dichloromethane at 0° C. The reaction mixture was allowed to warm to room temperature and stirred overnight, and then partitioned in dichloromethane (200 mL) and water (100 mL). Organic layer was separated, dried (MgSO$_4$), and concentrated to yield tert-butyl 4-(methylcarbamoyl)piperazine-1-carboxylate as a solid which was dissolved in dichloromethane (100 mL) and TFA (20 mL). The solution was stirred for 12 h and the volatiles were evaporated under pressure, the oily residue was dissolved in methanol and 1N hydrogen chloride solution was added. The solid formed was filtered and washed with ether, dried to give N-methylpiperazine-1-carboxamide hydrochloride, 8.12 g (93%)

To a suspension of N-methylpiperazine-1-carboxamide hydrochloride (6 g, 33.52 mmol) and K$_2$CO$_3$ (9.26 g, 67.0 mmol) in acetonitrile (100 mL) was added bromopropionic acid tert-butyl ester (8.4 g, 40.2 mmol). The reaction mixture was stirred at reflux for 12 h, cooled to room temperature and partitioned in ethyl acetate (200 mL) and water (100 mL). Organic layer was separated, dried (MgSO$_4$), and concentrated to give tert-butyl 3-(4-(methylcarbamoyl)piperazin-1-yl)propanoate as an oil which was dissolved in a mixture of dichloromethane (100 mL) and TFA (trifluoroacetic acid) (20 mL) and then stirred overnight. The volatiles were removed under vacuum. The residue was dissolved in methanol, 1N hydrogen chloride in ether was added, and then the solution was concentrated to give 3-(4-(methylcarbamoyl)piperazin-1-yl)propanoic acid as a solid. LCMS 216 (M+1)

A mixture of 2-amino-N-(2,4-dichloro-3-(((2-methoxy-1-(pyridin-2-ylmethyl)-1H-benzo[d]imidazol-4-yl)oxy)methyl)phenyl)-N-methylacetamide and 3-(4-(methylcarbamoyl)piperazin-1-yl)propanoic acid was coupled as described for the preparation of 2 to give 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperazine-1-carboxamide (7).

$^1$HNMR (400 MHz, CDCl$_3$) δ 2.39 (t, 2H), 2.62 (m, 4H), 2.66 (t, 2H), 2.82 (s, 3H), 3.48 (s, 3H), 3.49 (m, 4H), 3.50-3.56 (dd, 1H), 4.20 (s, 3H), 5.29 (s, 2H), 5.65 (m, 2H), 6.91-8.59 (9Har), 8.80 (1H, NH), LC/MS 697 (M+1); $C_{33}H_{38}Cl_2N_8O_5+0.54 H_2O$; Calculated: C, 56.04; H, 5.57; N, 15.84. Found: C, 56.05; H, 5.57; N, 15.66

3-(4-acetamidopiperidin-1-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide (8)

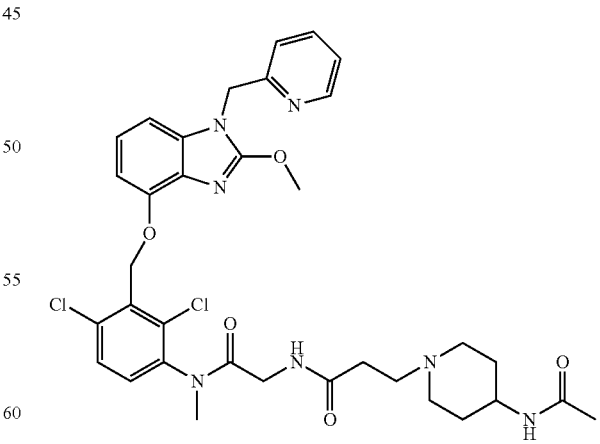

A stirred mixture of 4-acetamidopiperidine (1.82 g, 12.8 mmol) and benzyl acrylate (2.57 g, 15.4 mmol) in acetonitrile (50 mL) was stirred overnight under nitrogen and at 40° C. for 1 h. The mixture was evaporated to dryness and the residue was purified by silica gel chromatograph eluting with a gradient of 0% to 30% dichloromethane/methanol/NH₄OH (10:1:0.1) and dichloromethane to give benzyl 3-(4-acetamidopiperidin-1-yl)propanoate as an oil (3.81 g, 98%).

A mixture of benzyl 3-(4-acetamidopiperidin-1-yl)propanoate (3.81 g, 12.5 mmol) and Pd/C (10%, 0.20 g) in methanol (100 mL) was stirred under hydrogen atmosphere overnight. The solid was filtered and the filtrate was evaporated to give 3-(4-acetamidopiperidin-1-yl)propanoic acid (2.50 g). LCMS (+ESI) 215 (M+1).

To a stirred mixture of 2-amino-N-(2,4-dichloro-3-(((2-methoxy-1-(pyridin-2-ylmethyl)-1H-benzo[d]imidazol-4-yl)oxy)methyl)phenyl)-N-methylacetamide (0.30 g, 0.60 mmol) in anhydrous DMF (15 mL) was added triethyl amine (0.067 g, 0.66 mmol) under nitrogen at 0° C. The mixture was stirred for 30 min and was added 3-(4-acetamidopiperidin-1-yl)propanoic acid (0.257 g, 1.20 mmol) and HBTU (O-Benzotriazole-N,N,N',N'-tetramethyl-uronium-hexafluorophosphate) (0.296 g, 0.78 mmol). The mixture was stirred at room temperature overnight, evaporated, mixed with a saturated brine solution and extracted with ethyl acetate. Evaporation gave a crude oil that was purified using silica chromatography eluting with a gradient of 2% to 30% DCM (dichloromethane)/MeOH/NH₄OH (10:1:0.1). After drying at 78° C. under high vacuum, 3-(4-acetamidopiperidin-1-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide, 8, was isolated as a solid (0.23 g, 55%). LCMS (+ESI) 696 (M+1). ¹H-NMR (CDCl₃, δ ppm): 8.96 (bs, 1H), 8.59 (m, 1H), 7.58 (t, 1H), 7.46 (d, J=8.4 Hz, 1H), 7.27 (m, 1H), 7.19 (t, J=8.0 Hz, 1H), 6.92 (d, J=8.0 Hz, 1H), 6.82 (m, 1H), 5.66 (m, 2H), 5.48 (bd, 1H), 5.28 (s, 2H), 4.20 (s, 3H), 3.85 (m, 2H), 3.54 (dd, J=18, 3.6 Hz, 1H), 3.26 (s, 3H), 2.96 (bd, 2H), 2.62 (m, 2H), 2.37 (m, 2H), 2.14 (m, 2H), 1.97 (s, 3H), 1.96 (m, 3H). Calcd. for C₃₄H₃₉Cl₂N₇O₅+1.4H₂O: C, 56.57; H, 5.84; N, 13.58. Found: C, 56.44; H, 5.59; N, 13.48.

Ethyl (5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-1,4,5,6-tetrahydropyrimidin-2-yl)carbamate (9)

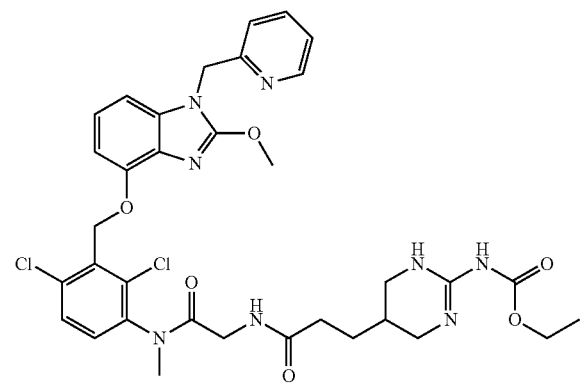

3-(2-((ethoxycarbonyl)amino)-1,4,5,6-tetrahydropyrimidin-5-yl)propanoic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide were used to prepare compound 9 as described for compound 1. LCMS (+ESI) 725 (M⁺). ¹H-NMR (CDCl₃, δ): 8.58 (d, J=4.0 Hz, 1H), 8.37 (bs, 1H), 7.58 (t, 1H), 7.47 (d, J=8.8 Hz, 1H), 7.29 (d, J=8.4 Hz, 1H), 7.18 (m, 1H), 7.03 (t, 1H), 6.92 (d, 1H), 6.80 (m, 2H), 6.62 (bt, 1H), 5.66 (d, J=2.8 Hz, 2H), 5.27 (s, 2H), 4.21 (s, 3H), 4.03 (t, J=7.2 Hz, 2H), 3.81 (dd, J=5.2, 17.6 Hz, 1H), 3.51 (dd, 1H), 3.40 (dd, J=4.8, 12.4 Hz, 2H), 3.24 (s, 3H), 2.98 (dd, J=9.2, 12.4 Hz, 2H), 2.27 (t, J=7.6 Hz, 2H), 1.96 (m, 1H), 1.80 (m, 2H), 1.67 (q, J=8.4 Hz, 2H), 1.23 (t, J=7.2 Hz, 3H).

2-(2-((4-acetamidocyclohexyl)amino)acetamido)-N-(2,4-dichloro-3-(((2-methoxy-1-(pyridin-2-ylmethyl)-1H-benzo[d]imidazol-4-yl)oxy)methyl)phenyl)-N-methylacetamide (10)

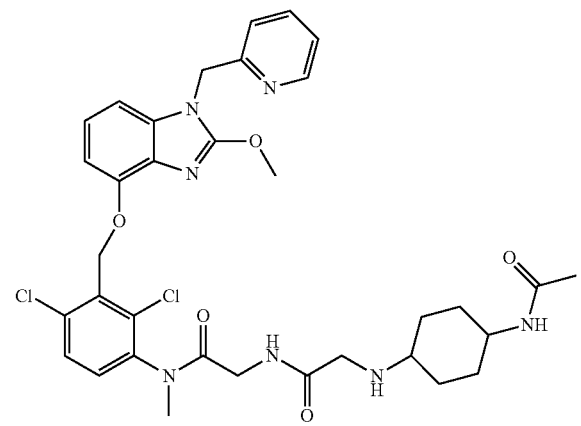

2-((4-acetamidocyclohexyl)amino)acetic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide were used to prepared compound 10 as described for compound 1. LCMS (+ESI) 696 (M⁺). ¹H-NMR (CDCl₃, δ): ¹H-NMR (CDCl₃, δ ppm): 8.58 (dd, J=0.8, 4.8 Hz, 1H), 7.98 (t, 4.4 Hz, 1H), 7.58 (dt, J=1.6, 7.6 Hz, 1H), 7.47 (d, J=8.4 Hz, 1H), 7.29 (d, J=8.4 Hz, 1H), 7.19 (m, 1H), 7.04 (t, J=8.0 Hz, 1H), 6.92 (d, J=8.0 Hz, 1H), 6.81 (d, J=7.2 Hz, 1H), 6.79 (d, J=7.6 Hz, 1H), 5.65 (dd, J=10.4, 13.6 Hz, 2H), 5.28 (s, 2H), 5.26 (m, 1H), 4.21 (s, 3H), 3.84 (dd, J=5.2, 17.6 Hz, 1H), 3.73 (m, 1h), 3.54 (dd, J=4.0, 17.6 Hz, 1H), 3.31 (m, 2H), 3.25 (s, 3H), 2.36 (m, 1H), 1.99 (m, 4H), 1.94 (s, 3H), 1.16 (m, 4H). Calcd. for C₃₄H₃₉Cl₂N₇O₅+1.0H₂O: C, 57.14; H, 5.78; N, 13.72. Found: C, 56.87; H, 5.75; N, 13.54.

1-(2-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2-oxoethyl)-N-methylpiperidine-4-carboxamide (13)

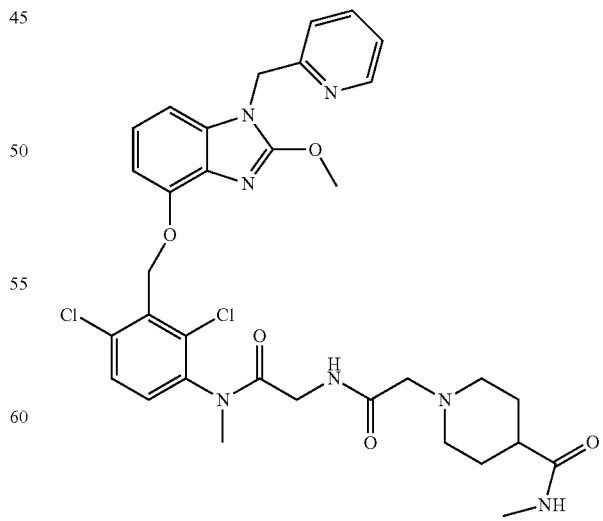

2-(4-(methylcarbamoyl)piperidin-1-yl)acetic acid and 2-amino-N-(2,4-dichloro-3-(((2-methoxy-1-(pyridin-2-ylmethyl)-1H-benzo[d]imidazol-4-yl)oxy)methyl)phenyl)-N- methylacetamide were combined as described for compound 1 to give 13. LCMS (+ESI) 682 (M+). $^1$H-NMR (CDCl$_3$, δ): 8.58 (m, 1H), 7.88 (bt, 1H), 7.58 (t, 1H), 7.47 (d, J=8.4 Hz, 1H), 7.31 (d, J=8.4 Hz, 1H), 7.19 (m, 1H), 7.03 (t, J=8.0 Hz, 1H), 6.92 (d, J=8.0 Hz, 1H), 6.83 (d, J=8.0 Hz, 1H), 6.81 (d, J=8.0 Hz, 1H), 5.67 (s, 2H), 5.28 (s, 2H), 4.20 (d, J=2.8 Hz, 3H), 3.82 (dd, 1H), 3.56 (dd, 1H), 3.24 (s, 3H), 2.94 (m, 4H), 2.81 (d, J=4.8 Hz, 3H), 2.18 (m, 3H), 1.85 (m, 5H). Calcd. for C$_{33}$H$_{37}$Cl$_2$N$_7$O$_5$+3.1H$_2$O: C, 53.67; H, 5.90; N, 13.28. Found: C, 53.29; H, 5.52; N, 12.92.

N-(2,4-dichloro-3-(((2-methoxy-1-(pyridin-2-ylmethyl)-1H-benzo[d]imidazol-4-yl)oxy)methyl)phenyl)-N-methyl-2-(2-morpholinoacetamido)acetamide (14)

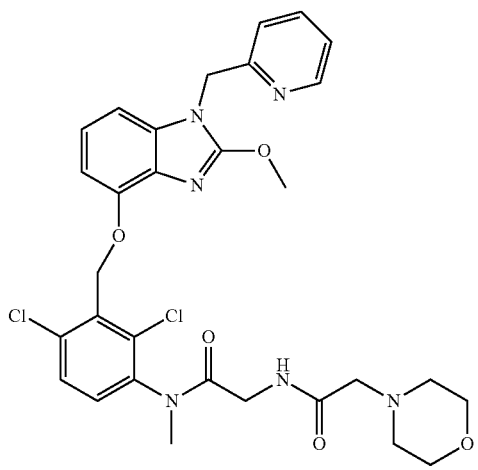

2-amino-N-(2,4-dichloro-3-(((2-methoxy-1-(pyridin-2-ylmethyl)-1H-benzo[d]imidazol-4-yl)oxy)methyl)phenyl)-N-methylacetamide and 2-morpholinoacetic acid were combined to give 14 as previously described. LCMS (+ESI) 627 (M+). $^1$H-NMR (CDCl$_3$, δ): 8.58 (dd, J=0.8, 4.8 Hz, 1H), 7.88 (bt, 1H), 7.58 (td, J=1.6, 8.0 Hz, 1H), 7.30 (d, J=8.4 Hz, 1H), 7.19 (m, 1H), 7.03 (t, J=8.0 Hz, 1H), 6.92 (d, J=7.6 Hz, 1H), 6.83 (d, J=7.6 Hz, 1H), 6.81 (d, J=7.6 Hz, 1H), 5.67 (d, J=3.2 Hz, 2H), 5.28 (s, 2H), 4.21 (s, 3H), 3.87 (dd, J=5.2, 17.6 Hz, 1H), 3.77 (m, 4H), 3.54 (dd, J=4.4, 17.6 Hz, 1H), 3.25 (s, 3H), 2.55 (m, 4H). Calcd. for C$_{30}$H$_{32}$Cl$_2$N$_6$O$_5$: C, 57.42; H, 5.14; N, 13.39. Found: C, 57.23; H, 5.22; N, 13.23.

2-(2-(4-acetamidopiperidin-1-yl)acetamido)-N-(2,4-dichloro-3-(((2-methoxy-1-(pyridin-2-ylmethyl)-1H-benzo[d]imidazol-4-yl)oxy)methyl)phenyl)-N-methylacetamide (15)

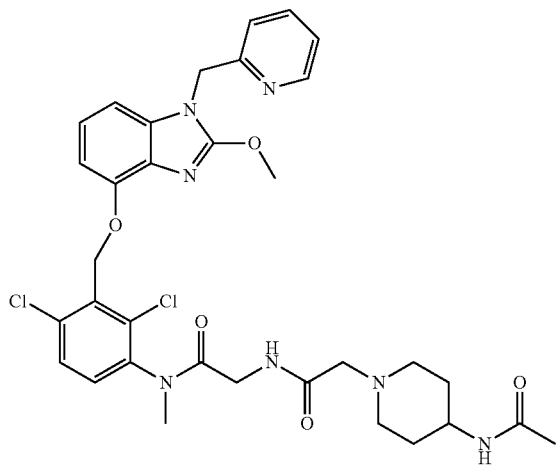

2-(4-acetamidopiperidin-1-yl)acetic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide are combined as previously described to give 15. LCMS (+ESI) 682 (M+). $^1$H-NMR (CDCl$_3$, δ): 8.58 (m, 1H), 7.97 (bt, 1H), 7.58 (t, 1H), 7.47 (d, J=8.4 Hz, 1H), 7.29 (d, J=8.4 Hz, 1H), 7.19 (m, 1H), 7.03 (t, J=8.0 Hz, 1H), 6.92 (d, J=7.6 Hz, 1H), 6.83 (d, J=8.0 Hz, 1H), 6.81 (d, J=7.6 Hz, 1H), 5.67 (s, 2H), 5.33 (bd, 1H), 5.28 (s, 2H), 4.21 (s, 3H), 3.82 (dd, 1H), 3.81 (m, 1H), 3.56 (dd, 1H), 3.25 (s, 3H), 2.99 (d, 2H), 2.80 (m, 2H), 2.32 (m, 2H), 1.96 (s, 3H), 1.92 (m, 2H), 1.52 (m, 2H).

3-(4-acetylpiperazin-1-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide (16)

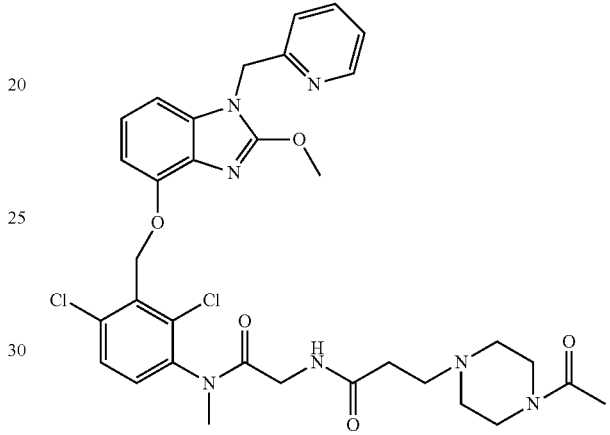

2-amino-N-(2,4-dichloro-3-(((2-methoxy-1-(pyridin-2-ylmethyl)-1H-benzo[d]imidazol-4-yl)oxy)methyl)phenyl)-N-methylacetamide and 3-(4-acetylpiperazin-1-yl)propanoic acid were used to prepare 16 as described for compound 1. LCMS (+ESI) 668 (M). $^1$H-NMR (CDCl$_3$, δ): 8.58 (m, 1H), 7.84 (bt, 1H), 7.58 (t, J=2.0 Hz, 1H), 7.47 (d, J=8.8 Hz, 1H), 7.30 (d, J=8.8 Hz, 1H), 7.18 (m, 1H), 7.03 (t, J=8.0 Hz, 1H), 6.92 (d, J=8.0 Hz, 1H), 6.82 (m, 2H), 5.68 (d, J=4.0 Hz, 2H), 5.28 (s, 2H), 4.21 (s, 3H), 3.89 (dd, 1H), 3.69 (m, 2H), 3.25 (s, 3H), 2.53 (m, 4H), 2.04 (s, 3H). Calcd. for C$_{33}$H$_{37}$Cl$_2$N$_7$O$_5$+1H$_2$O: C, 56.57; H, 5.61; N, 13.99. Found: C, 56.33; H, 5.48; N, 14.21.

Preparation of 4-(3-((2-((2,4-dichloro-3-(((2-ethyl-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperazine-1-carboxamide (19)

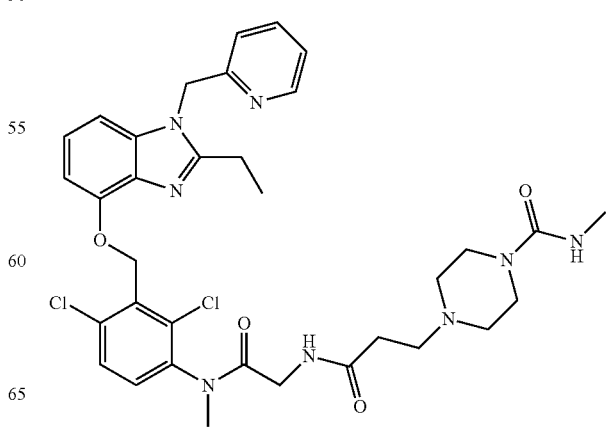

2,3-diaminophenol (5 g, 40.3 mmol) was dissolved in propionic acid (10 mL) and stirred at 150° C. for 3 h. The reaction mixture was cooled to room temperature and the volume reduced under high vacuum to give a brown solid which was partitioned between chloroform and a saturated solution of bicarbonate, the chloroform layer was separated, dried and concentrated to give a brown solid. The brown solid (1.3 g, 8.0 mmol) was dissolved in DMF (40 mL) and $K_2CO_3$ (2.8 g, 0.02 mmol) was added followed by benzylbromide (1.5 g, 8.8 mmol). The reaction mixture was stirred at room temperature overnight, partitioned with water and ethyl acetate, ethyl acetate layer was separated, dried ($MgSO_4$), concentrated, and purified by flash chromatography to give 7-benzyloxy-2-ethyl-1H-benzimidazole (0.9 g, 44%). LCMS 253 ($M^+$)

To a solution cold solution (ice bath) of 7-benzyloxy-2-ethyl-1H-benzimidazole prepared above (0.8 g, 3.17 mmol) in DMF (10 mL) was added sodium hydride (0.41 g, 10.47 mmol), followed by 2-(bromomethyl)pyridine hydrobromide (0.88 g, 3.49 mmol). After addition of the bromide the reaction mixture was allowed to warm to room temperature and stirred for 16 h. The reaction mixture was partitioned between water and ethyl acetate. Ethyl acetate layer was separated, dried ($MgSO_4$), and concentrated to give 4-benzyloxy-2-ethyl-1-pyridin2-ylmethyl-1H-benzoimidazole as a solid which was crystallized in ethyl acetate to give 4-benzyloxy-2-ethyl-1-pyridin2-ylmethyl-1H-benzoimidazole, 0.35 g. LCMS 344 (M+1). $^1$HNMR (400 MHz, $CDCl_3$) δ 1.38 (t, 3H), 2.90 (q, 2H), 5.40-5.42 (m, 4H), 6.65-8.60 (12H, Ar) 4-benzyloxy-2-ethyl-1-pyridin2-ylmethyl-1H-benzoimidazole (0.35 g, 1.2 mmol) was dissolved in ethanol and in presence of Pd/C, 10% and stirred under a hydrogen balloon overnight. The solution was filtered through celite and concentrated to give 2-ethyl-1-pyridin-2-ylmethyl-1H-benzoimidazole-4-ol. $^1$HNMR (400 MHz, $CDCl_3$) δ 1.28 (t, 3H), 2.87 (q, 2H), 5.40 (s, 2H), 6.49 (d, 1Har), 6.51 (m, 2H, Ar), 6.92 (m. 1H Ar), 7.09 (m, 1H, Ar), 7.73 (m, 1H, Ar), 8.49 (m, 1H, Ar), 9.57 (1H, OH).

To a solution of N-(2,4-Dichloro-3-hydroxymethyl-phenyl)-2-(1,3-dioxo-1,3-dihydro-isoindol-2-yl)-N-methyl-acetamide (1.0 g, 2.54 mmol) in anhydrous dichloromethane (40 mL) and two drops of DMF was added thionyl chloride (0.6 g, 5.08 mmol), and the reaction mixture was stirred 3 h at room temperature. The volatiles were evaporated and, toluene (50 mL) was added and evaporated, this was repeated twice to get rid of traces of thionyl chloride. To the solid residue dissolved in acetonitrile (100 mL) was added $K_2CO_3$ (0.7 g, 5.1 mmol) and 2-ethyl-1-pyridin-2-ylmethyl-1H-benzoimidazole-4-ol (0.70 g, 2.76 mmol). The reaction mixture was stirred at 70° C. for 4 h then cooled. The reaction mixture was partitioned between water and ethyl acetate. The ethyl acetate layer was separated, dried ($MgSO_4$) and concentrated to give a solid, which was dissolved in 10 ml of 2 N methyl amine as a solution in ethanol, and stirred at 40° C. for 2 h. After, the solution was cooled and concentrated to give a solid which was purified by column chromatography using a mixture of dichloromethane and 5% ammonium in methanol (9:1) to yield 2-Amino-N-[2,4-dichloro-3-(2-ethyl-1-pyridin-2-ylmethyl-1H-benzoimidazol-4-yloxymethyl)-phenyl]-N-methyl-acetamide. LCMS 498 ($M^+$)

2-Amino-N-[2,4-dichloro-3-(2-ethyl-1-pyridin-2-ylmethyl-1H-benzoimidazol-4-yloxymethyl)-phenyl]-N-methyl-acetamide and 3-(4-(methylcarbamoyl)piperazin-1-yl) propanoic acid were coupled as described for compound 1 above to give 19. MS (APCI) 694 ($M^+$), $^1$HNMR (400 MHz, MeOD) δ 2.12 (t, 3H), 2.49 (t, 2H), 2.71 (m, 4H), 2.89 (s, 3H), 2.89 (m, 2H), 2.93 (q, 2H), 3.2 (s, 3H), 3.31 (m, 4H), 3.46-3.84 (dd, 3H), 5.55 (m, 4H), 6.93-8.51 (m, 9Har), LCMS 695 (M+1); $C_{34}H_{38}Cl_2N_8O_4$+1.73 $H_2O$; Calculated: C, 56.69; H, 5.98; N, 15.56. Found: C, 56.69; H, 6.18; N, 15.81.

4-((2-((2-((3-(((2-methoxy-1-(pyridin-2-ylmethyl)-1H-benzo[d]imidazol-4-yl)oxy)methyl)-2,4-dimethylphenyl)(methyl)amino)-2-oxoethyl)amino)-2-oxoethyl)amino)-N-methylpiperidine-1-carboxamide (21)

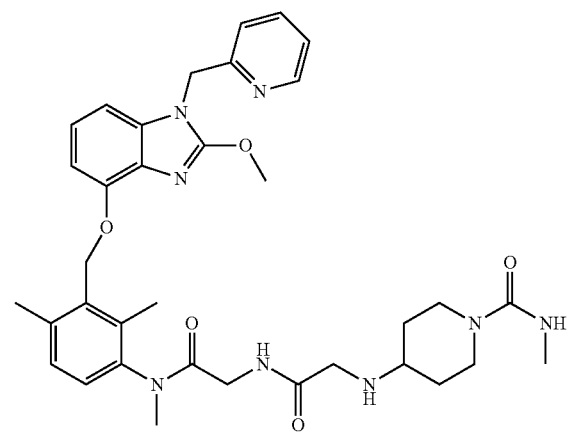

2-((1-(methylcarbamoyl)piperidin-4-yl)amino)acetic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide were used to prepare compound 21 as described for compound 1. LCMS (+ESI) 657 ($M^+$). $^1$H-NMR ($CDCl_3$, δ): $^1$H-NMR ($CDCl_3$, δ ppm): 8.51 (dd, J=0.8, 4.0 Hz, 1H), 7.85 (t, 1H), 7.52 (t, 1H), 7.47 (d, J=8.4 Hz, 1H), 7.11 (m, 1H), 7.07 (d, J=8.0 Hz, 1H), 6.96 (m, 2H), 6.86 (d, J=7.6 Hz, 1H), 6.74 (m, 2H), 5.33 (s, 2H), 5.21 (s, 2H), 4.37 (bq, 1H), 4.13 (s, 3H), 3.79 (m, 2H), 3.67 (dd, 1H), 3.46 (dd, 1H), 3.23 (s, 2H), 3.15 (s, 3H), 2.75 (m, 2H), 2.72 (d, J=4.8 Hz, 3H), 2.53 (m, 1H), 2.43 (s, 3H), 2.27 (s, 3H), 1.82 (m, 2H), 1.24 (m, 3h).

Preparation of N-(2-((2,4-dichloro-3-((2-methoxy-1-(pyridin-2-ylmethyl)-1H-benzo[d]imidazol-4-yloxy) methyl)phenyl)(methyl)amino)-2-oxoethyl)-1,3'-bipyrrolidine-3-carboxamide (22)

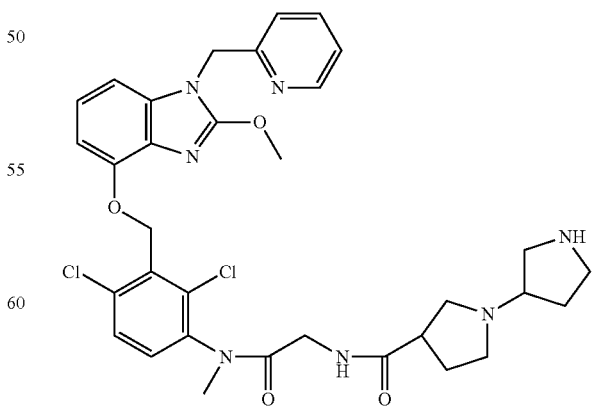

A solution of 1'-(tert-butoxycarbonyl)-[1,3'-bipyrrolidine]-3-carboxylic acid (0.5 g, 1.0 mmol) in anhydrous DMF (20 ml) was treated with HOBT (Hydroxybenzotriazole) (0.21 g, 1.52 mmol), EDCI (1-ethyl-3-(3-dimethylaminopropyl) carbodiimide), hydrochloride (0.24 g, 1.27 mmol) then 2-amino-N-(2,4-dichloro-3-(((2-methoxy-1-(pyridin-2-ylmethyl)-1H-benzo[d]imidazol-4-yl)oxy)methyl)phenyl)-N-methylacetamide (0.50 g, 1.0 mmol) and the mixture was stirred at room temperature overnight. The reaction was treated with water (100 mL) and the resulting precipitate was filtered. The aqueous mixture was treated with aqueous saturated sodium bicarbonate (100 mL), extracted with ethyl acetate (200 mL×2). The combined organic layers were dried over magnesium sulfate, filtered and evaporated to give a white solid, 0.62 g that was purified by chromatography (silica gel, dichloromethane and methanol gradient) to afford tert-butyl 3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)carbamoyl)-[1,3'-bipyrrolidine]-1'-carboxylate as a white solid, 0.41 g (53%), that was pure by LC/MS (+ESI) m/z 766 (M+).

A solution of tert-butyl 3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)carbamoyl)-[1,3'-bipyrrolidine]-1'-carboxylate (0.27 g, 0.35 mmol) in dichloromethane (10 ml) was cooled in an ice bath and treated with dropwise addition of trimethylsilyl triflate (0.07 mL, 0.39 mmol) and stirred at 0° C. for ten minutes. The reaction was treated with another dropwise addition of trimethylsilyl triflate (0.06 mL, 0.35 mmol) stirring at 0° C. for one hour. The reaction was quenched with triethyl amine (1 mL), evaporated, treated with aqueous saturated sodium bicarbonate (10 mL) and brine (100 mL) and extracted with dichloromethane (100 mL×3). The combined organic layers were dried over magnesium sulfate, filtered and evaporated to afford N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)-[1,3'-bipyrrolidine]-3-carboxamide (22) as a tan solid, 0.22 g (94%), that was about 90% pure by LC/MS (+ESI) m/z 666 (M++1) with about 10% impurity of MW 786 (M+). 786 (M++1). $^1$HNMR (400 MHz, CDCl$_3$) δ 8.59 (s, 1H), 7.93 (m, 1H), 7.59 (m, 1H), 7.45 (m, 1H), 7.32 (m, 1H), 7.19 (m, 1H), 7.04 (m, 1H), 6.95 to 2.00 (many m, 17H). $^{13}$CNMR (100 MHz, CDCl$_3$) δ 175.6, 169.5, 169.2, 156.9, 156.1, 149.6, 149.1, 138.4, 137.1, 136.4, 135.8, 135.4, 130.1, 129.8, 122.6, 121.7, 120.8, 107.4, 103.1, 67.1, 62.6, 57.5, 55.0, 54.9, 53.4, 51.4, 50.4, 47.7, 46.1, 44.0, 43.9, 41.9, 30.9, 9.0.

Preparation of N3-(2-((2,4-dichloro-3-((2-methoxy-1-(pyridin-2-ylmethyl)-1H-benzo[d]imidazol-4-yloxy)methyl)phenyl)(methyl)amino)-2-oxoethyl)-N1'-methyl-1,3'-bipyrrolidine-1',3-dicarboxamide (24)

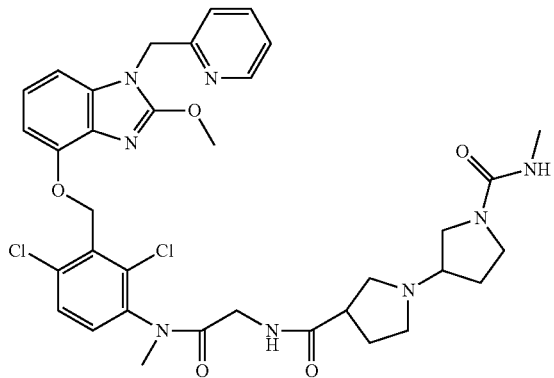

A solution of N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)-[1,3'-bipyrrolidine]-3-carboxamide (0.20 g, 0.3 mmol) in dichloromethane (15 ml) was treated with methyl isocyanate (0.023 mL, 0.39 mmol) with stirring at room temperature for ten minutes. The reaction was evaporated, treated with methanol and evaporated to a tan solid, 0.20 g. This residue was purified by chromatography (silica gel, dichloromethane and methanol gradient) to afford 24 as a white solid, 0.06 g (28%), that was pure by LC/MS (+ESI) m/z 723 (M+), and was pure by $^1$HNMR (400 MHz, CDCl$_3$) δ 8.58 (s, 1H), 7.59 (m, 1H), 7.49 (m, 2H), 7.29 (m, 1H), 7.19 (m, 1H), 7.05 (m, 1H), 6.80 (m, 2H), 5.69 (s, 2H), 5.29 (s, 2H), 4.20 (m, 4H), 3.80 (m, 1H), 3.50 (m, 3H), 3.25 (m, 5H), 2.85 (m, 7H), 2.55 (m, 2H), 2.10 (m, 5H). $^{13}$CNMR (100 MHz, CDCl$_3$) δ 150, 148, 131, 130, 121, 122, 123, 108, 103, 65, 63, 58, 57, 51, 50, 48, 43, 42, 41, 35, 31, 30, 29, 28. Anal. Calcd for C$_{15}$H$_{21}$N$_3$O$_3$+1.0H$_2$O: C, 56.68; H, 5.71; N, 15.11. Found: C, 56.73; H, 5.51; N, 14.82.

3-(2-acetamido-1,4,5,6-tetrahydropyrimidin-5-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide (25)

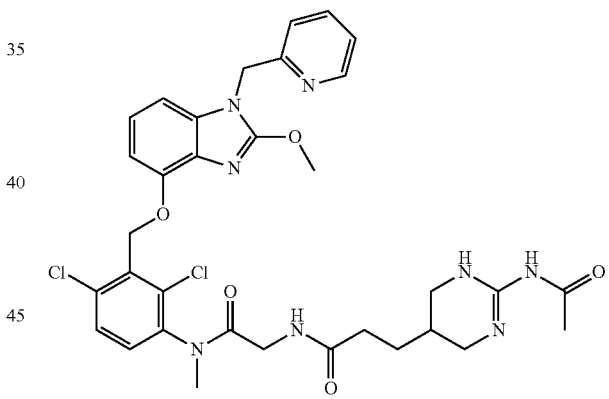

2-amino-N-(2,4-dichloro-3-(((2-methoxy-1-(pyridin-2-ylmethyl)-1H-benzo[d]imidazol-4-yl)oxy)methyl)phenyl)-N-methylacetamide and 3-(2-acetamido-1,4,5,6-tetrahydropyrimidin-5-yl)propanoic acid are used to prepare compound 25 as described for compound 1. LCMS (+ESI) 695 (M+). $^1$H-NMR (CDCl$_3$, δ ppm): 8.58 (dd, J=0.4, 4.8 Hz, 1H), 7.58 (dt, J=1.6, 7.6 Hz, 1H), 7.47 (d, J=8.8 Hz, 1H), 7.30 (d, J=8.4 Hz, 1H), 7.19 (m, 1H), 7.03 (t, J=8.0 Hz, 1H), 6.92 (d, J=8.0 Hz, 1H), 6.82 (m, 2H), 6.68 (bs, 1H), 5.66 (dd, J=2.4, 14.4 Hz, 2H), 5.27 (s, 2H), 4.21 (s, 3H), 3.80 (dd, 1H), 3.51 (dd, 1H), 3.439 (dd, J=4.4, 12.8 Hz, 2H), 3.24 (s, 3H), 2.99 (dd, J=9.2, 12.0 Hz, 2H), 2.29 (t, J=7.6 Hz, 2H), 2.00 (s, 3H), 1.98 (m, 1H), 1.68 (m, 2H). Calcd. for C$_{35}$H$_{36}$Cl$_2$N$_8$O$_5$+1.2H$_2$O: C, 55.26; H, 5.40; N, 15.62. Found: C, 55.32; H, 5.25; N, 15.38.

5-(3-((2-((2,4-dichloro-3-(((2-methyl-4-(pyridin-2-ylmethoxy)quinolin-8-yl)oxy)methyl)phenyl)(methyl)amino)-2-oxoethyl)amino)-3-oxopropyl)-N-methylpicolinamide (27)

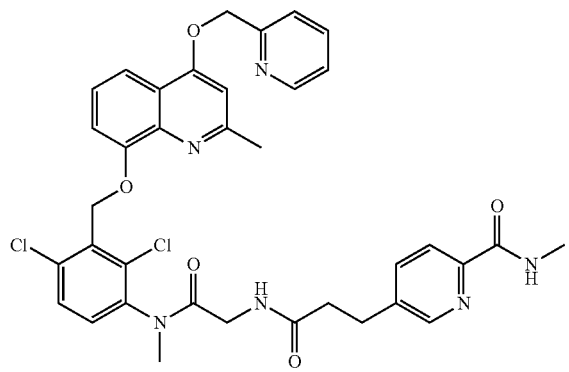

Compound 27 was prepared from 3-(6-(methylcarbamoyl)pyridin-3-yl)propanoic acid and 2-amino-N-(2,4-dichloro-3-4(2-methyl-4-(pyridin-2-ylmethoxy)quinolin-8-yl)oxy)methyl)phenyl)-N-methylacetamide in a as described for compound 1. MS (APCI) 700(M+), $^1$H NMR (CDCl$_3$) 2.17 (s, 3H), 2.48 (t, 2H, J=5.8 Hz), 2.65 (s, 3H), 2.89 (t, 2H, J=5.8 Hz), 3.22 (s, 3H), 3.4-3.5 (m, 1H), 3.7-3.81 (m, 1H), 5.41 (s, 2H), 5.61 (s, 2H), 7.2-7.3 (m, 1H), 7.31-7.40 (m, 1H), 7.44-7.62 (m, 5H), 7.75-7.76 (m, 1H), 7.9-8.06 (m, 4H), 8.63-8.65 (m, 1H).

3-(4-acetamidophenyl)-N-(2-((2,4-dichloro-3-(((2-methyl-4-(pyridin-2-ylmethoxy)quinolin-8-yl)oxy)methyl)phenyl)(methyl)amino)-2-oxoethyl)propanamide (28)

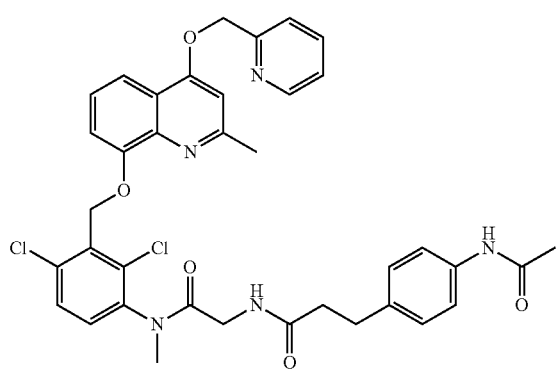

Compound 28 was prepared from 3-(4-acetamidophenyl)propanoic acid and 2-amino-N-(2,4-dichloro-3-(((2-methyl-4-(pyridin-2-ylmethoxy)quinolin-8-yl)oxy)methyl)phenyl)-N-methylacetamide in a as described for compound 1. MS (APCI) 700(M+), $^1$H NMR (CDCl$_3$) 1.91 (s, 3H), 2.4-2.6 (m, 5H), 2.80-2.93 (m, 2H), 3.10 (s, 3H), 3.32-3.45 (m, 1H), 3.61-3.71 (m, 1H), 5.41 (s, 2H), 5.45-5.56 (m, 2H), 6.41-6.45 (m, 1H), 6.71 (s, 1H), 6.91-7.05 (m, 3H), 7.18-7.21 (m, 1H), 7.22-7.28 (m, 1H), 7.31-7.50 (m, 2H), 7.55-7.60 (m, 1H), 7.65-7.75 (m, 1H), 7.91-7.99 (m, 1H), 8.61-8.69 (m, 1H), 9.14 (s, 1H).

N-(2-((2,4-dichloro-3-(((2-methyl-4-(pyridin-2-ylmethoxy)quinolin-8-yl)oxy)methyl)phenyl)(methyl)amino)-2-oxoethyl)-3-(4-(methylsulfonamido)phenyl)propanamide (29)

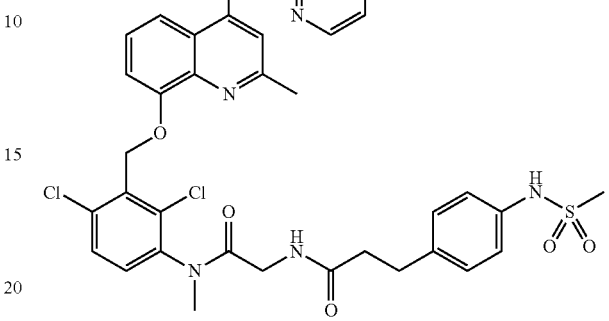

Compound 29 was prepared from 3-(4-(methylsulfonamido)phenyl)propanoic acid and 2-amino-N-(2,4-dichloro-3-(((2-methyl-4-(pyridin-2-ylmethoxy)quinolin-8-yl)oxy)methyl)phenyl)-N-methylacetamide in a as described for compound 1. MS (APCI) 736 (M+), $^1$H NMR (CDCl$_3$) 2.45-2.56 (m, 2H), 2.65 (s, 3H), 2.83-2.92 (m, 5H), 3.15 (s, 3H), 3.35-3.48 (m, 1H), 3.75-3.85 (m, 1H), 5.41 (s, 2H), 5.61 (s, 2H), 6.61-6.65 (m, 1H), 6.71 (s, 1H), 7.15 (s, 4H), 7.24-7.34 (m, 2H), 7.3-7.45 (m, 5H), 7.56-7.61 (d, 1H, J=7.8 Hz), 7.66-7.78 (m, 1H), 7.91-7.94 (dd, 1H, J=1, 7.74 Hz), 8.64 (d, 1H, J=4.14 Hz).

4-(3-((2-((2,4-dichloro-3-(((2-methyl-4-(pyridin-2-ylmethoxy)quinolin-8-yl)oxy)methyl)phenyl)(methyl)amino)-2-oxoethyl)amino)-3-oxopropyl)-N-methylbenzamide (31)

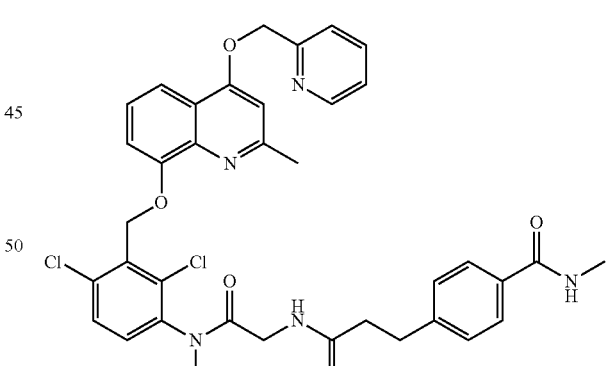

Compound 31 was prepared from 3-(4-(methylcarbamoyl)phenyl)propanoic acid and 2-amino-N-(2,4-dichloro-3-(((2-methyl-4-(pyridin-2-ylmethoxy)quinolin-8-yl)oxy)methyl)phenyl)-N-methylacetamide in a as described for compound 1. MS (APCI) 700 (M+), $^1$H NMR (CDCl$_3$) 2.42-2.52 (m, 2H), 2.61 (s, 3H), 2.85-2.95 (m, 5H), 3.15 (s, 3H), 3.32-3.45 (m, 1H), 3.62-3.68 (m, 1H), 5.41 (s, 2H), 5.61 (s, 2H), 6.41-6.51 (m, 1H), 6.55-6.62 (m, 1H), 6.71 (s, 1H), 7.15-7.31 (m, 4H), 7.31-7.45 (m, 2H), 7.55-7.62 (m, 1H), 7.62-7.71 (m, 2H), 7.71-7.81 (m, 1H), 7.91-7.95 (m, 1H), 8.65-8.72 (m, 1H).

3-(6-acetamidopyridin-3-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide (32)

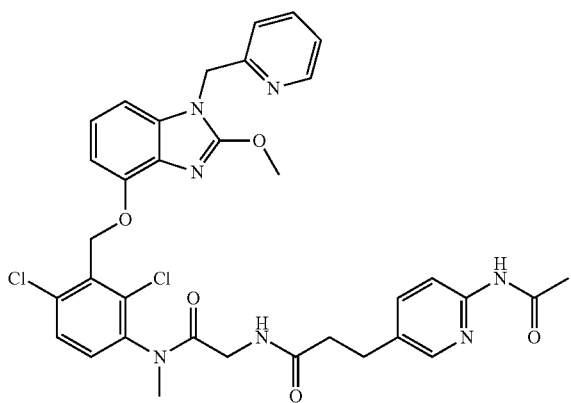

Compound 32 is prepared 2-amino-N-(2,4-dichloro-3-(((2-methoxy-1-(pyridin-2-ylmethyl)-1H-benzo[d]imidazol-4-yl)oxy)methyl)phenyl)-N-methylacetamide and 3-(6-acetamidopyridin-3-yl)propanoic acid as described for compound 1. MS (APCI) 690 (M+), $^1$H NMR 2.18 (s, 3H), 2.49 (t, 2H, J=7.4 Hz), 2.89 (t, 2H, J=7.4 Hz), 3.32 (s, 3H), 3.4-3.55 (m, 1H), 3.7-3.82 (m, 1H), 4.21 (s, 3H), 5.28 (s, 2H), 5.66 (s, 2H), 6.45-6.52 (m, 1H), 6.81 (t, 2H, J=8.2 Hz), 6.92 (d, 1H, J=7.86 Hz), 7.01-7.06 (m, 1H), 7.17-7.19 (m 1H), 7.4-7.6 (m, 4H), 7.9-7.95 (m, 1H), 8.06-8.09 (m, 2H), 8.55-8.59 (m, 1H).

4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylbenzamide (33)

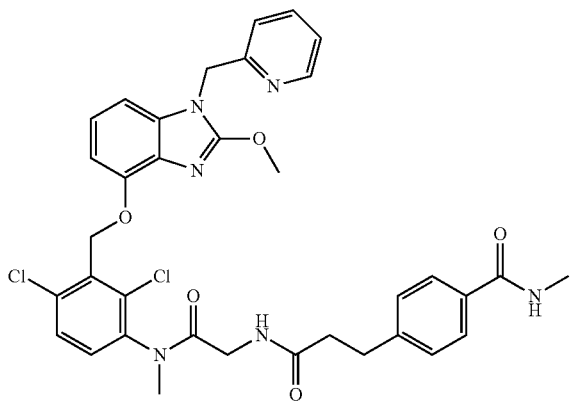

Compound 33 is prepared from 3-(4-(methylcarbamoyl)phenyl)propanoic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide as described for compound 1. MS (ESI) 689 (M+) 1HNMR (CDCl$_3$), 2.42-2.58 (m, 2H), 2.80-2.90 (m, 5H), 3.18 (s, 3H), 3.3-3.5 (m, 1H), 3.65-3.72 (m, 1H), 4.14 (s, 3H), 5.25 (s, 2H), 5.5-5.7 (m, 2H), 6.4-6.6 (m, 2H), 6.75-6.82 (m, 2H), 6.85-6.91 (m, 1H), 6.95-7.10 (m, 3H), 7.38-7.45 (m, 1H), 7.52-7.62 (m, 1H), 6.8-6.72 (m, 2H), 8.52-8.60 (m, 1H).

Preparation of (S)-tert-butyl 3-(2-((2,4-dichloro-3-((2-methoxy-1-(pyridin-2-ylmethyl)-1H-benzo[d]imidazol-4-yloxy)methyl)phenyl)(methyl)amino)-2-oxoethylcarbamoyl)pyrrolidine-1-carboxylate (34)

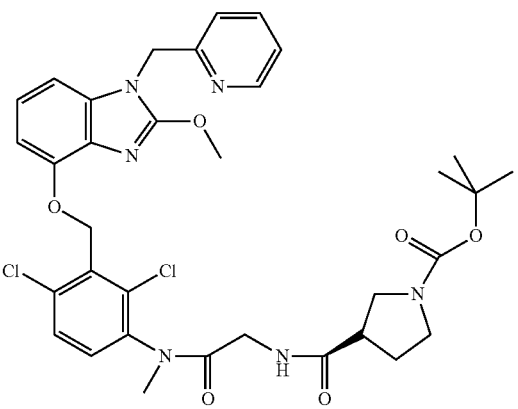

A solution of 2-amino-N-(2,4-dichloro-3-(((2-methoxy-1-(pyridin-2-ylmethyl)-1H-benzo[d]imidazol-4-yl)oxy)methyl)phenyl)-N-methylacetamide (2.00 g, 4 mmol) in anhydrous DMF (12 ml) was treated with HBTU (2.12 g, 5.6 mmol), (S)-1-N-boc-β-proline (0.95 g, 4.4 mmol) and diisopropylethyl amine (2.09 mL, 12 mmol) with stirring at room temperature overnight. To the reaction was added ethyl acetate (200 mL) and the mixture was washed with aqueous saturated sodium bicarbonate (100 mL×3). The organic layer was dried over magnesium sulfate, filtered and evaporated to a tan solid, 2.43 g that was purified by chromatography (silica gel, ethyl acetate and methanol gradient) to afford (S)-tert-butyl 3-(2-((2,4-dichloro-3-((2-methoxy-1-(pyridin-2-ylmethyl)-1H-benzo[d]imidazol-4-yloxy)methyl)phenyl)(methyl)amino)-2-oxoethylcarbamoyl)pyrrolidine-1-carboxylate (34) as a tan solid, 1.68 g (60%), that had one peak by LC/MS (+ESI) m/z 697 (M$^+$+1) and 711 (M$^+$+1) (both ions in the same LC peak), and was pure by $^1$HNMR (400 MHz, CDCl$_3$) δ 8.60 (m, 1H), 7.60 (m, 1H), 7.48 (m, 1H), 7.28 (m, 1H), 7.19 (m, 1H), 7.04 (m, 1H), 6.93 (m, 1H), 6.81 (m, 2H), 6.50 (m, 1H), 5.67 (s, 2H), 5.28 (s, 2H), 4.22 (s, 3H), 3.81 (m, 1H), 3.50 (m, 4H), 3.25 (m, 4H), 2.91 (m, 1H), 2.08 (m, 3H), 1.44 (s, 9H). $^{13}$CNMR (100 MHz, CDCl$_3$) δ 168.2, 156.8, 156.1, 154.3, 149.6, 149.0, 138.4, 138.1, 137.0, 136.5, 135.8, 135.4, 130.1, 129.8, 122.6, 121.7, 120.8, 107.4, 103.1, 79.3, 67.1, 64.3, 60.4, 57.5, 48.6, 47.7, 41.9, 35.9, 30.7, 28.5, 21.0, 19.1, 14.2, 13.7. LN-15495-57.

To obtain an analytical sample, the above method was repeated and the product (0.2 g) was treated with methanol (10 mL) and potassium carbonate (0.2 g) with stirring at room temperature overnight. The mixture was filtered and evaporated to give (S)-tert-butyl 3-(2-((2,4-dichloro-3-((2-methoxy-1-(pyridin-2-ylmethyl)-1H-benzo[d]imidazol-4-yloxy)methyl)phenyl)(methyl)amino)-2-oxoethylcarbamoyl)pyrrolidine-1-carboxylate as white solid, 0.12 g. Anal. Calcd for $C_{34}H_{38}Cl_2N_6O_6$: C, 58.54; H, 5.49; N, 12.05. Found: C, 58.14; H, 5.57; N, 11.80.

Preparation of 1-(2-(2-(((2,4-dichloro-3-((2-methoxy-1-(pyridin-2-ylmethyl)-1H-benzo[d]imidazol-4-yloxy)methyl)phenyl)(methyl)amino)-2-oxoethylamino)-2-oxoethyl)-N-methylpiperidine-3-carboxamide (35)

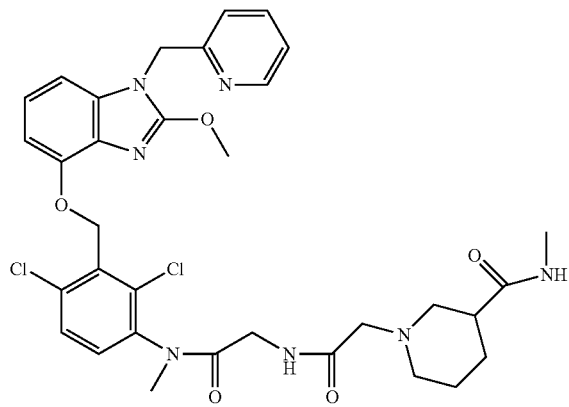

A solution of 2-amino-N-(2,4-dichloro-3-(((2-methoxy-1-(pyridin-2-ylmethyl)-1H-benzo[d]imidazol-4-yl)oxy)methyl)phenyl)-N-methylacetamide (0.45 g, 0.9 mmol) in anhydrous DMF (10 ml) was treated with HBTU (0.48 g, 1.2 mmol), 2-(3-(methylcarbamoyl)piperidin-1-yl)acetic acid (0.20 g, 0.99 mmol) and diisopropylethyl amine (0.47 mL, 2.7 mmol) with stirring at room temperature overnight. To the reaction was added ethyl acetate (100 mL) and the mixture was washed with aqueous saturated sodium bicarbonate (100 mL×3). The organic layer was dried over magnesium sulfate, filtered and evaporated to a sticky yellow residue, 0.63 g that was purified by chromatography (silica gel, dichloromethane and methanol gradient) to afford 1-(2-(2-(((2,4-dichloro-3-((2-methoxy-1-(pyridin-2-ylmethyl)-1H-benzo[d]imidazol-4-yloxy)methyl)phenyl)(methyl)amino)-2-oxoethylamino)-2-oxoethyl)-N-methylpiperidine-3-carboxamide (35) as a white solid, 0.17 g (28%), that was pure by LC/MS (+APCI) m/z 682 (M$^+$+1), $^1$HNMR (400 MHz, CDCl$_3$) δ 8.60 (m, 1H), 7.60 (m, 2H), 7.50 (m, 1H), 7.30 (m, 1H), 7.35 (m, 1H), 7.19 (m, 1H), 7.04 (m, 1H), 6.92 (m, 1H), 6.81 (m, 2H), 6.70 (broad m, 1H), 5.67 (s, 2H), 5.29 (s, 2H), 4.21 (two s, 3H), 4.1 to 1.4 (many multiplets, 19H). $^{13}$CNMR (100 MHz, CDCl$_3$) δ 174.4, 170.5, 168.8, 156.8, 156.1, 149.6, 149.0, 138.4, 138.2, 137.0, 136.5, 135.8, 135.3, 130.3, 122.6, 121.7, 120.8, 107.3, 103.1, 67.0, 61.6, 57.5, 56.5, 56.2, 54.3, 53.4, 47.7, 45.4, 41.3, 36.0, 30.9, 26.3, 26.1, 24.5. Anal. Calcd for C$_{33}$H$_{37}$Cl$_2$N$_6$O$_5$+0.57CH$_2$Cl$_2$: C, 55.16; H, 5.26; N, 13.41. Found: C, 55.18; H, 5.14; N, 13.35.

Preparation of (S)-1-(2-(2-(((2,4-dichloro-3-((2-methoxy-1-(pyridin-2-ylmethyl)-1H-benzo[d]imidazol-4-yloxy)methyl)phenyl)(methyl)amino)-2-oxoethylamino)-2-oxoethyl)-N-methylpiperidine-3-carboxamide (36)

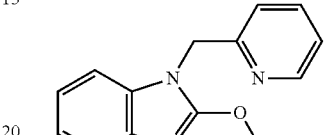

A solution of 2-amino-N-(2,4-dichloro-3-(((2-methoxy-1-(pyridin-2-ylmethyl)-1H-benzo[d]imidazol-4-yl)oxy)methyl)phenyl)-N-methylacetamide (0.45 g, 0.9 mmol) in anhydrous NMP (10 ml) was treated with HBTU (0.48 g, 1.2 mmol), (S)-2-(3-(methylcarbamoyl)piperidin-1-yl)acetic acid (0.21 g, 1.08 mmol) and diisopropylethyl amine (0.47 mL, 2.7 mmol) with stirring at room temperature overnight. To the reaction was added ethyl acetate (100 mL) and the mixture was washed with aqueous saturated sodium bicarbonate (100 mL×3). The organic layer was dried over magnesium sulfate, filtered and evaporated to an off white solid, 0.34 g that was purified by chromatography (silica gel, ethyl acetate and methanol gradient) to afford (S)-1-(2-(2-(((2,4-dichloro-3-((2-methoxy-1-(pyridin-2-ylmethyl)-1H-benzo[d]imidazol-4-yloxy)methyl)phenyl)(methyl)amino)-2-oxoethylamino)-2-oxoethyl)-N-methylpiperidine-3-carboxamide (36) as a white solid, 0.12 g (20%), that was about 90 pure by LC/MS (+APCI) m/z 682 (M$^+$), $^1$HNMR (400 MHz, CDCl$_3$) δ 8.60 (m, 1H), 7.60 (m, 2H), 7.50 (m, 1H), 7.30 (m, 1H), 7.35 (m, 1H), 7.19 (m, 1H), 7.04 (m, 1H), 6.92 (m, 1H), 6.81 (m, 2H), 6.70 (broad m, 1H), 5.67 (s, 2H), 5.29 (s, 2H), 4.21 (s, 3H), 4.1 to 1.4 (many multiplets, 19H). $^{13}$CNMR (100 MHz, CDCl$_3$) δ 174.4, 170.5, 168.8, 156.8, 156.1, 149.6, 149.0, 138.4, 138.2, 137.0, 136.5, 135.8, 135.3, 130.3, 122.6, 121.7, 120.8, 107.3, 103.1, 67.0, 61.6, 57.5, 56.5, 56.2, 54.3, 53.4, 47.7, 45.4, 41.3, 36.0, 30.9, 26.3, 26.1, 24.5.

Preparation of methyl 4-(3-(2-((2,4-dichloro-3-((2-methoxy-1-(pyridin-2-ylmethyl)-1H-benzo[d]imidazol-4-yloxy)methyl)phenyl)(methyl)amino)-2-oxoethylamino)-3-oxopropyl)benzoate (37)

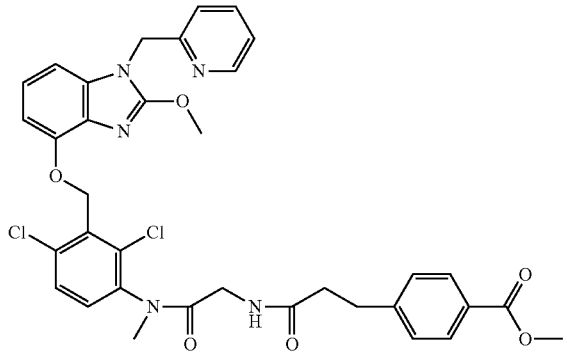

A solution of 2-amino-N-(2,4-dichloro-3-(((2-methoxy-1-(pyridin-2-ylmethyl)-1H-benzo[d]imidazol-4-yl)oxy)methyl)phenyl)-N-methylacetamide (0.45 g, 0.9 mmol) in anhydrous NMP (12 ml) was treated with HBTU (0.48 g, 1.2 mmol), 3-(4-(methoxycarbonyl)phenyl)propanoic acid (0.22 g, 1.08 mmol) and diisopropylethyl amine (0.47 mL, 2.7 mmol) with stirring at room temperature overnight. To the reaction was added ethyl acetate (100 mL) and the mixture was washed with aqueous saturated sodium bicarbonate (100 mL×3). The organic layer was dried over magnesium sulfate, filtered and evaporated to a yellow residue, 0.59 g that was purified by chromatography (silica gel, ethyl acetate and methanol gradient) to afford methyl 4-(3-(2-((2,4-dichloro-3-((2-methoxy-1-(pyridin-2-ylmethyl)-1H-benzo[d]imidazol-4-yloxy)methyl)phenyl)(methyl)amino)-2-oxoethylamino)-3-oxopropyl)benzoate (37) as a white solid, 0.18 g (29%), LC/MS (+APCI) m/z 690 (M$^+$+1) and 704 (M$^+$+1), $^1$HNMR (400 MHz, CDCl$_3$) δ 8.60 (m, 1H), 7.92 (m, 2 H), 7.60 (m, 1H), 7.49 (m, 1H), 7.29 (m, 1H), 7.19 (m, 1H), 7.02 (m, 1H), 6.91 (m, 1H), 6.82 (m, 2H), 6.35 (m, 1H), 5.67 (s, 2H), 5.28 (s, 2H), 4.21 (s, 3H), 3.89 (s, 3H), 4.1 to 2.5 (many multiplets, 10H). $^{13}$CNMR (100 MHz, CDCl$_3$) δ 171.4, 168.2, 156.1, 149.6, 149.0, 146.2, 138.4, 138.1, 137.0, 135.8, 135.3, 130.2, 129.9, 128.4, 128.2, 122.6, 121.7, 120.8, 107.3, 103.0, 67.0, 57.5, 51.9, 47.7, 41.9, 37.4, 35.9, 31.4

(2R,5R)-5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperidine-2-carboxamide and (2S,5R)-5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperidine-2-carboxamide (38 and 39)

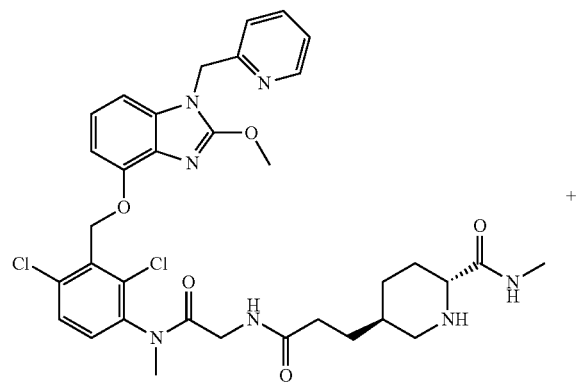

+

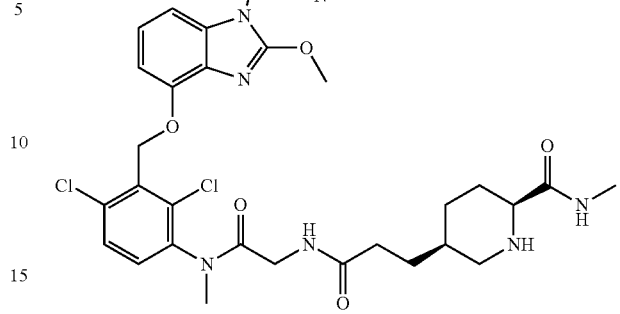

A mixture of tert-butyl 3-(6-(methylcarbamoyl)pyridin-3-yl)propanoate (2.16 g, 8.18 mmol), PtO$_2$ (0.40 g) and 1,1,2-trichloroethane (1.0 mL, 12.4 mmol) in methanol (50 mL) was placed in Parr reactor under 70 psi hydrogen atmosphere for 3.5 days. To the mixture was added 1.25 N HCl/MeOH (6 mL, 7.5 mmol) and the reaction was allowed to continue overnight. The reaction was filtered and evaporated to dryness to give tert-butyl 3-(6-(methylcarbamoyl)piperidin-3-yl)propanoate/HCl salt as a foamy solid (2.80 g). LCMS (+APCI) 271 (M$^+$). The solid give tert-butyl 3-(6-(methylcarbamoyl)piperidin-3-yl)propanoate/HCl was mixed with dichloromethane (100 mL) at 0° C. and to this mixture was added DIPEA (diisopropylethylamine) (6.37 mL) and trifluoroacetic anhydride (3.44 g, 16.4 mmol) with stirring for 30 min. The mixture was warmed to room temperature, stirred for 30 min and evaporated to dryness. The crude was neutralized with a saturated aqueous sodium bicarbonate solution (100 mL) and extracted with ethyl acetate. Evaporation gave tert-butyl 3-(6-(methylcarbamoyl)-1-(2,2,2-trifluoroacetyl)piperidin-3-yl)propanoate as an oil that was purified by silica chromatography eluting with a gradient of 5% to 100% EtOAc/Hex then 0% to 10% MeOH/EtOAc to give 0.84 g of the ester as an oil. LCMS (+APCI) 367 (M+1).

tert-butyl 3-(6-(methylcarbamoyl)-1-(2,2,2-trifluoroacetyl)piperidin-3-yl)propanoate was treated with trifluoroacetic acid (5 mL) for 10 min, evaporated to dryness and placed in vacuum overnight. The crude 3-(6-(methylcarbamoyl)-1-(2,2,2-trifluoroacetyl)piperidin-3-yl)propanoic acid was mixed with dichloromethane (30 min) and to this mixture was added DIPEA (3 mL), 2-amino-N-(2,4-dichloro-3-(((2-methoxy-1-(pyridin-2-ylmethyl)-1H-benzo[d]imidazol-4-yl)oxy)methyl)phenyl)-N-methylacetamide (1.03 g, 2.07 mmol) and HBTU (1.13 g, 2.99 mmol) with stirring. The mixture was stirred for 1 h and was added a saturated aqueous sodium bicarbonate solution (100 mL) and extracted with dichloromethane. The combined extracts was dried and evaporated to dryness. Silica chromatography eluting with a gradient of 3% to 10% of MeOH/DCM gave a mixture of (2R,5R)-5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperidine-2-carboxamide and (2S,5R)-5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperidine-2-carboxamide, 1.01 g as a foamy solid (62%). LCMS (+ESI) 792 (M$^+$).

The mixture of (2R,5R)-5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperidine-2-carboxamide and (2S,5R)-5-(3-((2-((2,4-dichloro-3-(((2-methoxy-1-(pyridin-2- ylmethyl)-1H-benzo[d]imidazol-4-yl)oxy)methyl)phenyl)(methyl)amino)-2-oxoethyl)amino)-3-oxopropyl)-N-methylpiperidine-2-carboxamide (1.01 g, 1.27 mmol) was diluted with ethanol (20 mL). To the solution was added NaBH$_4$ (10% on Al$_2$O$_3$, 0.48 g, 1.27 mmol) with stirring. After 1.5 h a saturated aqueous sodium bicarbonate solution (50 mL) was added and the mixture was extracted with dichloromethane. Evaporation gave a crude mixture that was separated by chromatography eluting with a gradient of 10% to 40% MeOH/DCM to give two isomers (0.19 g and 0.12 g respectively). NMR analysis showed the first isomer was the cis-isomer (2S,5R)-5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperidine-2-carboxamide and the second isomer was the trans-isomer (2R,5R)-5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperidine-2-carboxamide. 2S,5R (cis) isomer: LCMS (+APCI) 696 (M+1). $^1$H-NMR (CDCl$_3$, δ ppm): 8.58 (d, J=4.0 Hz, 1H), 7.58 (m, 1H), 7.47 (d, J=8.4 Hz, 1H), 7.28 (d, J=8.4 Hz, 1H), 7.19 (m, 1H), 7.04 (t, J=8.0 Hz, 1H), 6.92 (d, J=7.6 Hz, 1H), 6.80 (dd, 1H), 6.48 (bs, 1H), 6.38 (bt, 1H), 5.66 (dd, 2H), 5.28 (s, 2H), 4.21 (s, 3H), 3.82 (dt, 1H), 3.50 (dt, 1H), 3.35 (t, 1H), 3.25 (s, 3H), 2.81 (d, J=4.8 Hz, 3H), 2.80 (m, 1H), 2.48 (m, 1H), 2.22 (m, 2H), 2.07 (m, 1H), 1.69 (m, 1H), 1.60 (m, 1H), 1.50 (m, 1H), 1.39 (m, 1H), 1.29 (m, 1H). Calcd. for C$_{34}$H$_{39}$Cl$_2$N$_7$O$_5$+1.8H$_2$O: C, 56.01; H, 5.89; N, 13.45. Found: C, 56.04; H, 5.59; N, 13.15. 2R,5R (trans isomer) $^1$H-NMR (CDCl$_3$, δ ppm): 8.59 (d, J=4.0 Hz, 1H), 7.59 (m, 1H), 7.47 (d, J=8.4 Hz, 1H), 7.28 (d, J=8.8 Hz, 1H), 7.19 (m, 1H), 7.03 (t, J=8.0 Hz, 1H), 6.92 (d, 1H), 6.80 (dd, J=13.8, 7.6 Hz, 2H), 6.63 (bs, 1H), 6.38 (bt, 1H), 5.66 (dd, 2H), 5.28 (s, 2H), 4.21 (s, 3H), 3.82 (dd, J=4.4, 17.6 Hz, 1H), 3.50 (dd, J=3.6, 18.0 Hz, 1H), 3.25 (s, 3H), 3.11 (dd, J=2.8, 11.2 Hz, 1H), 3.07 (m, 1H), 2.78 (d, J=4.8 Hz, 3H), 2.28 (t, J=11.2 Hz, 1H), 2.23 (m, 2H), 2.07 (m, 1H), 1.99 (bd, J=13.6 Hz, 1H), 1.50 (m, 2H), 1.37 (m, 1H), 1.28 (m, 1H), 1.05 (m, 1H). Calcd. for C$_{34}$H$_{39}$Cl$_2$N$_7$O$_5$+1.8H$_2$O: C, 56.01; H, 5.89; N, 13.45. Found: C, 56.15; H, 5.63; N, 13.18.

4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2,2-difluoro-3-oxopropyl)-N-methylpiperazine-1-carboxamide (40)

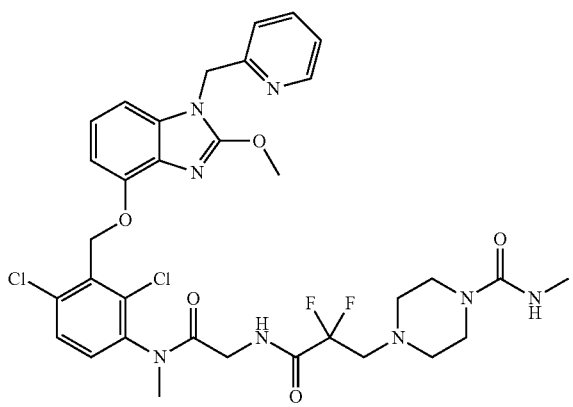

Benzotriazolmethanol (5.00 g, 33.5) and t-boc-piperazine (6.70 g, 33.5) were stirred in methanol at room temperature for 2 h to give 4-benzotriazol-ylmethylpiperazine-1-carboxylic acid tert-butyl ester. This solid was filtered and crystallized from methanol.

To a suspension of zinc dust (1.93 g, 29.5 mmol) in dry THF (30 mL), under nitrogen, was added TMS-Cl (trimethylsilyl chloride) (1.28 g, 11.8 mmol). The reaction mixture was stirred for 15 min, and then ethylbromodifluoroacetate (4.49 g, 22.1 mmol) was slowly added, followed 15 min later by a solution 4-benzotriazol-ylmethylpiperazine-1-carboxylic acid tert-butyl ester (4.68 g, 14.8 mmol). After, 3 h stirring at room temperature, the mixture was poured onto 5% aqueous NaHCO$_3$ (40 mL) and filtered on celite. The filtrate was diluted with ethyl acetate and organic layer was separated, dried (MgSO$_4$) and concentrated to give an oil which was purified by flash chromatography (Hexane-Ethyl acetate (8:2) to give 1.05 g of 4-(2-ethoxycarbonyl-2,2-difluoro-ethyl)-piperazine-1-carboxylic acid tert-butyl ester as an oil.

$^1$HNMR (400 MHz, CDCl$_3$) δ 1.37 (t, 3H), 1.44 (s, 9H), 2.58 (m, 4H), 3.01 (dd, 2H), 3.38 (m, 4H), 4.35 (q, 2H)

4-(2-ethoxycarbonyl-2,2-difluoro-ethyl)-piperazine-1-carboxylic acid tert-butyl ester prepared was dissolved in dichloromethane (10 mL) and TFA (5 mL). The solution was stirred for 2 h at room temperature, concentrated to dryness, and dissolved in dichloromethane (20 mL) and triethylamine (0.69 g, 6.84 mmol), after stirring for 5 min, a solution of methylaminoformyl chloride (0.34 g, 3.64 mmol) was slowly added. The reaction mixture was stirred for 2 h, diluted with dichloromethane (100 mL), washed with aqueous solution of NaHCO$_3$. Organic layer was dried (MgSO$_4$), and concentrated to ethyl 2,2-difluoro-3-(4-(methylcarbamoyl)piperazin-1-yl)propanoate as an oil, which was purified by flash chromatograph using ethyl acetate.

$^1$HNMR (400 MHz, CDCl$_3$) δ 1.37 (t, 3H), 2.59 (m, 4H), 2.79 (d, 3H), 2.99 (dd, 2H), 3.3 (m, 4H), 4.31 (q, 2H)

To ethyl 2,2-difluoro-3-(4-(methylcarbamoyl)piperazin-1-yl)propanoate (1.0 g, 3.7 mmol) in THF (15 mL) and water (18 mL) was added LiOH (0.6 g, 14.29 mmol), after 18 h stirring at room temperature, the volatiles were removed by high vacuum and the solid residue 2,2-difluoro-3-(4-(methylcarbamoyl)piperazin-1-yl)propanoic acid was used without further purification. LCMS 250 [M−H]$^-$ 2,2-difluoro-3-(4-(methylcarbamoyl)piperazin-1-yl)propanoic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide are coupling using TBTU as described for compound 1 to give 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2,2-difluoro-3-oxopropyl)-N-methylpiperazine-1-carboxamide. LCMS (APCI) 733 (M$^+$).

$^1$HNMR (400 MHz, MeOD) δ 2.48 (m, 4H), 2.59 (s, 3H), 2.89 (t, 3H), 3.11 (m, 3H), 3.21 (s, 3H), 3.5-3.76 (m, 2H), 4.03 (s, 3H), 5.21 (s, 2H), 5.48 (m, 2H), 6.74 (m, 2H), 6.93 (m, 2H), 6.97 (m, 1H), 7.50 (m, 2H), 7.64 (m, 1H), 8.40 (d, 1H).

5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methyl-1,4,5,6-tetrahydropyrimidine-2-carboxamide (41)

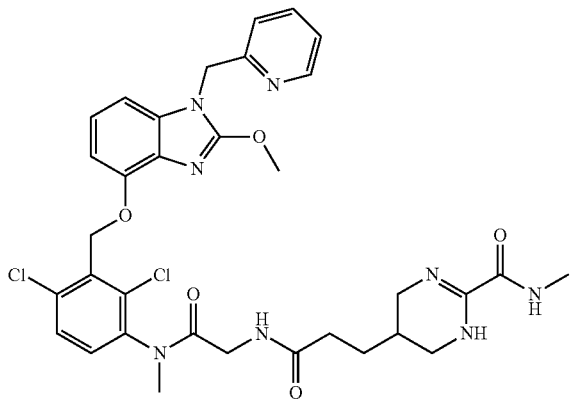

To a solution of 5-bromopyrimidine-2-carboxylic acid methyl ester (5.0 g, 23.0 mmol) in THF (10 mL) was added 8 N solution of methyl amine in ethanol (11.5 mL). The reaction mixture was heated 20 min in a microwave oven, cooled down to room temperature and concentrated under pressure to give 5 g of 5-bromo-N-methylpyrimidine-2-carboxamide as a solid LCMS: 216, 218 (M+1).

To a solution of 5-bromo-N-methylpyrimidine-2-carboxamide (0.14 g, 0.64 mmol) in DMF (5 mL) was added acrylic acid benzyl ester (0.13 g, 0.78 mmol), Pd(OAc)$_2$ (14.3 mg), tri-o-tolyl phosphine (49 mg, 0.16 mmol), tributyl amine (0.48 g, 2.59 mmol). The reaction mixture was heated in microwave oven at 110° C. for 1 h. The reaction mixture was cooled to room temperature, partitioned in water (50 mL) and ethyl acetate (50 mL). Ethyl acetate layer was separated, dried (MgSO$_4$), concentrated to give 3-(2-methylcarbamoyl-pyrimidin 5-yl)acrylic acid benzyl ester as a solid, this was washed with hexanes and dried to give the 0.122 g of the product. LCMS (APCI) 298 (M$^+$)

3-(2-methylcarbamoyl-pyrimidin 5-yl)acrylic acid benzyl ester was dissolved in ethanol (20 mL) in presence of 15 mg of Pd/C, 10% and HCl$_c$ (2 mL). The mixture was stirred under hydrogen balloon overnight to give 3-(2-methylcarbamoyl-pyridine-5-yl)-propionic acid which was used without further purification.

3-(2-methylcarbamoyl-pyridine-5-yl)-propionic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide were coupled as described for compound 1. MS (APCI) 695 (M$^+$), $^1$HNMR (400 MHz, MeOD) δ 1.57-1.69 (m, 3H), 2.31 (m, 2H), 2.78 (s, 3H), 2.98 (m, 2H), 3.19 (s, 3H), 3.34-3.824 (m, 4H), 4.30 (s, 3H), 5.30 (s, 2H), 5.55 (m, 2H), 6.83 (m, 2H), 7.05 (m, 2H), 7.30 (m, 1H), 7.57 (m, 2H), 7.63 (m, 1H), 8.49 (d, 1H). C$_{33}$H$_{36}$Cl$_2$N$_8$O$_5$+0.4 H$_2$O, Calculated: C, 56.4; H, 5.28; N, 15.94. Found: C, 56.4; H, 5.35; N, 15.90.

5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpyrimidine-2-carboxamide (42)

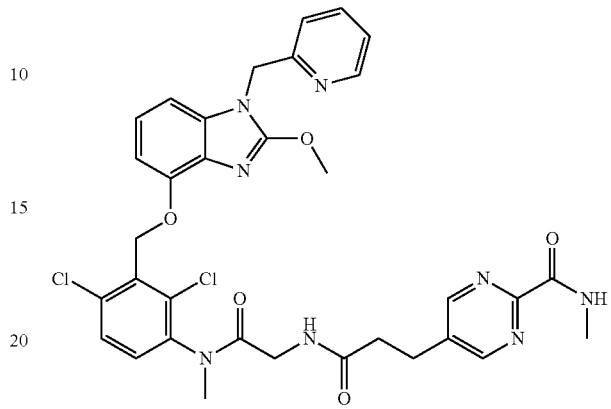

3-(2-methylcarbamoyl-pyrimidin 5-yl)acrylic acid benzyl ester in ethanol (20 mL) in presence of 15 mg of Pd/C, 10%, and stirred under hydrogen balloon overnight to give 3-(2-methylcarbamoyl-pyrimidine-5-yl)-propionic acid which was used without further purification.

3-(2-methylcarbamoyl-pyridine-5-yl)-propionic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide and coupled together as described for compound 1 above. LCMS (APCI) 691 (M+1); $^1$HNMR (400 MHz, MeOD) δ 2.90-3.0 (m, 5H), 3.21-3.25 (m, 5H), 3.66 (d, 1H), 3.96 (d, 1H), 4.15 (s, 3H), 5.33 (s, 2H), 5.58 (m, 2H), 6.86 (m, 2H), 7.08 (m, 2H), 7.32 (m, 1H), 7.55-762(m, 2H), 7.76 (m, 1H), 8.51 (d, 1H), 9.08 (s, 2H)

6-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylnicotinamide (43)

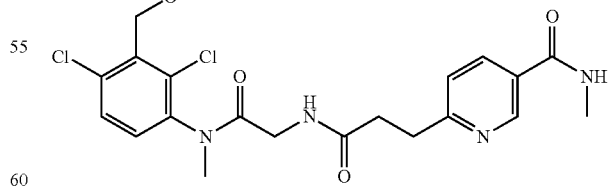

Methyl 6-formylnicotinate (1.0 g, 6.06 mmol) and tert-butyl (triphenylphosphoranylidene)acetate (2.73 g, 7.27 mmol) were put in suspension in water (50 mL) and stirred at 90° C. for 2 h. The reaction mixture was cooled to room temperature and concentrated under pressure. The residue was triturated in ethyl acetate and filtered. The filtrate was concentrated and purified by flash chromatography using hexanes-ethyl acetate 10% to give (E)-methyl 6-(3-(tert-butoxy)-3-oxoprop-1-en-1-yl)nicotinate. MS (APCI) 264 (M+). (E)-methyl 6-(3-(tert-butoxy)-3-oxoprop-1-en-1-yl)nicotinate was dissolved in ethanol in the presence of 50 mg Pd/C, 10% and stirred under hydrogen balloon overnight to give 6-2(tert-butoxycarbonyl-ethyl)nicotinic methyl ester. LCMS: 266 (M+)

To a solution of 6-2(tert-butoxycarbonyl-ethyl)nicotinic methyl ester (1.7 g, 6.4 mmol) in methanol (10 mL) was added 3.2 mL of 8 N solution of methyl amine in methanol. The reaction vial was sealed and stirred at 70° C. overnight, cooled to room temperature and concentrated under reduced pressure. The residue was purified by flash chromatography using ethyl acetate to give tert-butyl-3(5-methylcarbamoyl pyridine-2-yl) propionate. LCMS 265 (M+1)

tert-Butyl-3(5-methylcarbamoyl-pyridin-2-yl)propionate (0.29 g, 1.10 mmol) was dissolved in 10 mL of a 4 N hydrogen chloride solution in dioxane and stirred overnight. Evaporation of the solvent gave 0.27 mg of 3(5-methylcarbamoyl-pyridin-2-yl)propionic acid hydrochloride. LCMS 209 (M+1)

To a suspension of 3(5-methylcarbamoyl-pyridin-2-yl) propionic acid hydrochloride (0.26 g, 1.06 mmol) in dichloromethane (20 mL) was added ethyldiisopropylamine (0.74 mL, 4.26 mmol), the solution was stirred for 5 min, and then 2-amino-N-(2,4-dichloro-3-(((2-methoxy-1-(pyridin-2-ylmethyl)-1H-benzo[d]imidazol-4-yl)oxy)methyl)phenyl)-N-methylacetamide (0.5 g, 1.0 mmol) was added followed by HOBT (0.135 g, 1.0 mmol) and EDCI (0.28 mL, 1.59 mmol). The reaction mixture was then stirred overnight at room temperature and partitioned in dichloromethane (100 mL) and a saturated solution of NaHCO$_3$ (100 mL). Organic layer was separated, dried (MgSO$_4$) and concentrated to give oil, which was purified by flash chromatography using a mixture of dichloromethane- and a 5% ammonium solution in methanol (9:1) to give 6-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylnicotinamide as foam. LCMS (APCI) 690 (M+); $^1$HNMR (400 MHz, MeOD) δ 2.60 (t, 2H), 3.07 (s, 3H), 3.19 (t, 2H), 3.20 (s, 3H), 3.32-3.69 (dd, 2H), 4.01 (s, 3H), 5.19 (s, 2H), 5.46 (dd, 2H), 6.71-8.74 (m, 12H)

4-(2-((2-((2,4-dichloro-3-(((2-methoxy-1-(pyridin-2-ylmethyl)-1H-benzo[d]imidazol-4-yl)oxy)methyl) phenyl)(methyl)amino)-2-oxoethyl)amino)-2-oxoethyl)-N-methylmorpholine-2-carboxamide (44)

To a cold solution (ice bath) of N-Boc-2-morpholinecarboxylic acid (0.5 g, 2.16 mmol) in DMF (10 mL) was added HATU ((2-(7-Aza-1H-benzotriazole-1-yl)-1,1,3,3-tetramethyluronium hexafluorophosphate) (0.98 g, 2.58 mmol), N,N diisopropylethylamine (2.2 g, 17.3 mmol), and 1 mL of 8 N solution of methylamine in ethanol. After the addition was finished the ice bath was removed, and the heterogeneous solution was stirred overnight at room temperature. The solution was dissolved in ethyl acetate (50 mL) and washed with a saturated solution of NaHCO$_3$. Ethyl acetate layer was separated, dried (MgSO$_4$) and concentrated under reduced pressure to give tert-butyl 2-(methylcarbamoyl)morpholine-4-carboxylate as an oil. MS (APCI) 245 (M+)

tert-butyl 2-(methylcarbamoyl)morpholine-4-carboxylate prepared above (0.5 g, 0.20 mmol) was dissolved in DCM (10 mL) and TFA (2 mL). The reaction mixture was stirred at room temperature for 4 h and then concentrated; excess 1N HCl solution in ether was added to the residue and concentrated under high vacuum. The residue was dissolved in acetonitrile (20 mL) and K$_2$CO$_3$ (0.56 g, 40.8 mmol) was added followed by bromo-acetic acid benzyl ester (0.7 g, 3.07 mmol). The reaction mixture was heated at 60° C. overnight. The solution was cooled to room temperature and diluted with Ethyl acetate (50 mL) and water (50 mL), organic layer was separated, dried (MgSO$_4$) and concentrated to give an oil which was purified by column chromatography using ethyl acetate-hexanes (1:1) to give benzyl 2-(2-(methylcarbamoyl) morpholino)acetate. MS (APCI) 293 (M+).

benzyl 2-(2-(methylcarbamoyl)morpholino)acetate was dissolved in ethanol (40 mL), Pd/C 10% (100 mg) was added to the solution, and the mixture was stirred overnight under hydrogen (balloon) then filtered through celite and concentrated to give 2-(2-(methylcarbamoyl)morpholino)acetic acid. MS (APCI) 203 (M+1)

2-(2-(methylcarbamoyl)morpholino)acetic acid and 2-amino-N-(2,4-dichloro-3-(((2-methoxy-1-(pyridin-2-ylmethyl)-1H-benzo[d]imidazol-4-yl)oxy)methyl)phenyl)-N-methylacetamide were coupled using EDCI to give 4-(2-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2-oxoethyl)-N-methylmorpholine-2-carboxamide. MS (APCI) 684 (M+); $^1$H NMR (CDCl$_3$) 2.26-2.40 (m, 1H), 2.61-2.82 (m, 4H), 2.95-3.15 (m, 2H), 3.15-3.28 (m, 4H), 3.40-3.49 (m, 1H), 3.61-3.91 (m, 2H), 3.90-4.01 (m, 1H), 4.08-4.18 (m, 1H), 4.22 (s, 3H), 5.28 (s, 2H), 5.62-5.70 (m, 2H), 6.51-6.58 (m, 1H), 6.75-6.87 (m, 2H), 6.91 (d, 1H, J=5.7 Hz), 7.02-7.06 (t, 1H, J=6.2 Hz), 7.19-7.21 (m, 1H), 7.31-7.33 (m, 1H), 7.46-7.49 (m, 1H), 7.55-7.62 (m, 1H), 7.78-7.90 (m, 1H), 8.57 (m, 1H). C$_{32}$H$_{35}$Cl$_2$N$_7$O$_6$+0.8 H$_2$O, Calculated: C, 54.97; H, 5.28; N, 14.03. Found: C, 54.99; H, 5.20; N, 13.85.

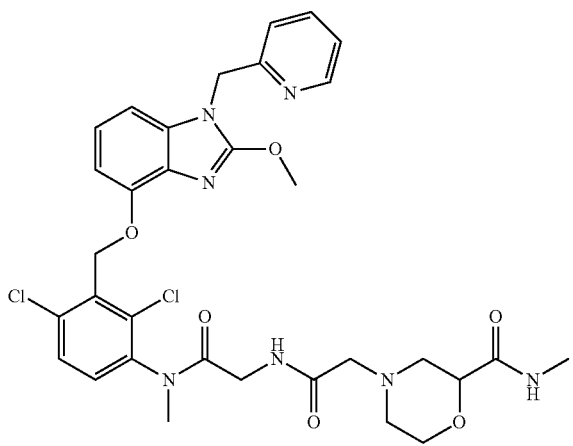

(S)-4-(2-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2-oxoethyl)-N-methylmorpholine-2-carboxamide (45)

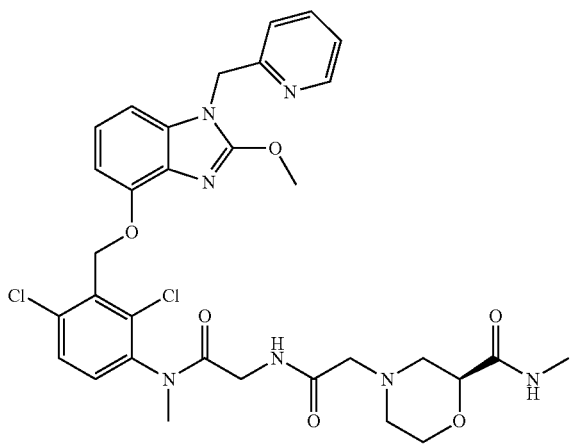

(S)-4-(2-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2-oxoethyl)-N-methylmorpholine-2-carboxamide was prepared from N-Boc-2S-morpholinecarboxylic acid as described for the 44 above. MS (APCI) 684 (M+)

$^1$HNMR (400 MHz, MeOD) δ 2.18-224(m, 2H), 2.64 (s, 3H), 2.66 (t, 1H), 3.11 (m, 3H), 3.23 (s, 3H), 3.5-4.10 (m, 5H), 4.16 (s, 3H), 5.21 (s, 2H), 5.46 (m, 2H), 6.76 (m, 2H), 6.99 (m, 2H), 7.22 (m, 1H), 7.48 (m, 2H), 7.66 (m, 1H), 8.39 (d, 1H).

Preparation of ethyl 2-((8-((2,6-dichloro-3-(N-methyl-2-(3-(6-(methylcarbamoyl)pyridin-3-yl)propanamido)acetamido)benzyl)oxy)-2-methylquinolin-4-yl)oxy)acetate (46)

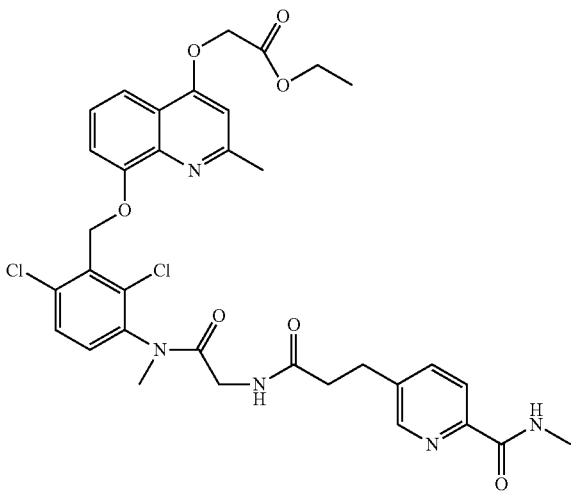

To 4-chloro-2-methylquinolin-8-ol (10.20 g, 52.7 mmol), potassium carbonate (10.9 g, 79.0 mmol) in 2-butanone (100 mL) was added benzyl bromide (6.89 mL, 58.0 mmol) vial syringe with stirring. The suspension was heated at 70° C. for 4 h, stirred at ambient temperature overnight and poured into ice water (200 mL). The precipitate was filtered, washed with a little EtOAc/water and dried to give 8-(benzyloxy)-4-chloro-2-methylquinoline (5.82 g). The filtrate was extracted with EtOAc, dried, filtered and evaporated. Solid from Hex/EtOAc (10/1) was filtered and dried to give additional 8-(benzyloxy)-4-chloro-2-methylquinoline, 13.72 g (92% total crude yield).

To a mixture of 8-(benzyloxy)-4-chloro-2-methylquinoline (3.09 g, 10.9 mmol), potassium carbonate (3.22 g, 32.8 mmol) in DMSO (30 mL) was added water (1.00 mL) to dissolve the solid. The mixture was heated at 140° C. for 2 h and was added 2N NaOH (12 mL, 24.0 mmol) and heated at 130° C. overnight. The mixture was poured into ice/NaHCO$_3$. Solid precipitated and was filtered, washed with water and dried to give 8-(benzyloxy)-2-methylquinolin-4-ol (2.34 g, 81%).

To a mixture of give 8-(benzyloxy)-2-methylquinolin-4-ol (2.34 g, 8.83 mmol) and potassium carbonate (1.83 g, 13.2 mmol) in anhydrous DMF (50 mL) was added ethyl bromoacetate (1.77 g, 10.6 mmol) with stirring under nitrogen. The mixture was heated at 80° C. for 1 h, cooled, mixed with a saturated aqueous sodium bicarbonate and extracted with EtOAc. Evaporation gave a crude product that was dissolved in dichloromethane and precipitated by the addition of a mixture of Hex/EtOAc (10/1). The precipitate was filtered and dried to give ethyl 2-((8-(benzyloxy)-2-methylquinolin-4-yl)oxy)acetate (2.13 g, 69%). A mixture of ethyl 2-((8-(benzyloxy)-2-methylquinolin-4-yl)oxy)acetate (0.70 g, 1.99 mmol), Pd/C (10%, 0.07 g) in EtOH/dioxane (20 mL/20 mL) was placed under hydrogen atmosphere with stirring overnight. The mixture was filtered and evaporated to give ethyl 2-((8-hydroxy-2-methylquinolin-4-yl)oxy)acetate (0.24 g, 46%).

To a mixture of 2-((8-hydroxy-2-methylquinolin-4-yl)oxy)acetate (0.24 g, 0.92 mmol) and 5-(3-((2-((2,4-dichloro-3-(chloromethyl)phenyl)(methyl)amino)-2-oxoethyl)amino)-3-oxopropyl)-N-methylpicolinamide (0.28 g, 0.61 mmol) in anhydrous DMF (30 mL) was added potassium carbonate (0.25 g, 1.8 mmol). The mixture was heated at 80° C. for 3 h, cooled, mixed with a saturated aqueous sodium bicarbonate and extracted with EtOAc. The crude mixture was purified by silica chromatography eluting twice with a gradient of 3% to 25% of MeOH/DCM and a gradient of 5% to 15% of MeOH/DCM to give ethyl 2-((8-((2,6-dichloro-3-(N-methyl-2-(3-(6-(methylcarbamoyl)pyridin-3-yl)propanamido)acetamido)benzyl)oxy)-2-methylquinolin-4-yl)oxy)acetate as a powder (0.16 g, 38%) after drying at high vacuum at 78° C. overnight. LCMS (+ESI) 696 (M+1). $^1$H-NMR (CDCl$_3$, δ): 8.37 (s, 1H), 8.08 (d, J=8.0 Hz, 1H), 7.95 (bs, 1H), 7.91 (d, J=7.2 Hz, 1H), 7.63 (m, 1H), 7.46 (d, J=8.4 Hz, 1H), 7.38 (t, J=8.0 Hz, 1H), 7.25 (m, 3H), 6.50 (s, 1H), 6.40 (bt, 1H), 5.62 (s, 2H), 4.82 (s, 2H), 4.31 (q, J=7.2 Hz, 2H), 3.76 (dd, J=4.8, 18 Hz, 1H), 3.43 (dd, J=4.0, 18 Hz, 1H), 3.21 (s, 3H), 3.01 (m, 6H), 2.66 (s, 3H), 2.54 (t, J=7.6 Hz, 2H), 1.30 (t, J=7.2 Hz, 3H). Calcd. for $C_{34}H_{35}Cl_2N_5O_7$+ 0.7H$_2$O: C, 57.58; H, 5.17; N, 9.88. Found: C, 57.30; H, 5.30; N, 10.11.

5-(3-((2-((2,4-dichloro-3-(((4-((2-fluorobenzyl)oxy)-2-methylquinolin-8-yl)oxy)methyl)phenyl)(methyl)amino)-2-oxoethyl)amino)-3-oxopropyl)-N-methylpicolinamide (47)

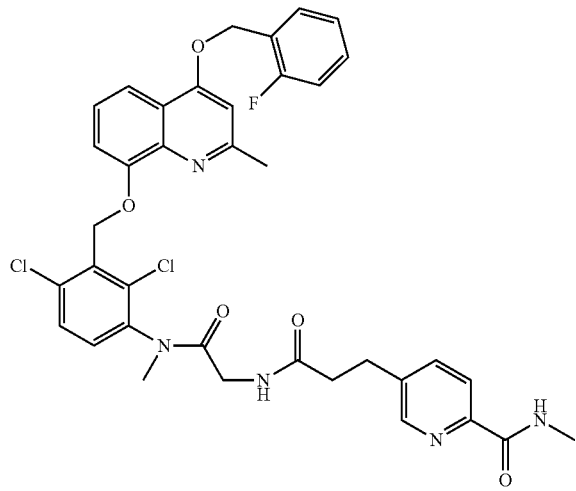

To a stirred solution of 2-fluorobenzyl alcohol (1.95 g, 15.5 mmol) in anhydrous DMF (35 mL) was added sodium hydride (60% in mineral oil, 0.62 g, 15.5 mmol). After 30 min the 4-chloro-2-methylquinolin-8-ol (1.00 g, 5.16 mmol) was added and resulting mixture was heated at 130° C. for 20 h under nitrogen atmosphere. The mixture was cooled, poured into ice/NaHCO$_3$ and extracted with EtOAc. Evaporation gave a crude oil that was purified by silica chromatography eluting with a gradient of 1% to 10% of MeOH/DCM to give 44(2-fluorobenzyl)oxy)-2-methylquinolin-8-ol as an oil that solidified on standing (0.39 g, 27%). LCMS (+APCI) 284 (M+1), mp 124-125° C. $^1$H-NMR (CDCl$_3$, δ): 7.75 (d, J=8.4 Hz, 1H), 7.50 (d, J=7.6 Hz, 2H), 7.43 (s, 1H), 7.35 (m, 3H), 7.20 (d, J=7.6 Hz, 1H), 7.06 (d, J=8.0 Hz), 5.45 (s, 2H), 2.78 (s, 3H).

4-((2-fluorobenzyl)oxy)-2-methylquinolin-8-ol from step 1 was reacted with 5-(3-((2-((2,4-dichloro-3-(chloromethyl)phenyl)(methyl)amino)-2-oxoethyl)amino)-3-oxopropyl)-N-methylpicolinamide as described previously to give 5-(3-((2-((2,4-dichloro-3-(((4-((2-fluorobenzyl)oxy)-2-methylquinolin-8-yl)oxy)methyl)phenyl)(methyl)amino)-2-oxoethyl)amino)-3-oxopropyl)-N-methylpicolinamide in 53% yield. MS (+APCI) 718 (M$^+$). $^1$H-NMR (CDCl$_3$, δ ppm): 8.36 (s, 1H), 8.07 (d, J=8.0 Hz, 1H), 7.95 (bd, 1H), 7.94 (d, J=8.0 Hz, 1H), 7.63 (m, 1H), 7.58 (m, 1H), 7.45 (d, J=8.4 Hz, 1H), 7.36 (t, J=8.0 Hz, 1H), 7.25 (m, 4H), 7.15 (m, 1H), 7.05 (m, 1H), 6.77 (bs, 1H), 6.40 (bt, 1H), 5.62 (s, 2H), 5.38 (s, 2H), 3.76 (dd, J=5.2, 17.6 Hz, 1H), 3.46 (dd, J=3.6, 18 Hz, 1H), 3.22 (s, 3H), 3.00 (m, 6H), 2.69 (m, 2H), 2.56 (t, 2).

5-(3-((2-((2,4-dichloro-3-(((2-methyl-4-((1-methyl-1H-imidazol-4-yl)methoxy)quinolin-8-yl)oxy)methyl)phenyl)(methyl)amino)-2-oxoethyl)amino)-3-oxopropyl)-N-methylpicolinamide (48)

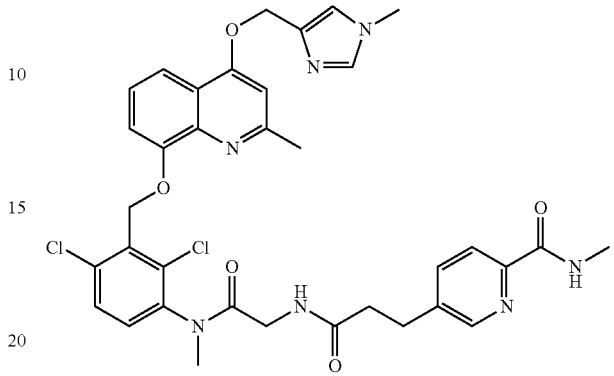

5-(3-((2-((2,4-dichloro-3-(((2-methyl-4-((1-methyl-1H-imidazol-4-yl)methoxy)quinolin-8-yl)oxy)methyl)phenyl)(methyl)amino)-2-oxoethyl)amino)-3-oxopropyl)-N-methylpicolinamide was prepared from 2-methyl-4-((1-methyl-1H-imidazol-4-yl)methoxy)quinolin-8-ol and 5-(3-((2-((2,4-dichloro-3-(chloromethyl)phenyl)(methyl)amino)-2-oxoethyl)amino)-3-oxopropyl)-N-methylpicolinamide as previously described. MS (+ESI) 704 (M+1). $^1$H-NMR (CDCl$_3$, δ ppm): 8.36 (s, 1H), 8.08 (d, J=8.0 Hz, 1H), 7.94 (bs, 1H), 7.98 (dd, J=1.2, 9.2 Hz, 1H), 7.64 (dd, J=2.4, 8.4 Hz, 1H), 7.44 (m, 2H), 7.25 (m, 3H), 7.02 (s, 1H), 6.82 (s, 1H), 6.49 (bt, 1H), 5.61 (s, 2H), 5.22 (s, 2H), 3.75 (dd, 1H), 3.71 (s, 3H), 3.38 (dd, J=4, 17.6 Hz, 1H), 3.20 (s, 3H), 3.01 (d, J=5.2 Hz, 3H), 2.99 (m, 2H), 2.67 (s, 3H), 2.54 (t, J=7.6 Hz, 2H). 4-(3-((2-((2,4-dichloro-3-(((2-methyl-4-((1-methyl-1H-imidazol-2-yl)methoxy)quinolin-8-yl)oxy)methyl)phenyl)(methyl)amino)-2-oxoethyl)amino)-3-oxopropyl)-N-methylbenzamide was prepared from 2-methyl-4-((1-methyl-1H-imidazol-2-yl)methoxy)quinolin-8-ol and 5-(3-((2-((2,4-dichloro-3-(chloromethyl)phenyl)(methyl)amino)-2-oxoethyl)amino)-3-oxopropyl)-N-methylpicolinamide as previously described. LCMS (+ESI) 704 (M$^+$).

5-(3-((2-((2,4-dichloro-3-(((2-methyl-4-((pyridin-2-ylmethyl)amino)quinolin-8-yl)oxy)methyl)phenyl)(methyl)amino)-2-oxoethyl)amino)-3-oxopropyl)-N-methylpicolinamide (49)

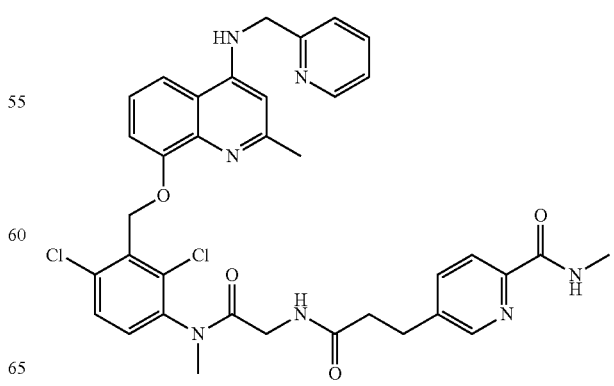

A mixture of the 4-chloro-2-methylquinolin-8-ol (2.00 g, 10.3 mmol) and 2-aminomethyl pyridine (3.35 g, 30.9 mmol) in DMSO (5 mL) was heated at 160° C. for 2 h under nitrogen atmosphere. The mixture was cooled, poured into ice/NaHCO$_3$ and extracted with ethyl acetate and dichloromethane. Evaporation gave a crude mixture that was mixed with ethyl acetate. The yellow solid precipitated and was filtered and dried to give 1.20 g of 2-methyl-4-((pyridin-2-ylmethyl)amino)quinolin-8-ol (44%). MS (+APCI) 266 (M$^+$). $^1$H-NMR (CDCl$_3$, δ): 8.56 (m, 1H), 7.79 (t, J=6.0 Hz, 1H), 7.75 (dt, J=2.0, 7.6 Hz, 1H), 7.63 (dd, J=1.2, 8.4 Hz, 1H), 7.34 (d, J=7.6 Hz, 1H), 7.25 (m, 2H), 6.96 (d, J=7.6 Hz, 1H), 6.29 (s, 1H), 4.62 (d, J=6.0 Hz, 2H), 2.41 (s, 3H).

2-methyl-4-((pyridin-2-ylmethyl)amino)quinolin-8-ol and 5-(3-((2-((2,4-dichloro-3-(chloromethyl)phenyl)(methyl)amino)-2-oxoethyl)amino)-3-oxopropyl)-N-methylpicolinamide were reacted as previously described to give 5-(3-((2-((2,4-dichloro-3-(((4-((2-fluorobenzyl)amino)-2-methylquinolin-8-yl)oxy)methyl)phenyl)(methyl)amino)-2-oxoethyl)amino)-3-oxopropyl)-N-methylpicolinamide in 39% yield. MS (+ESI) 700 (M$^+$). $^1$H-NMR (CDCl$_3$, δ): 8.64 (s, 1H), 8.35 (d, J=1.6 Hz, 1H), 8.07 (d, J=8.0 Hz, 1H), 7.94 (bs, 1H), 7.70 (t, J=6.0 Hz, 1H), 7.62 (dd, J=2, 8 Hz, 2H), 7.43 (d, J=8.8 Hz, 1H), 7.35 (m, 2H), 7.25 (m, 3H), 7.19 (m, 1H), 6.71 (bs, 1H), 6.50 m (bt, 1H), 6.36 (s, 1H), 5.61 (s, 2H), 4.60 (d, J=4.0 Hz, 2H), 3.77 (dd, J=4.8, 17.6 Hz, 1H), 3.43 (dd, J=3.6, 17.6 Hz, 1H), 3.20 (s, 3H), 3.00 (d, J=5.2 Hz, 3H), 2.99 (m, 2H), 2.58 (s, 3H), 2.51-2.69 (m, 3H).

All references cited in this application are expressly incorporated by reference herein for any purpose.

Unless otherwise required by context, singular terms used herein shall include pluralities and plural terms shall include the singular.

EXAMPLES

The following examples, including the experiments conducted and results achieved are provided for illustrative purposes only and are not to be construed as limiting the invention.

Example 1

Compounds of Formula 1 Bind to Bradykinin B$_2$-Receptor

Compounds of Formula 1 were tested for ability to specifically bind to human recombinant BK B$_2$-receptor, and thus displace radiolabeled BK (for B$_2$-receptors) from the receptor, using competition radioligand binding techniques as described by Sharif and Whiting (*Neurochem. Int.* 18: 89-96, 1991) and Wiernas et al. (*Brit. J. Pharmacol.* 123: 1127-1137, 1998).

Chinese hamster ovary (CHO) cell membrane homogenates (2.5 µg protein) expressing the recombinant human bradykinin B$_2$ receptor were incubated for 60 min at 23° C. with 0.2 nM [$^3$H]-bradykinin (95.5 Ci/mmole, PerkinElmer) in the absence or presence of the test compound in a buffer containing 50 mM Tris/HCl (pH 7.4), 0.2 g/L 1-10-phenanthroline and 0.1% BSA. All reagent and test compound additions to the assay plates were made using Biomek 3000 robotic workstations (Beckman Instruments, Fullerton, Calif.). Nonspecific binding was determined in the presence of 1 µM unlabeled bradykinin. Following the incubation, the assay was terminated by rapid filtration under vacuum through glass fiber filters (GF/C, PerkinElmer) presoaked with 0.3% polyethyleneimine and rinsed several times with an ice-cold 50 mM Tris-HCl buffer using a 96-sample cell harvester (Tomtec). The filters were air-dried and the radioactivity counted in a beta-scintillation counter (Topcount, PerkinElmer) using a scintillation cocktail (Microscint 20, PerkinElmer) (Sharif and Whiting, *Neurochem. Int.* 18: 89-96, 1991). Competitive binding inhibition curves were generated using a 7-point concentration—response of test compound in duplicate. Bradykinin peptide was also tested as an internal control in the assay. The data were analyzed using nonlinear, iterative curve-fitting to obtain the potency and intrinsic activities of the test agents as previously described (Sharif et al. *J. Pharmacol. Exp. Ther.* 286: 1094-1102, 1998; Sharif et al. *Invest Ophthalmol. Vis. Sci.* 39:2562-2571, 1998; Kelly et al. *J. Pharmacol. Exp. Ther.* 304: 238-245, 2003). Determined IC$_{50}$ values were converted to K$_i$ values using the standard Cheng-Prusoff equation.

The results shown in Table 2 indicated that the tested compounds were able to interact with the agonist binding pocket of the B$_2$-receptor with greater affinity that Des-Arg$^9$-BK, which has high affinity for BK B$_1$-receptor. Furthermore, these compounds exhibited a reasonable affinity for the B$_2$-receptor as indicated by a low inhibition constant value (K$_i$) for competing for [$^3$H]-BK binding to the latter receptor.

TABLE 2

BK B$_2$-receptor binding affinity of bradykinin and some selected non-peptide BK agonists

| BK and Its Analogs & Non-peptide BK Compounds # | [$^3$H]-BK Binding to Human Cloned B$_2$ Receptor (K$_i$, nM) | [$^3$H]-BK Binding to Human Cloned B$_2$ Receptor (K$_i$, nM) |
|---|---|---|
| BK | 0.5 ± 0.05 | +++ |
| Lys-BK | 1.8 ± 0.7 | +++ |
| Hyp$^3$-BK | 1.9 ± 1.1 | +++ |
| Met-Lys-BK | 73 ± 25 | +++ |
| Des-Arg$^9$-BK | >10,000 | + |
| 1 | 54 | +++ |
| 2 | 101 | ++ |
| 3 | 273 | ++ |
| 4 | 158 | ++ |
| 5 | 71 ± 30 | +++ |
| 6 | 10 ± 2 | +++ |
| 7 | 118 ± 2 | ++ |
| 8 | 68 ± 16 | +++ |
| 9 | 667 ± 101 | ++ |
| 10 | 76 ± 16 | +++ |
| 11 | 391 ± 35 | ++ |
| 12 | 261 ± 195 | ++ |
| 14 | 197 | ++ |
| 15 | 467 | ++ |
| 16 | 985 ± 473 | ++ |
| 17 | 274 ± 69 | ++ |
| 18 | 239 ± 150 | ++ |
| 19 | 262 ± 11 | ++ |
| 20 | 1086 ± 138 | + |
| 21 | 881 ± 263 | ++ |
| 22 | 160 ± 47 | ++ |
| 23 | 1734 ± 428 | + |
| 24 | 171 ± 97 | ++ |
| 25 | 74 ± 6 | ++ |
| 26 | 2142 ± 223 | + |
| 27 | 11 | +++ |
| 28 | 3 ± 0.4 | +++ |
| 29 | 8 ± 3 | +++ |
| 30 | 3 ± 0.1 | +++ |
| 32 | 25 ± 8 | +++ |
| 33 | 7 ± 1 | +++ |
| 34 | 77 | +++ |
| 35 | 396 | +++ |
| 36 | 220 | +++ |
| 37 | 55.2 | +++ |
| 38 | 332 | +++ |
| 39 | 514 | +++ |
| 40 | 450 | +++ |
| 41 | 300 | ++ |
| 42 | 194 | +++ |
| 43 | NT | NT |
| 44 | 102 | +++ |

TABLE 2-continued

BK B$_2$-receptor binding affinity of bradykinin
and some selected non-peptide BK agonists

| BK and Its Analogs & Non-peptide BK Compounds # | [$^3$H]-BK Binding to Human Cloned B$_2$ Receptor (K$_i$, nM) | [$^3$H]-BK Binding to Human Cloned B$_2$ Receptor (K$_i$, nM) |
|---|---|---|
| 45 | 40 | +++ |
| 46 | NT | NT |
| 47 | NT | NT |
| 48 | NT | NT |
| 49 | NT | NT |
| 50 | 15 | +++ |
| 51 | 701 | ++ |
| 52 | 15.7 | +++ |
| 53 | 340 | ++ |
| 54 | 455 | ++ |
| 55 | 984 | ++ |
| 56 | 42 | +++ |
| 57 | 852 | ++ |
| 58 | 3150 | + |
| 59 | 2140 | + |
| 60 | NT | NT |
| 61 | 451 | ++ |
| 62 | 105 | ++ |
| 63 | 1190 | + |
| 64 | 40.3 | +++ |
| 65 | 98.4 | +++ |
| 66 | NT | NT |
| 67 | NT | NT |
| 68 | 59.5 | +++ |
| 69 | 178 | ++ |
| 70 | 599 | ++ |
| 71 | 17 | +++ |
| 72 | NT | NT |
| 73 | 184 | ++ |
| 74 | 384 | ++ |
| 75 | 544 | ++ |
| 76 | 237 | ++ |
| 77 | 229 | ++ |
| 78 | NT | NT |
| 79 | 859 | ++ |
| 80 | 279 | ++ |
| 81 | 108 | ++ |
| 82 | 205 | ++ |
| 83 | 329 | ++ |
| 84 | 78.3 | +++ |
| 85 | NT | NT |
| 86 | NT | NT |
| 87 | NT | NT |

+++ = <0.1 µM;
++ = >0.1 µM but <1 µM;
+ = >1 µM,
NT = not tested
Values are mean ± SEM or singular where they are averaged values from multiple experiments or from a single experiment. K$_i$ is the equilibrium concentration required to inhibit the binding of [$^3$H]-BK to the B$_2$-receptor and is inversely related to the receptor affinity. All values are in nM.

Example 2

Compounds of Formula 1 are BK Receptor Agonists

Functional Assay Measuring [Ca$^{2+}$]$_i$ Mobilization in Cultured Cells

Agents that can specifically activate native or recombinant BK receptors present in isolated animal or human tissues [strips or rings] (Sharif and Whiting, *Neurochem. Int.* 18: 89-96, 1991; Rizzi et al. *Naunyn-Schmiedeberg Arch. Pharmacol.* 360: 361-367, 1999), in cultured cells of animal or human tissue source (Sharif et al., *Neurosci. Lett.* 86: 279-283, 1988; Sharif and Whiting, *Neurochem. Res.* 12: 1313-1320, 1993), especially primary or immortalized ocular cells involved in aqueous humor dynamics such as human trabecular meshwork (h-TM) (Sharif and Xu, *Exp. Eye Res.* 63: 631-637, 1996), human ciliary muscle (h-CM; Sharif et al. *J. Ocular Pharmacol. Ther.* 19: 437-455, 2003), and non-pigmented ciliary epithelial (NPE; Crider and Sharif, *J. Ocular Pharmacol. Ther.* 18: 221-230, 2002) cells can be identified by measuring second messengers such as intracellular Ca$^{2+}$ ([Ca$^{2+}$]$_i$) (Kelly and Sharif, *J. Pharmacol. Expt. Ther.* 317: 1254-1261, 2006) produced after stimulation of the BK receptor(s) using well documented procedures.

To determine whether the compounds of the invention could activate BK receptors, a functional assay was conducted to measure [Ca$^{2+}$]$_i$ mobilized by BK or compounds of the invention in human ciliary muscle cells (h-CM) as previously described (Sharif et al. *J. Ocular Pharmacol. Ther.* 19: 437-455, 2003; Sharif et al., *J. Ocular Pharmacol. Ther.* 18: 141-162, 2002; Sharif et al. *Invest. Ophthalmol. Vis. Res.* 47: 4001-4019, 2006; Sharif et al., *J. Ocular Pharmacol. Ther.* 22: 291-309, 2006). BK-induced [Ca$^{2+}$]$_i$ mobilization was examined using the Fluorescence Imaging Plate Reader (FLIPR) instrument (Kelly and Sharif, *J. Pharmacol. Expt. Ther.* 317: 1254-1261, 2006).

h-CM cells expressing BK receptors were seeded at a density of about 20,000 cells/well in a black-wall, 96-well tissue culture plates and grown for 2 days. On the day of the experiment, media was removed, cells were rinsed and 50 µL of serum-free media added. One vial of FLIPR Calcium Assay Kit dye was reconstituted in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 µL) to each well of the 96-well plate and incubated with dye for 1 h at 23° C. Test compounds were stored at 25 µM in 100% DMSO solvent with intermediate dilution in 25% DMSO/25% Ethanol and final dilutions in FLIPR buffer. For agonist concentration response experiments, compounds were serially diluted 10-fold to give 5-point activity curves. After this time, the test compound plate and cell plate were placed in a Fluorescence Imaging Plate Reader (FLIPR-Tetra®) instrument (Molecular Devices/MDSPharma, Sunnyvale, Calif.). At the beginning of an experimental run, a signal test was performed to check the basal fluorescence signal from the dye-loaded cells and the uniformity of the signal across the plate. Instrument settings for a typical assay were the following: LED $\lambda_{ex}$=470-495 nm, $\lambda_{em}$=515-575 nm, camera F-stop F/2, and exposure time 0.4 sec. An aliquot (25 µL) of the test compound was added to the existing 100 µL dye-loaded cells at a dispensing speed of 50 µL/sec. Intracellular calcium mobilization was measured by monitoring real-time changes in cellular fluorescence upon test compound addition. Fluorescence data were collected in real-time at 1.0 sec intervals for the first 60 seconds and at 6.0 second intervals for an additional 120 seconds. Baseline fluorescence readings were normalized across the plate and background-corrected from negative control wells. Responses were measured as peak fluorescence intensity and where appropriate were expressed as a percentage of a maximum BK-induced response [E$_{max}$%]. EC$_{50}$ values were determined by 4-parameter nonlinear curve fitting of the concentration-response curve. Calibration of the instrument was performed using manufacturer's standard procedures.

The sources of materials and reagents for such assays can be found in the references cited above. The results demonstrated that the compounds of the invention are functional BK agonists (Table 3).

TABLE 3

| Compound # | CaM (EC$_{50}$, nM) |
|---|---|
| 1 | +++ |
| 2 | +++ |
| 3 | +++ |

TABLE 3-continued

| Compound # | CaM (EC$_{50}$, nM) |
|---|---|
| 4 | ++ |
| 5 | ++ |
| 6 | +++ |
| 7 | +++ |
| 8 | +++ |
| 9 | +++ |
| 10 | +++ |
| 11 | +++ |
| 12 | +++ |
| 13 | ++ |
| 14 | ++ |
| 15 | ++ |
| 16 | ++ |
| 17 | ++ |
| 18 | ++ |
| 19 | +++ |
| 20 | ++ |
| 21 | ++ |
| 22 | +++ |
| 23 | + |
| 24 | +++ |
| 25 | +++ |
| 26 | ++ |
| 27 | ++ |
| 28 | ++ |
| 29 | ++ |
| 30 | ++ |
| 31 | +++ |
| 32 | +++ |
| 33 | +++ |
| 34 | +++ |
| 35 | +++ |
| 36 | +++ |
| 37 | +++ |
| 38 | +++ |
| 39 | ++ |
| 40 | +++ |
| 41 | +++ |
| 42 | +++ |
| 43 | +++ |
| 44 | +++ |
| 45 | +++ |
| 46 | ++ |
| 47 | ++ |
| 48 | +++ |
| 49 | ++ |
| 50 | ++ |
| 51 | ++ |
| 52 | ++ |
| 53 | ++ |
| 54 | ++ |
| 55 | ++ |
| 56 | +++ |
| 57 | ++ |
| 58 | + |
| 59 | ++ |
| 60 | ++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |
| 72 | +++ |
| 73 | +++ |
| 74 | +++ |
| 75 | +++ |
| 76 | +++ |
| 77 | +++ |
| 78 | +++ |
| 79 | ++ |
| 80 | +++ |
| 81 | +++ |
| 82 | +++ |
| 83 | +++ |
| 84 | +++ |
| 85 | +++ |
| 86 | +++ |
| 87 | ++ |

+++ = <0.1 µM;
++ = >0.1 µM but <1 µM;
+ = >1 uM

Example 3

Compounds of Formula 1 Stimulate Production of Endogenous Prostaglandin in h-CM Cells BK agonist compounds of Formula 1 were evaluated for the ability to induce prostaglandin (PG) release from primary human ciliary muscle cells (h-CM). Briefly, h-CM cells were grown to confluence in FNC-coated 24-well culture plates and serum-starved (0.8% FBS) for 24 hours prior to the experiment. Cells were stimulated with a 9-pt concentration-response (0.1 nM-10 µM) of bradykinin or BK agonist for 1 hour at 37° C. with subsequent sample recovery and processing for total PG measurement. Total PG measurement was determined using a total Prostaglandin Screening EIA kit (cat#514012) purchased from Cayman Chemical (Ann Arbor, Mich.). The assay was conducted according to the package insert from the manufacturer. Potency values (EC$_{50}$) defined as the concentration of compound required to obtain 50% of maximal activity were determined by nonlinear curve fitting of the dose response data. Efficacy values (E$_{max}$, %) defined as the maximal response of the test compound relative to a high concentration of bradykinin set to 100%.

As shown in Table 4, a number of compounds of the present invention caused the production of endogenous PGs in h-CM cells.

TABLE 4

| Compound # | PG Release (EC$_{50}$, nM) |
|---|---|
| 1 | +++ |
| 2 | +++ |
| 3 | + |
| 4 | + |
| 5 | NT |
| 6 | +++ |
| 7 | +++ |
| 8 | +++ |
| 9 | ++ |
| 10 | + |
| 11 | + |
| 12 | + |
| 13 | + |
| 14 | NT |
| 15 | NT |
| 16 | NT |
| 17 | NT |
| 18 | NT |
| 19 | + |
| 20 | + |
| 21 | NT |
| 22 | + |
| 23 | NT |
| 24 | ++ |
| 25 | ++ |
| 26 | NT |

TABLE 4-continued

| Compound # | PG Release (EC$_{50}$, nM) |
|---|---|
| 27 | ++ |
| 28 | +++ |
| 29 | + |
| 30 | ++ |
| 31 | ++ |
| 32 | +++ |
| 33 | +++ |
| 34 | +++ |
| 35 | ++ |
| 36 | ++ |
| 37 | +++ |
| 38 | +++ |
| 39 | ++ |
| 40 | ++ |
| 41 | ++ |
| 42 | ++ |
| 43 | +++ |
| 44 | +++ |
| 45 | +++ |
| 46 | +++ |
| 47 | +++ |
| 48 | ++ |
| 49 | ++ |
| 50 | NT |
| 51 | NT |
| 52 | NT |
| 53 | NT |
| 54 | NT |
| 55 | NT |
| 56 | +++ |
| 57 | + |
| 58 | NT |
| 59 | NT |
| 60 | NT |
| 61 | + |
| 62 | ++ |
| 63 | + |
| 64 | +++ |
| 65 | +++ |
| 66 | ++ |
| 67 | + |
| 68 | ++ |
| 69 | +++ |
| 70 | ++ |
| 71 | +++ |
| 72 | + |
| 73 | ++ |
| 74 | ++ |
| 75 | ++ |
| 76 | + |
| 77 | ++ |
| 78 | +++ |
| 79 | + |
| 80 | ++ |
| 81 | + |
| 82 | + |
| 83 | + |
| 84 | +++ |
| 85 | +++ |
| 86 | +++ |
| 87 | +++ |

+++ = <0.1 µM;
++ = >0.1 µM but <1 µM;
+ = >1 µM

The results are relevant since PGs are highly potent IOP-lowering agents in ocular hypertensive monkeys (Hellberg et al. *J Ocular Pharmacol Ther.* 17: 421-432, 2001; Sharif et al. *J Ocular Pharmacol Ther.* 20: 489-508, 2004) and in humans (Alm, *Prog Ret Eye Res.* 17: 291-312, 1998). Thus, the compounds of the present invention can be expected to lower IOP in experimental animals, as shown below.

Example 4

Compounds of Formula 1 Reduce IOP Response in Lasered (Hypertensive) Eyes of Cynomolgus Monkeys Intraocular pressure (IOP) was determined with an Alcon Pneumatonometer (Alcon Laboratories, Inc., Fort Worth, Tex.) after light corneal anesthesia with 0.1% proparacaine. Right eyes were hypertensive as a result of laser trabeculoplasty. After a baseline IOP measurement, compounds of Formula 1 were administered topical ocularly in various formulations (including hydroxypropyl methylcellulose (0.5%), anhydrous dibasic sodium phosphate (0.2-0.5%), sodium chloride (0.5-0.75%), disodium EDTA (Edetate disodium) (0.01%), polysorbate 80 (0.05%), benzalkonium chloride (0.01%), sodium hydroxide/hydrochloric acid (for adjusting pH to 7.3-7.4), purified water (q.s. to 100%), and xanthan gum (0.5-6.0%), anhydrous dibasic sodium phosphate (0.2%), sodium chloride (0.5%), disodium EDTA (Edetate disodium) (0.01%), polysorbate 80 (0.05%), benzalkonium chloride (0.01%), sodium hydroxide/hydrochloric acid (for adjusting pH to 7.3-7.4), purified water (q.s. to 100%) with PEG400 (0-8.0%)) in conscious ocular hypertensive Cynomolgus monkeys. Vehicles were formulated and used in the current studies (including hydroxypropyl methylcellulose (0.5%), anhydrous dibasic sodium phosphate (0.2-0.5%), sodium chloride (0.5-0.75%), disodium EDTA (Edetate disodium) (0.01%), polysorbate 80 (0.05%), benzalkonium chloride (0.01%), sodium hydroxide/hydrochloric acid (for adjusting pH to 7.3-7.4), purified water (q.s. to 100%), and xanthan gum (0.5-6.0%), anhydrous dibasic sodium phosphate (0.2%), sodium chloride (0.5%), disodium EDTA (Edetate disodium) (0.01%), polysorbate 80 (0.05%), benzalkonium chloride (0.01%), sodium hydroxide/hydrochloric acid (for adjusting pH to 7.3-7.4), purified water (q.s. to 100%) with PEG400 (0-8.0%)). Vehicle was instilled in the right eyes of 5-8 additional animals. Subsequent IOP measurements were taken at 24 hours. IOP measurements are also taken on left eyes (normotensive and untreated) at each of these time points. The percent change in IOP from baseline was determined for each animal for every IOP measurement (Sharif et al. *J. Ocular Pharmacol. Ther.* 17: 305-317, 2001; May et al., *J Pharmacol Exp Ther.* 306: 301-309, 2003; Sharif et al. *Invest. Ophthalmol. Vis. Res.* 47: 4001-4010, 2006). Group mean and standard error of the mean (SEM) were calculated.

As shown in Table 5, several of the compounds reduced monkey IOP (MIOP) by at least 15%.

TABLE 5

| Compound # | MIOP % change at 24 h |
|---|---|
| 1 | − |
| 4 | − |
| 7 | + |
| 8 | + |
| 9 | − |
| 10 | − |
| 12 | − |

TABLE 5-continued

| Compound # | MIOP % change at 24 h |
|---|---|
| 28 | + |
| 32 | + |
| 33 | + |
| 34 | + |
| 38 | − |
| 44 | + |
| 45 | − |
| 56 | + |
| 64 | + |
| 65 | − |
| 73 | − |
| 74 | + |
| 76 | − |
| 78 | + |
| 84 | − |

+ = 15% or better reduction
− = <15% reduction

It should be understood that the foregoing disclosure emphasizes certain specific embodiments of the invention and that all modifications or alternatives equivalent thereto are within the spirit and scope of the invention as set forth in the appended claims, including the use of different formulations shown for instance in the examples above.

What is claimed is:

1. A compound of Formula I:

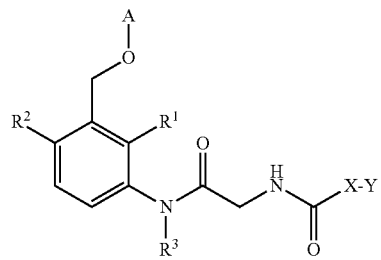

(Formula 1)

wherein,
$R^1$, $R^2$ independently= —$CH_3$ or —Cl;
$R^3$=$C_1$-$C_3$alkyl;

---

SEQUENCE LISTING

<160> NUMBER OF SEQ ID NOS: 3

<210> SEQ ID NO 1
<211> LENGTH: 9
<212> TYPE: PRT
<213> ORGANISM: Homo sapiens

<400> SEQUENCE: 1

Arg Pro Pro Gly Phe Ser Pro Phe Arg
1               5

<210> SEQ ID NO 2
<211> LENGTH: 10
<212> TYPE: PRT
<213> ORGANISM: Artificial
<220> FEATURE:
<223> OTHER INFORMATION: Synthetic peptide

<400> SEQUENCE: 2

Lys Arg Pro Pro Gly Phe Ser Pro Phe Arg
1               5                   10

<210> SEQ ID NO 3
<211> LENGTH: 8
<212> TYPE: PRT
<213> ORGANISM: Artificial
<220> FEATURE:
<223> OTHER INFORMATION: Synthetic peptide

<400> SEQUENCE: 3

Arg Pro Pro Gly Phe Ser Pro Phe
1               5

A is:

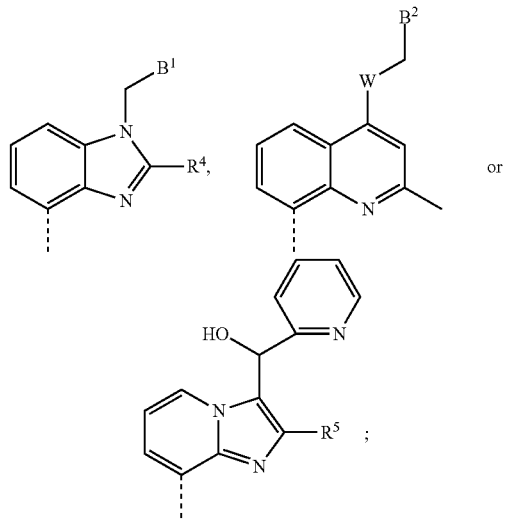

$R^4$=—$OR^5$, —$NR^7R^{10}$ or —$R^5$;
$R^5$=$C_1$-$C_3$ alkyl;
X=—$(CH_2)_n$—, —$CF_2CH_2$—;
n=1-3;
Y is:

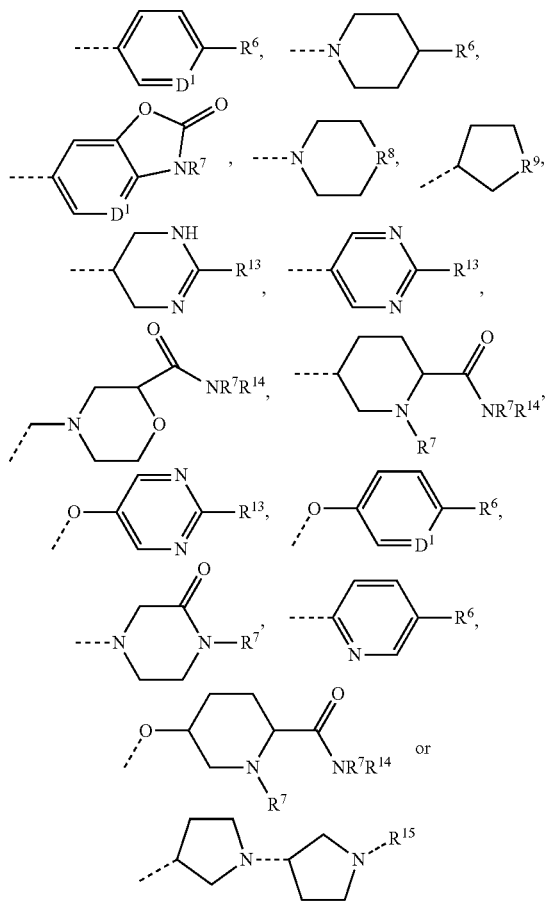

$D_1$=N, CH, $CR^5$, or $COR^5$;
$R^6$=—$C(O)OR^{10}$, —$N(R^{10})C(O)R^{11}$, —$N(R^{10})S(O_2)R^{11}$, —$C(O)N(R^{10})(R^{11})$, —$N(R^{10})C(O)OR^{11}$, —$N(R^{10})C(O)NR^7R^{11}$, $NR^{10}R^{12}$, or —$(CH_2)_mNR^{10}R^{12}$;
$R^7$=H or $C_1$-$C_3$ alkyl;

$R^8$=O, $NC(O)R^{11}$, $NS(O_2)R^{11}$, $NC(O)OR^{11}$, $NC(O)NR^7R^{11}$, or $NR^{11}$;
$R^9$=$NC(O)R^{11}$, $NS(O_2)R^{11}$, $NC(O)OR^{11}$, $NC(O)NR^7R^{11}$, or $NR^{11}$;
$R^{10}$=H or $C_1$-$C_3$ alkyl;
$R^{11}$=H, C1-C4 alkyl, or —$(CH_2)_p$—Z;
$R^{12}$=H, $C_1$-$C_3$ alkyl, or —$C(O)R^7$; m=, 1-3;
p=2-4;
Z=—OH or —$OR^{12}$;
$R^{13}$=—$N(R^{10})C(O)R^{11}$, —$N(R^{10})S(O_2)R^{11}$, —$C(O)N(R^{10})(R^{11})$, —$N(R^{10})C(O)OR^{11}$, or —$N(R^{10})C(O)NR^7R^{11}$;
$R^{14}$=—H, —$CH_3$, or -cyclopropyl
$R^{15}$=—H, $C_1$-$C_4$ alkyl, $C(O)OR^{11}$, —$C(O)N(R^{10})(R^{11})$ or —$(CH_2)_mNR^{10}R^{12}$;
W=-Q- or —NH—;
$B^1$ is:

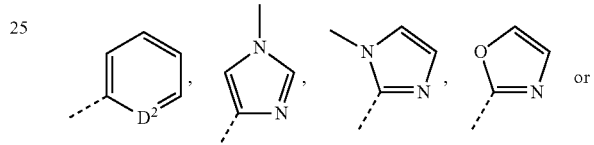

$D^2$=N, CH or CF;
; and
$B^2$ is:

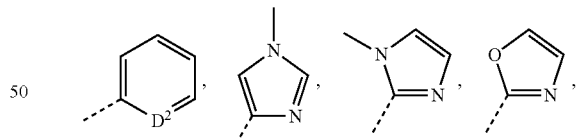

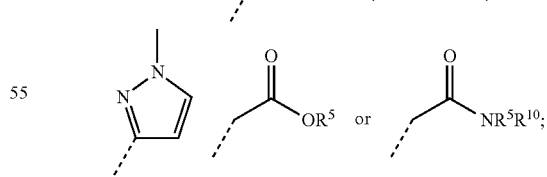

$D^2$=N, CH or CF.

2. A compound of claim 1, wherein:
$R^1$, $R^2$ independently=—$CH_3$ or —Cl;
$R^3$=$C_1$-$C_3$ alkyl;

A is:

[structure: benzimidazole with B¹-CH₂-N, R⁴] or [structure: quinoline with W-CH₂-B²];

R⁴=—OR⁵ or —NR⁷R¹⁰;
R⁵=C₁-C₃ alkyl;
X=—(CH₂)$_n$—;
n=1-3;
Y is:

[structures: phenyl-R⁶ with D¹; N-morpholine-R⁸; N-piperidine-R⁶; morpholine-C(O)NR⁷R¹⁴; spiro N/O ring with R⁹]

$D_1$=N, CH, CR⁵, or COR⁵;
R⁶=—N(R¹⁰)C(O)R¹¹, —C(O)N(R¹⁰)(R¹¹), or —N(R¹⁰)C(O)OR¹¹;
R⁷=—H or C₁-C₃ alkyl;
R⁸=—O—, —NC(O)R¹¹, —NC(O)OR¹¹, or —NC(O)NR⁷R¹¹;
R⁹=NC(O)R¹¹ or NC(O)OR¹¹;
R¹⁰=—H or C₁-C₃ alkyl;
R¹¹=—H, —C₁-C₄ alkyl or —(CH₂)$_p$—Z;
R¹⁴=—H, —CH₃, or -cyclopropyl;
p=2-4;
Z=—OH or —OR¹²;
W=—O— or —NH—;
B¹ is:

[structures: pyridine, fluorophenyl, or N-methylimidazole]

and
B²=B¹.

3. A compound of claim 2, wherein the compound is selected from the group consisting of:
Compound 7, 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpiperazine-1-carboxamide Compound 8, 3-(4-acetamidopiperidin-1-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide;

Compound 28, 3-(4-acetamidophenyl)-N-(2-((2,4-dichloro-3-(((2-methyl-4-(pyridin-2-ylmethoxy)quinolin-8-yl)oxy)methyl)phenyl)(methyl)amino)-2-oxoethyl)propanamide;

Compound 32, 3-(6-acetamidopyridin-3-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide;

Compound 33, 4-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylbenzamide;

Compound 44, 4-(2-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-2-oxoethyl)-N-methylmorpholine-2-carboxamide;

Compound 56, 4-(3-((2-((3-(((2-methoxy-1-(pyridin-2-ylmethyl)-1H-benzo[d]imidazol-4-yl)oxy)methyl)-2,4-dimethylphenyl)(methyl)amino)-2-oxoethyl)amino)-3-oxopropyl)-N-methylbenzamide;

Compound 64, 5-(3-((2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)amino)-3-oxopropyl)-N-methylpicolinamide;

Compound 74, 3-(6-(2-aminoacetamido)pyridin-3-yl)-N-(2-((2,4-dichloro-3-(((2-methoxy-1-(pyridin-2-ylmethyl)-1H-benzo[d]imidazol-4-yl)oxy)methyl)phenyl)(methyl)amino)-2-oxoethyl)propanamide; and Compound 78, 4-(3-((2-((2,4-dichloro-3-(((2-methoxy-1-((1-methyl-1H-imidazol-4-yl)methyl)-1H-benzo[d]imidazol-4-yl)oxy)methyl)phenyl)(methyl)amino)-2-oxoethyl)amino)-3-oxopropyl)-N-methylbenzamide.

4. A pharmaceutical composition comprising a compound of claim 1.

5. A topical ophthalmic composition comprising a therapeutically effective amount of a compound of claim 1, and one or more ingredients selected from the group consisting of surfactants, tonicity agents, buffers, preservatives, co-solvents, and viscosity building agents.

6. The composition: of claim 5, wherein the therapeutically effect amount of the compound is between 0.001-1.0%.

7. The composition of claim 6, wherein the therapeutically effect amount of the compound is 0.005%.

* * * * *